(12) United States Patent
Yamada et al.

(10) Patent No.: US 7,785,719 B2
(45) Date of Patent: Aug. 31, 2010

(54) FLUORENE COMPOUND AND ORGANIC LIGHT-EMITTING DEVICE

(75) Inventors: Naoki Yamada, Inagi (JP); Akihito Saitoh, Yokohama (JP); Keiji Okinaka, Kawasaki (JP); Masataka Yashima, Tokyo (JP); Akihiro Senoo, Kawasaki (JP); Kazunori Ueno, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 1167 days.

(21) Appl. No.: 11/284,814

(22) Filed: Nov. 23, 2005

(65) Prior Publication Data

US 2006/0121312 A1    Jun. 8, 2006

(30) Foreign Application Priority Data

Nov. 26, 2004   (JP)   ............................. 2004-342465

(51) Int. Cl.
  *H01L 51/54*   (2006.01)
(52) U.S. Cl. ........................ 428/690; 428/917; 313/504; 313/506
(58) Field of Classification Search ........................ None
See application file for complete search history.

(56) References Cited

U.S. PATENT DOCUMENTS 4,539,507 A    9/1985  VanSlyke et al. ............ 313/504

(Continued)

FOREIGN PATENT DOCUMENTS

JP    02-247278    10/1990

(Continued)

OTHER PUBLICATIONS

Betzig et al., "Collection Mode Near-Field Scanning Optical Microscopy," *Appl. Phys. Lett.*, vol. 51, No. 25, 2088-2091 (1987).

(Continued)

*Primary Examiner*—Dawn Garrett
(74) *Attorney, Agent, or Firm*—Fitzpatrick, Cella, Harper & Scinto

(57) ABSTRACT

The present invention provides a fluorene compound having a novel substituent, and the fluorene compound is represented by the following formula [1]:

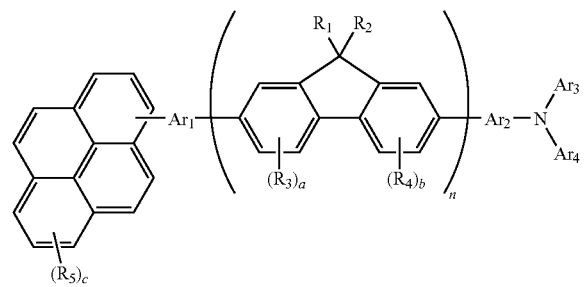

1 Claim, 2 Drawing Sheets

U.S. PATENT DOCUMENTS

| | | | |
|---|---|---|---|
| 4,720,432 A | 1/1988 | VanSlyke et al. | 428/457 |
| 4,885,211 A | 12/1989 | Tang et al. | 428/457 |
| 5,130,603 A | 7/1992 | Tokailin et al. | 313/504 |
| 5,151,629 A | 9/1992 | VanSlyke | 313/504 |
| 5,227,252 A | 7/1993 | Murayama et al. | 428/690 |
| 5,247,190 A | 9/1993 | Friend et al. | 257/40 |
| 5,317,169 A | 5/1994 | Nakano et al. | 257/40 |
| 5,382,477 A | 1/1995 | Saito et al. | 428/690 |
| 5,409,783 A | 4/1995 | Tang et al. | 428/690 |
| 5,514,878 A | 5/1996 | Holmes et al. | 257/40 |
| 5,672,678 A | 9/1997 | Holmes et al. | 528/373 |
| 5,726,457 A | 3/1998 | Nakano et al. | 257/40 |
| 2004/0253389 A1 | 12/2004 | Suzuki et al. | 428/1.1 |
| 2005/0106414 A1 | 5/2005 | Saitoh et al. | 428/690 |
| 2005/0236977 A1 | 10/2005 | Yamada et al. | 313/504 |
| 2005/0244676 A1 | 11/2005 | Arakane et al. | 428/690 |
| 2006/0113528 A1 | 6/2006 | Okinaka et al. | 257/40 |
| 2006/0115678 A1 | 6/2006 | Saitoh et al. | 428/690 |
| 2006/0166034 A1 | 7/2006 | Saitoh et al. | 428/690 |
| 2006/0255723 A1 | 11/2006 | Saitoh et al. | 313/504 |
| 2007/0155998 A1 * | 7/2007 | Saitoh et al. | 313/504 |

FOREIGN PATENT DOCUMENTS

| | | |
|---|---|---|
| JP | 03-255190 | 11/1991 |
| JP | 04-145192 | 5/1992 |
| JP | 05-202356 | 8/1993 |
| JP | 05-247460 | 9/1993 |
| JP | 09-202878 | 8/1997 |
| JP | 09-227576 | 9/1997 |
| JP | 10-090920 | 4/1998 |
| JP | 11-111460 | 4/1999 |
| JP | 2002-324678 | 11/2002 |
| JP | 2003-229273 | 8/2003 |
| JP | 2003-261471 | 9/2003 |
| JP | 2004-083481 | 3/2004 |
| JP | 2004-083513 | 3/2004 |
| JP | 2004-091350 | 3/2004 |
| WO | WO 2004/020372 * | 3/2004 |
| WO | WO 2004/020387 * | 3/2004 |
| WO | WO 2004/020388 * | 3/2004 |

OTHER PUBLICATIONS

Burroughes et al., "Light-Emitting Diodes Based on Conjugated Polymers," *Nature*, vol. 347, 539-541 (1990).

Baldo et al., "Highly Efficient Phosphorescent Emission from Organic Electroluminescent Devices," *Nature*, vol. 395, 151-154 (1998).

* cited by examiner

FLUORENE COMPOUND AND ORGANIC LIGHT-EMITTING DEVICE

BACKGROUND OF THE INVENTION

1. Field of the Invention

The present invention relates to a novel organic compound and an organic light-emitting device using the same.

2. Related Background Art

An organic light-emitting device has a thin film containing a fluorescent compound interposed between an anode and a cathode, and utilizes light emitted when excitons of the fluorescent compound generated by injection of electrons and holes from each electrode returns to the ground state.

A research by Eastman Kodak Company in 1987 (Appl. Phys. Lett. 51, 913 (1987)) reports light emission of about 1000 cd/m$^2$ at an applied voltage of about 10V in a separated-function two-layer structure device in which ITO is used for the anode, magnesium-silver alloy for the cathode, an aluminum quinolinol complex as an electron-transporting material and a light-emitting material, and a triphenylamine derivative as a hole-transporting material (U.S. Pat. Nos. 4,539,507, 4,720,432 and 4,885,211).

In addition, by changing the kind of fluorescent organic compounds, ultra-violet to infrared light can be emitted, and various compounds are now being actively studied (U.S. Pat. Nos. 5,151,629, 5,409,783 and 5,382,477, Japanese Patent Application Laid-Open Nos. H02-247278, H03-255190, H05-202356, H09-202878 and H09-227576).

Recently, a number of studies have been made on utilization of triplet energy for electroluminescence using a phosphorescent compound as a light-emitting material. A group in Princeton University has reported that an organic light-emitting device in which an iridium complex is used as a light-emitting material has high luminous efficiency (Nature, 395, 151 (1998)).

In addition to organic light-emitting devices using a low molecular weight material described above, an organic light emitting device using a conjugated polymer has been reported by a group in Cambridge University (Nature, 347, 539 (1990)). In this report, by forming a film of poly(phenylenevinylene) (PPV) in a coating system, light emission is found in a single layer. Patents related to organic light emitting devices using conjugated polymer include U.S. Pat. Nos. 5,247,190, 5,514,878 and 5,672,678, Japanese Patent Application Laid-Open Nos. H04-145192 and H05-247460.

As described above, recent development in organic light emitting devices is remarkable, and since they have features of high luminance at a low applied voltage, variety in emission wavelength and fast response, and since it is possible to fabricate thin and lightweight light emitting devices, they are expected to be used in a broad range of applications.

At present, however, light output of higher luminance or higher conversion efficiency is required. In addition, there are still many problems in durability such as degradation with the elapse of time due to long term use and use in ambient gas containing oxygen or moisture. Further, when application to full color displays is intended, light emission of blue, green and red with high color purity is required. However, there is no satisfactory solution for these problems and various proposals are now being made.

Examples of materials containing a benzene ring substituted by pyrene and organic light emitting devices using the same are described in Japanese Patent Application Laid-Open No. 2002-324678. However, although the application discloses that it provides a device excellent in luminescent properties and durability, the device has low external quantum efficiency, and there is no specific description of durability and lifetime.

SUMMARY OF THE INVENTION

An object of the present invention is to provide a fluorene compound having a novel substituent.

Another object of the present invention is to provide an organic light emitting device with light output of higher luminance at extremely high efficiency using a fluorene compound having a substituent. Still another object of the present invention is to provide an organic light-emitting device having extremely high durability and to provide an organic light-emitting device that can be easily produced at a relatively low cost.

Accordingly, the fluorene compound of the present invention is represented by the following formula [1]:

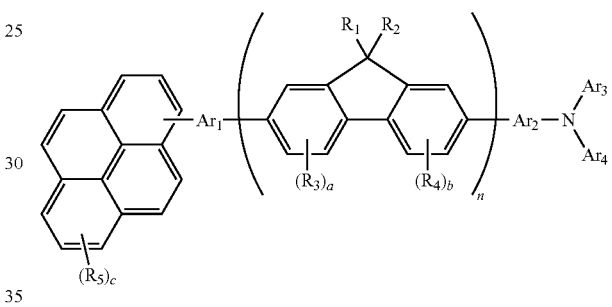

wherein $R_1$ to $R_5$ represent a hydrogen atom, a substituted or unsubstituted alkyl group, aralkyl group, aryl group, heterocyclic group, amino group or cyano group, or a halogen atom, and may be the same or different;

$Ar_1$ and $Ar_2$ represent a substituted or unsubstituted alkylene group, aralkylene group, arylene group or heterocyclic group, and $Ar_1$ and $Ar_2$ may be directly bonded;

$Ar_3$ and $Ar_4$ represent a substituted or unsubstituted alkyl group, aralkyl group, phenyl group, naphthyl group, pentalenyl group, indenyl group, azulenyl group, anthryl group, indacenyl group, acenaphthenyl group, phenanthryl group, phenalenyl group, fluoranthenyl group, acephenanthryl group, aceanthryl group, triphenylenyl group, chrysenyl group, naphthacenyl group, perylenyl group, pentacenyl group, biphenyl group, terphenyl group, fluorenyl group or heterocyclic group, with the proviso that the substituted phenyl group is selected from the group consisting of a dialkylphenyl group, a trialkylphenyl group, an o-alkylphenyl group, an m-alkylphenyl group, a p-alkylphenyl group, an aryl group-substituted phenyl group, a heterocyclic group-substituted phenyl group, a halophenyl group, an alkoxyphenyl group, an aminophenyl group and a cyanophenyl group, and $Ar_3$ and $Ar_4$ may be the same or different and may be bonded with each other to form a ring; and n is an integer of 1 to 10, a is an integer of 1 to 3, b is an integer of 1 to 3 and c is an integer of 1 to 9.

Another fluorene compound of the present invention is represented by the following formula [2]:

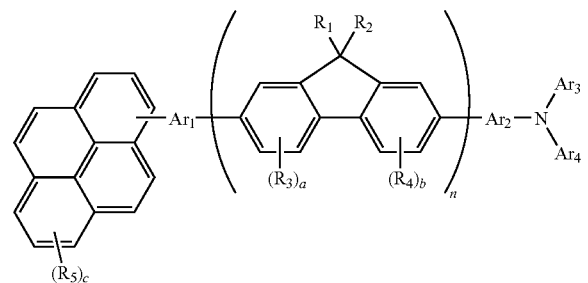

wherein $R_1$ to $R_5$ represent a hydrogen atom, a substituted or unsubstituted alkyl group, aralkyl group, aryl group, heterocyclic group, amino group or cyano group, or a halogen atom, and may be the same or different;

$Ar_1$ and $Ar_2$ represent a substituted or unsubstituted alkylene group, aralkylene group, arylene group or heterocyclic group, and $Ar_1$ and $Ar_2$ may be directly bonded;

$Ar_3$ represents a substituted or unsubstituted phenyl group, with the proviso that the substituted phenyl group is selected from the group consisting of a dialkylphenyl group, a trialkylphenyl group, an o-alkylphenyl group, an m-alkylphenyl group, an aryl group-substituted phenyl group, a heterocyclic group-substituted phenyl group, a halophenyl group, an alkoxyphenyl group, an aminophenyl group and a cyanophenyl group;

$Ar_4$ represents a substituted or unsubstituted alkyl group, aralkyl group, aryl group or heterocyclic group; and n is an integer of 1 to 10, a is an integer of 1 to 3, b is an integer of 1 to 3 and c is an integer of 1 to 9.

The organic light-emitting device of the present invention includes a pair of electrodes consisting of an anode and a cathode and at least one layer containing an organic compound interposed between the pair of electrodes, wherein the at least one layer containing an organic compound contains at least one kind of the above-described fluorene compounds.

The fluorene compound of the present invention is a material for an organic light-emitting device having multiple functions of highly efficient light emission and efficient transport of electrons and holes in one molecule. An organic light-emitting device using the fluorene compound of the present invention has realized highly efficient light emission at a low applied voltage. By changing the substituent of the fluorene compound various luminescent colors are easily obtained, and excellent durability is also obtained. And these organic light emitting devices can be applied to displays of personal computers, TVs, digital cameras and video cameras.

DETAILED DESCRIPTION OF THE PREFERRED EMBODIMENTS

Figure 1:
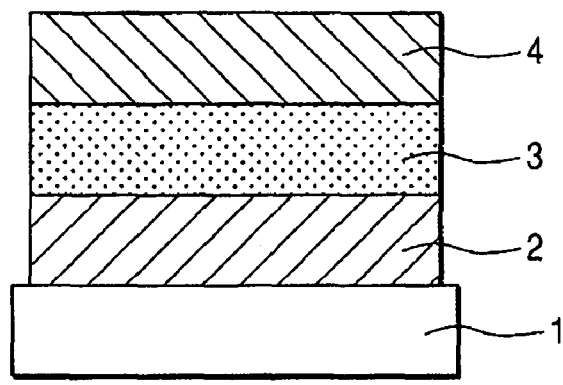
FIG. 1 is a cross-sectional view illustrating an example of an organic light-emitting device of the present invention.

The present invention is described in detail below.

First, the fluorene compound of the present invention is described.

The fluorene compound of the present invention may be mainly used as a material for an organic light-emitting device. In particular, when used for a light emission layer, the compound can be used alone as a light emission layer, or as a dopant (guest) material or a host material, and devices having high color purity, high luminous efficiency and long lifetime can be produced.

In the fluorene compound of the present invention, molecules have been designed so that an amino derivative group and a pyrene derivative group are distributed to a fluorene group in consideration of high luminous efficiency and multiple functions of efficient transport of electrons and holes in one molecule. Upon introduction of a substituted amino group into a fluorene group for the purpose of achieving high luminous efficiency and hole-transporting ability, change of the substituent on the amino group makes it possible to control the HOMO/LUMO level of the material and to convert light to blue, green or a luminescent color of a longer wavelength. In addition, due to estimation of the HOMO/LUMO level by calculation, molecular design in consideration of the difference in energy levels of a host material, a hole transport layer and an electron transport layer is easy. A pyrene derivative group has high quantum yield, and improvement in carrier-transporting ability due to overlap of pyrene rings can also be expected. Further, since Tg can be increased by an amino group, a material having good thermal stability can be obtained. The molecular design of the fluorene compound of the present invention has been made based on these studies and the present invention has been completed.

When the fluorene compound of the present invention is used as a dopant material, the concentration of the dopant in the host material is 0.01 wt % to 80 wt %, preferably 1 wt % to 40 wt %. The dopant material may be contained in the entire layer of a host material uniformly or with a concentration gradient, or contained in some region and the host material layer may have a region containing no dopant material.

Specific examples of substituents in the above-described formulas [1] and [2] are described below.

Examples of alkyl groups include a methyl group, an ethyl group, an n-propyl group, an iso-propyl group, an n-butyl group, a ter-butyl group, a sec-butyl group, an octyl group, a 1-adamantyl group and a 2-adamantyl group.

Examples of aralkyl groups include a benzyl group and a phenethyl group.

Examples of aryl groups include a phenyl group, a naphthyl group, a pentalenyl group, an indenyl group, an azulenyl group, an anthryl group, a pyrenyl group, an indacenyl group, an acenaphthenyl group, a phenanthryl group, a phenalenyl group, a fluoranthenyl group, an acephenanthryl group, an aceanthryl group, a triphenylenyl group, a chrysenyl group, a naphthacenyl group, a perylenyl group, a pentacenyl group, a biphenyl group, a terphenyl group and a fluorenyl group.

Examples of heterocyclic groups include a thienyl group, a pyrrolyl group, a pyridyl group, an oxazolyl group, an oxadiazolyl group, a thiazolyl group, a thiadiazolyl group, a terthienyl group, a carbazolyl group, an acridinyl group and a phenanthrolyl group.

Examples of substituted amino groups include a dimethylamino group, a diethylamino group, a dibenzylamino group, a diphenylamino group, a ditolylamino group and a dianisolylamino group.

Examples of halogen atoms include fluorine, chlorine, bromine and iodine.

Examples of substituent that the above-described substituent may have include alkyl groups such as a methyl group, an ethyl group and a propyl group; aralkyl groups such as a benzyl group and a phenethyl group; aryl groups such as a phenyl group and a biphenyl group; heterocyclic groups such as a thienyl group, a pyrrolyl group and a pyridyl group; amino groups such as a dimethylamino group, a diethylamino group, a dibenzylamino group, a diphenylamino group, a ditolylamino group and a dianisolylamino group; alkoxy groups such as a methoxyl group, an ethoxyl group, a propoxyl group and a phenoxyl group; a cyano group; and halogen atoms such as fluorine, chlorine, bromine and iodine.

In the fluorene compound represented by the formula [1] of the present invention, $Ar_3$ and $Ar_4$ are preferably a substituted or unsubstituted alkyl group, aralkyl group, naphthyl group, anthryl group, phenanthryl group, perylenyl group, biphenyl group, terphenyl group, fluorenyl group, or an unsubstituted phenyl group.

In the fluorene compound represented by the formula [2] of the present invention, $Ar_4$ is preferably a substituted or unsubstituted naphthyl group.

Typical examples of fluorene compounds of the present invention are listed below, but the present invention is not limited thereto.

TABLE 1
| Compound No. | Ar1 | 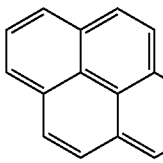 | Ar2 | Ar3 | Ar4 |
|---|---|---|---|---|---|
| A-1 | 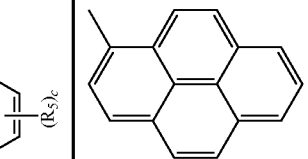 | 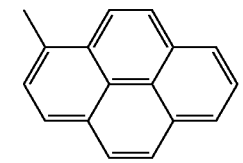 | Direct bond | 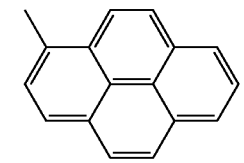 |  |
| A-2 | 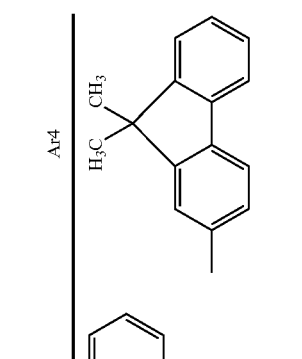 | 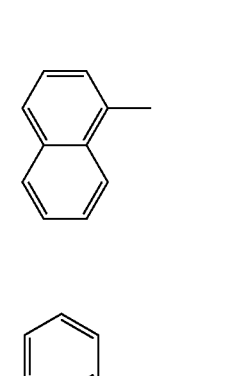 | Direct bond | 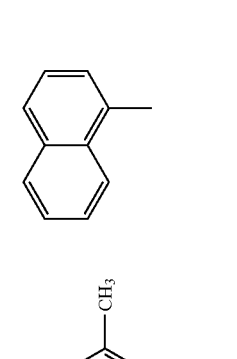 | 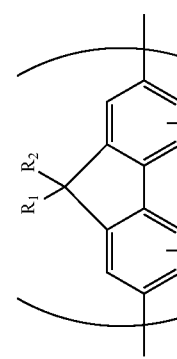 |
| A-3 | 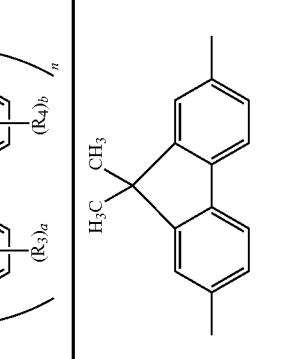 | 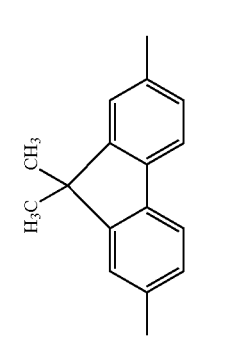 | Direct bond | 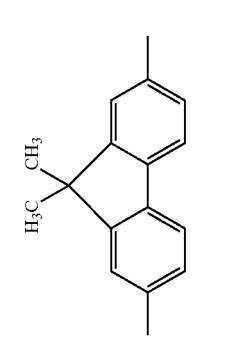 | 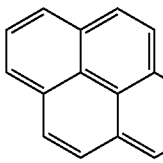 |

TABLE 1-continued

| Compound No. | Ar1 | (fluorene group) | Ar2 | Ar3 | Ar4 |
|---|---|---|---|---|---|
| A-4 | 1-methylpyrenyl | 9,9-dimethyl-2,7-fluorenylene | Direct bond | mesityl (2,4,6-trimethylphenyl) | mesityl (2,4,6-trimethylphenyl) |
| A-5 | 1-methylpyrenyl | 9,9-dimethyl-2,7-fluorenylene | Direct bond | tolyl | 9-methylphenanthrenyl |
| A-6 | 1-methylpyrenyl | 9,9-dimethyl-2,7-fluorenylene | Direct bond | N-methylcarbazolyl | N-methylcarbazolyl |

TABLE 1-continued
| Compound No. | Ar1 | (structure) | Ar2 | Ar3 | Ar4 |
|---|---|---|---|---|---|
| A-7 | 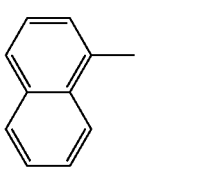 | Direct bond | 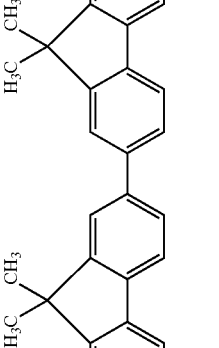 | 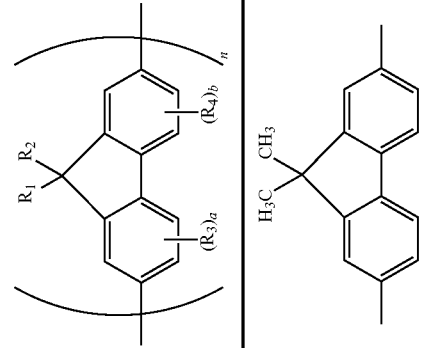 | 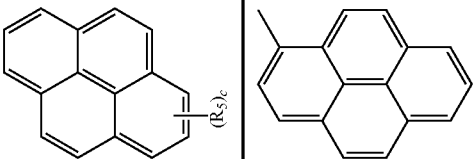 |
| A-8 | 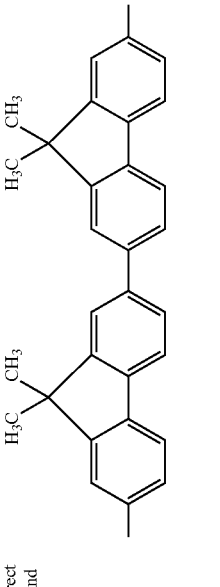 | Direct bond | 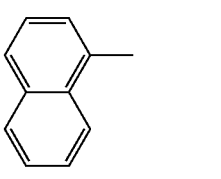 | 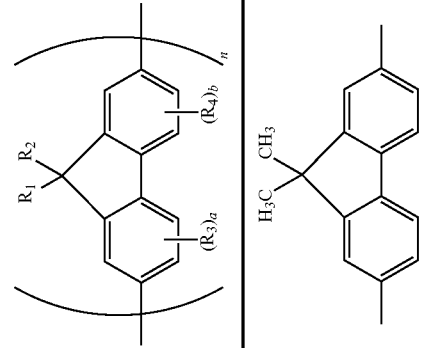 | 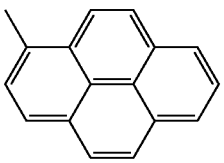 |
| A-9 | 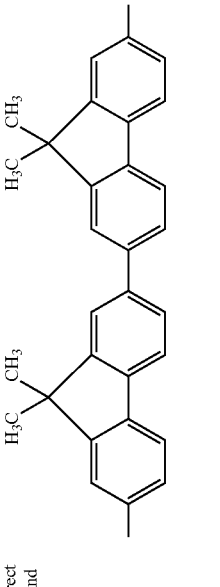 | Direct bond | 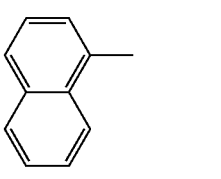 | 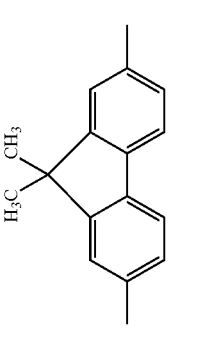 | 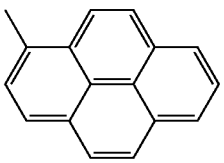 |

TABLE 1-continued
| Compound No. | Ar1 | | Ar2 | Ar3 | Ar4 |
|---|---|---|---|---|---|
| A-10 | 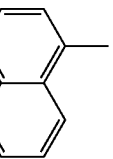 | Direct bond | 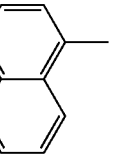 | 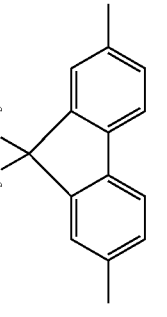 | 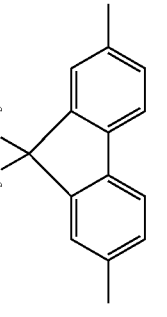 |

TABLE 2
| Compound No. | Ar1 | (fluorene core) | Ar2 | Ar3 | Ar4 |
|---|---|---|---|---|---|
| A-11 |  |  | (p-tolyl) | (3,5-dimethyl-4-methylphenyl, mesityl-like) | (2,4,6-trimethylphenyl) |
| A-12 | Direct bond |  | (m-tolyl) | (phenyl) | (1-naphthyl) |
| A-13 | Direct bond |  | (m-tolyl) | (phenyl) | (phenyl) |

TABLE 2-continued

| Compound No. | Ar1 | (structure with R1, R2, R3, R4, R5) | Ar2 | Ar3 | Ar4 |
|---|---|---|---|---|---|
| A-14 | Direct bond | 9,9-dimethylfluorene (2,7-substituted) | m-tolyl | o-tolyl | 1-naphthyl |
| A-15 | Direct bond | 9,9-dimethylfluorene (2,7-substituted) | m-tolyl | 1-naphthyl | 1-naphthyl |
| A-16 | Direct bond | 9,9-dimethylfluorene (2,7-substituted) | m-tolyl | mesityl (2,4,6-trimethylphenyl) | mesityl (2,4,6-trimethylphenyl) |

TABLE 2-continued

TABLE 2-continued
| Compound No. | Ar1 | | Ar2 | Ar3 | Ar4 |
|---|---|---|---|---|---|
| A-20 | 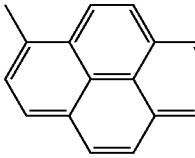 | Direct bond | 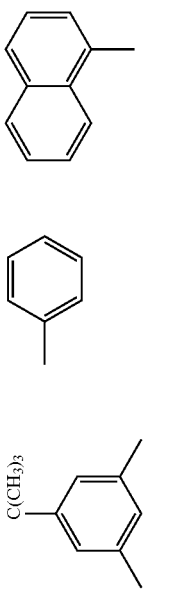 | 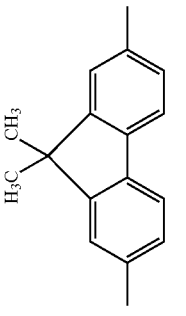 | |

TABLE 3
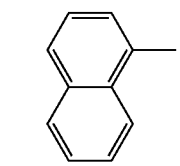

TABLE 3-continued

| Compound No. | Ar1 | | Ar2 | Ar3 | Ar4 |
|---|---|---|---|---|---|
| A-24 | | | | | |
| A-25 | | | | | |
| A-26 | | | | | |

TABLE 3-continued

| Compound No. | Ar1 | (structure) | Ar2 | Ar3 | Ar4 |
|---|---|---|---|---|---|
| A-27 | 4-methylphenyl | 2,7-dimethyl-9,9-dimethylfluorene | 4-methylphenyl | phenyl | 9,9-dimethylfluorene |
| A-28 | 3-methylphenyl | 2,7-dimethyl-9,9-dimethylfluorene | 4-methylphenyl | phenyl | phenyl |
| A-29 | 3,4-dimethylphenyl | 2,7-dimethyl-9,9-dimethylfluorene | 4-methylphenyl | phenyl | 1-naphthyl |

TABLE 3-continued

| Compound No. | Ar1 | | Ar2 | Ar3 | Ar4 |
|---|---|---|---|---|---|
| A-30 | (pyrene with methyl) | 3,5-dimethylphenyl | 9,9-dimethyl-2,7-dimethylfluorene | phenyl | naphthyl |

TABLE 4

| Compound No. | Ar1 | (fluorene group) | Ar2 | Ar3 | Ar4 | (pyrene group) |
|---|---|---|---|---|---|---|
| A-31 | 3,5-dimethylphenyl | 9,9-dimethyl-2,7-fluorenyl (dimethyl substituted) | 3,5-dimethylphenyl | phenyl | 1-naphthyl | 1-methylpyrenyl |
| A-32 | Direct bond | 9,9-dimethyl-2,7-fluorenyl (dimethyl substituted) | Direct bond | phenyl | 1-naphthyl | 1-methyl-6-tert-butylpyrenyl |

TABLE 4-continued

| Compound No. | (R5)c pyrene | Ar1 | R1 R2 / (R3)a (R4)b fluorene | Ar2 | Ar3 | Ar4 |
|---|---|---|---|---|---|---|
| A-33 | methyl-pyrene-t-butyl | Direct bond | H3C,CH3 fluorene with CH3 groups | 3,5-dimethylphenyl | 4-(C(CH3)3)phenyl | 3,7-dimethylnaphthyl |
| A-34 | methyl-pyrene-t-butyl | Direct bond | H3C,CH3 fluorene with dimethyl | 3,5-dimethylphenyl | 4-(C(CH3)3)phenyl | 1-naphthyl |

TABLE 4-continued
| Compound No. | (R₅)c (pyrene) | Ar1 | R₁ R₂ / (R₃)a / (R₄)b / n (fluorene) | Ar2 | Ar3 | Ar4 |
|---|---|---|---|---|---|---|
| A-35 |  | Direct bond | 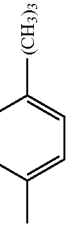 | 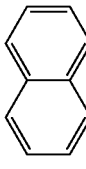 | 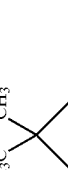 | 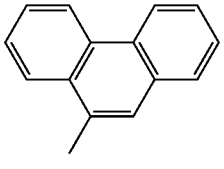 |
| A-36 | 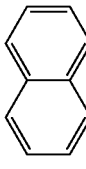 | Direct bond | | | | |

TABLE 4-continued

| Compound No. | Ar1 | | Ar2 | Ar3 | Ar4 |
|---|---|---|---|---|---|
| A-37 | (pyrene) | (m-xylylene) | (9,9-dimethyl-2,7-fluorenylene) | (p-phenylene) | (phenyl) | (1-methylnaphthyl with methylpyrene) |

TABLE 5
| Compound No. | (R₅)c [pyrene] | Ar1 | R₁ R₂ / (R₃)a / (R₄)b [fluorene] | Ar2 | Ar3 | Ar4 |
|---|---|---|---|---|---|---|
| A-38 | 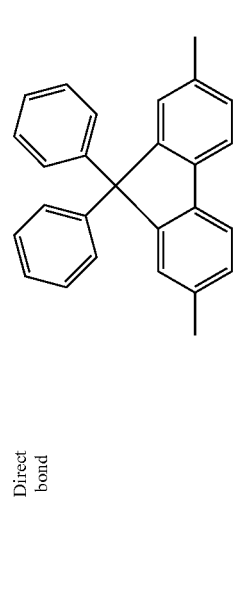 | 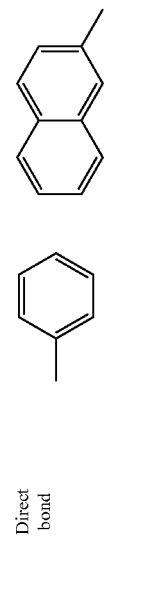 |  | 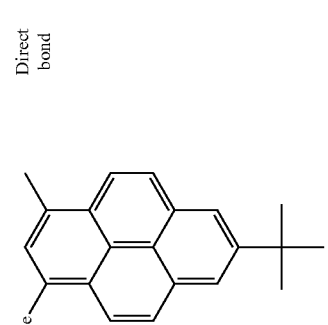 | 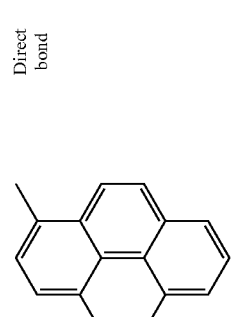 | 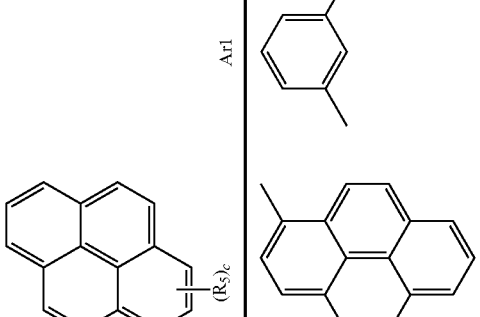 |
| A-39 | 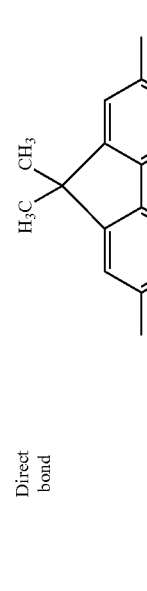 | Direct bond | 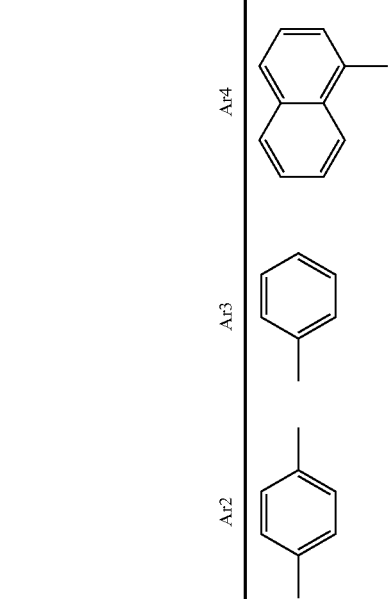 | Direct bond |  | 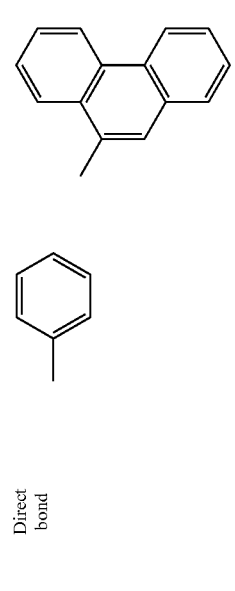 |
| A-40 |  | Direct bond | 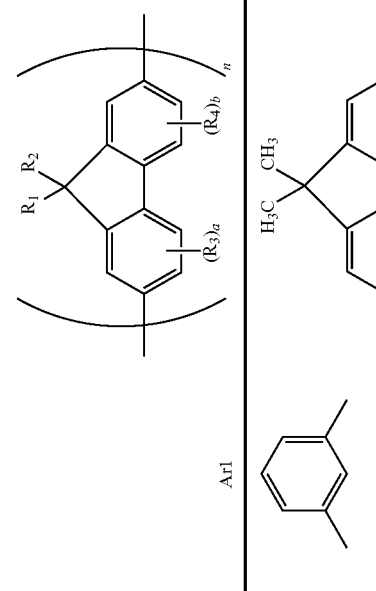 | Direct bond | | |

TABLE 5-continued

| Compound No. | Ar1 | (fluorene core) | Ar2 | Ar3 | Ar4 |
|---|---|---|---|---|---|
| A-41 | 3,5-dimethylphenyl | 9,9-dimethyl-2,7-fluorenylene (with methyl substituents) | Direct bond | phenyl | 2-naphthyl |
| A-42 | 3,5-dimethylphenyl | 9,9-dimethyl-2,7-fluorenylene (with methyl substituents) | Direct bond | phenyl | 1-naphthyl |
| A-43 | 3,5-dimethylphenyl | 9,9-dimethyl-2,7-fluorenylene (with methyl substituents) | Direct bond | phenyl | phenyl |

TABLE 5-continued
| Compound No. | | Ar1 | | Ar2 | Ar3 | Ar4 |
|---|---|---|---|---|---|---|
| A-44 | 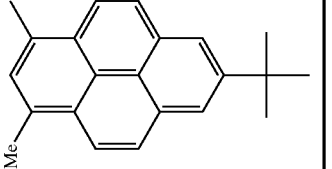 | Direct bond |  | Direct bond | 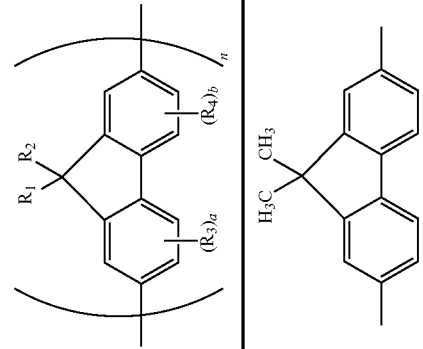 | 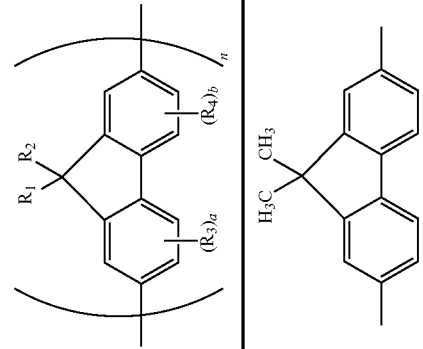 |
| A-45 | 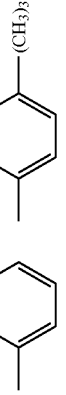 | Direct bond | 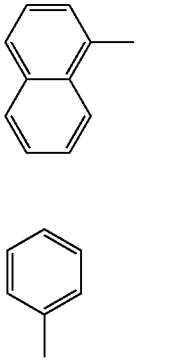 | Direct bond |  | 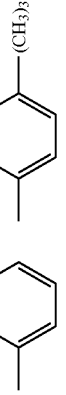 |

TABLE 6

| Compound No. | | Ar1 | | Ar2 | Ar3 | Ar4 |
|---|---|---|---|---|---|---|
| A-46 | (pyrene with Me, Me, t-Bu substituents) | Direct bond | (dimethylfluorene with C(CH3)2) | Direct bond | (phenyl) | (methylfluorene with C(CH3)2, CH3) |
| A-47 | (pyrene with Me, Me, t-Bu substituents) | Direct bond | (dimethylfluorene with C(CH3)2) | Direct bond | (phenyl) | (tert-butylphenyl, C(CH3)3) |

TABLE 6-continued

| Compound No. | (R5)c on pyrene | Ar1 | Fluorene (R1,R2,(R3)a,(R4)b) | Ar2 | Ar3 | Ar4 |
|---|---|---|---|---|---|---|
| A-48 | 1-methyl, 7-tert-butyl pyrene | Direct bond | 9,9-dimethyl-2,7-dimethylfluorene | m-tolyl | phenyl | 4-(C(CH3)3)phenyl |
| A-49 | 1,6-dimethyl, 8-tert-butyl pyrene | Direct bond | 9,9-dimethyl-2,7-dimethylfluorene | m-tolyl | phenyl | 4-(C(CH3)3)phenyl |

TABLE 6-continued

| Compound No. | (pyrene with R₅) | Ar1 | (fluorene with R₁R₂, R₃, R₄) | Ar2 | Ar3 | Ar4 |
|---|---|---|---|---|---|---|
| A-50 | | Direct bond | | | | |
| A-51 | | | | Direct bond | | |
| A-52 | | | | Direct bond | | |

TABLE 6-continued

| Compound No. | | Ar1 | | Ar2 | Ar3 | Ar4 |
|---|---|---|---|---|---|---|
| A-53 | 1-methylpyrene | 3,5-dimethylphenyl | 9,9-dimethyl-2,7-fluorenyl | Direct bond | phenyl | 1-naphthyl (4-substituted) |

TABLE 7
| Compound No. | 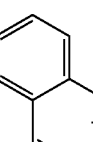 | Ar1 | 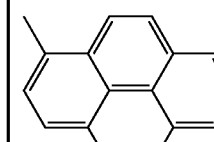 | Ar2 | Ar3 | Ar4 |
|---|---|---|---|---|---|---|
| A-54 | 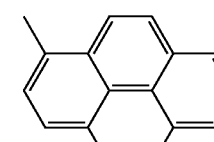 | 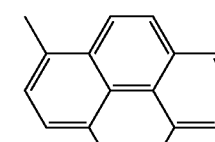 | 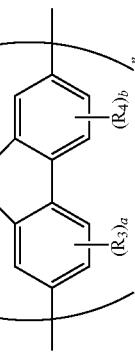 | Direct bond | 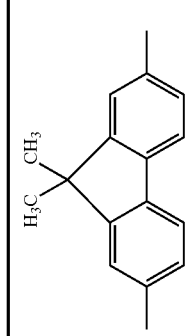 | 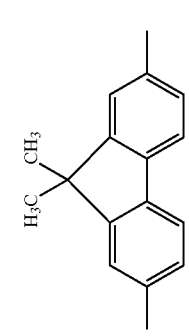 |
| A-55 | 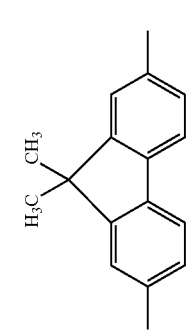 | 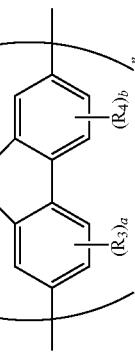 | 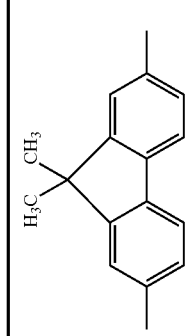 | Direct bond | 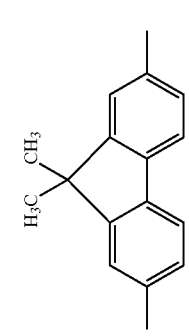 | 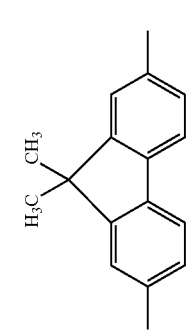 |
| A-56 | 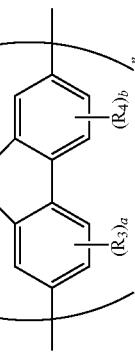 | 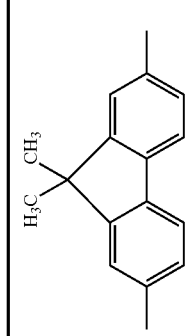 | 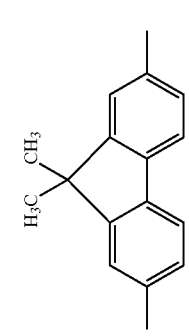 | 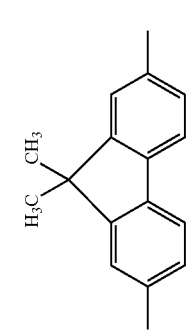 | 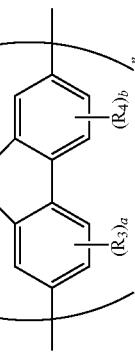 | 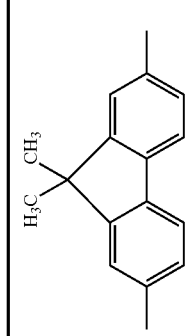 |

TABLE 7-continued

| Compound No. | (structure with (R5)c on pyrene) | Ar1 | (fluorene structure with R1 R2, (R3)a, (R4)b, n) | Ar2 | Ar3 | Ar4 |
|---|---|---|---|---|---|---|
| A-57 | methyl-pyrene-t-butyl | 3-methylphenyl | 9,9-dimethyl-2,7-dimethylfluorene | 3-methylphenyl | phenyl | 9,9-dimethyl-methylfluorene |
| A-58 | methyl-pyrene-t-butyl | 3-methylphenyl | 9,9-dimethyl-2,7-dimethylfluorene | Direct bond | phenyl | 4-(C(CH3)3)phenyl |

TABLE 7-continued
| Compound No. | 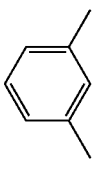 | Ar1 | 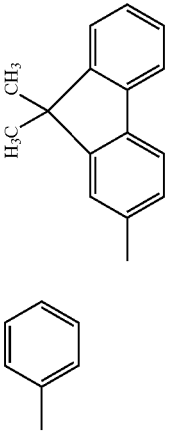 | Ar2 | Ar3 | Ar4 |
|---|---|---|---|---|---|---|
| A-59 | 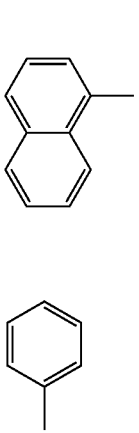 | 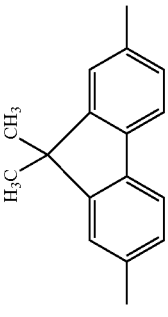 | 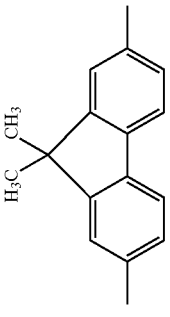 | Direct bond | 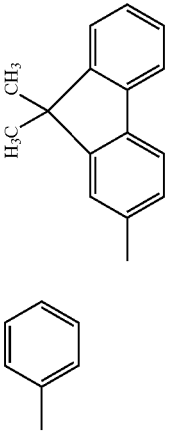 | 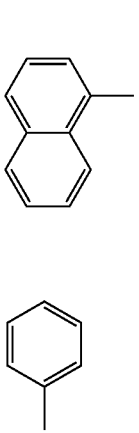 |
| A-60 | 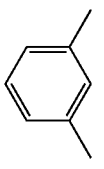 | | | Direct bond | | |

TABLE 7-continued

| Compound No. | Ar1 | | Ar2 | Ar3 | Ar4 |
|---|---|---|---|---|---|
| A-61 | (pyrene with methyl and t-butyl) | m-tolyl | 9,9-dimethyl-2,7-fluorenediyl | Direct bond | toluene | 2-methylnaphthalene |

TABLE 8

| Compound No. | | Ar1 | | Ar2 | Ar3 | Ar4 |
|---|---|---|---|---|---|---|
| A-62 | (pyrene with (R5)c) | 3,5-dimethylphenyl (CH3, CH3) | 9,9-dimethylfluorene with methyl substituents | Direct bond | phenyl | 4-tert-butylphenyl (C(CH3)3) |
| A-63 | methyl-pyrene-tert-butyl | 3,5-dimethylphenyl (CH3, CH3) | 9,9-dimethylfluorene with methyl substituents | Direct bond | phenyl | 9,9-dimethylfluorene with methyl |

TABLE 8-continued
| Compound No. | 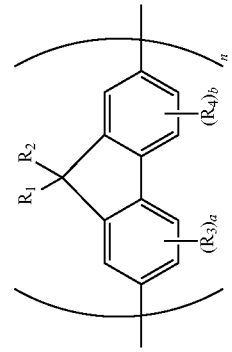 | Ar1 | 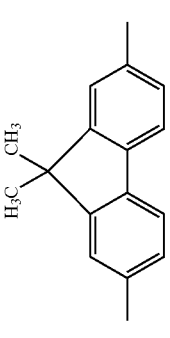 | Ar2 | Ar3 | Ar4 |
|---|---|---|---|---|---|---|
| A-64 | 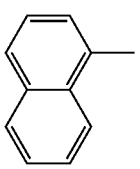 | 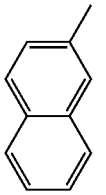 | 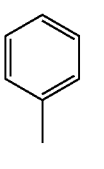 | Direct bond | 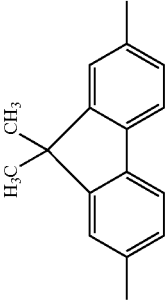 | 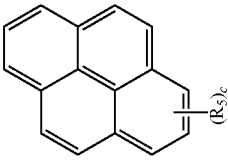 |
| A-65 | 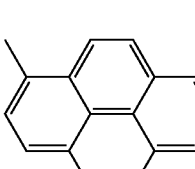 | 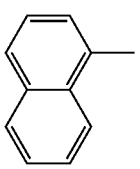 | 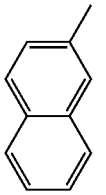 | Direct bond | 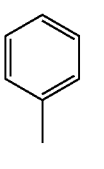 | 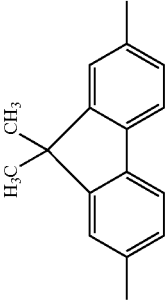 |

TABLE 8-continued

| Compound No. | (pyrene with (R5)c) | Ar1 | fluorene with R1 R2, (R3)a, (R4)b, n | Ar2 | Ar3 | Ar4 |
|---|---|---|---|---|---|---|
| A-66 | Me-pyrene-tBu (1,6-disubstituted) | m-xylyl | 9,9-dimethyl-2,7-fluorenyl | Direct bond | phenyl | p-tolyl (CH₃) |
| A-67 | Me-pyrene-tBu (1,6-disubstituted) | m-xylyl | 9,9-dimethyl-2,7-fluorenyl | Direct bond | phenyl | 9,9-dimethylfluorenyl |

TABLE 8-continued
| Compound No. | Ar1 | | Ar2 | Ar3 | Ar4 |
|---|---|---|---|---|---|
| A-68 | 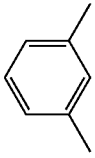 | 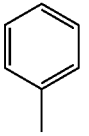 | 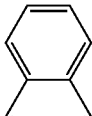 | Direct bond |  |

TABLE 9
| Compound No. | 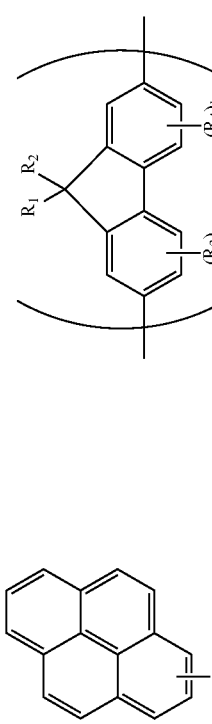 | Ar1 | 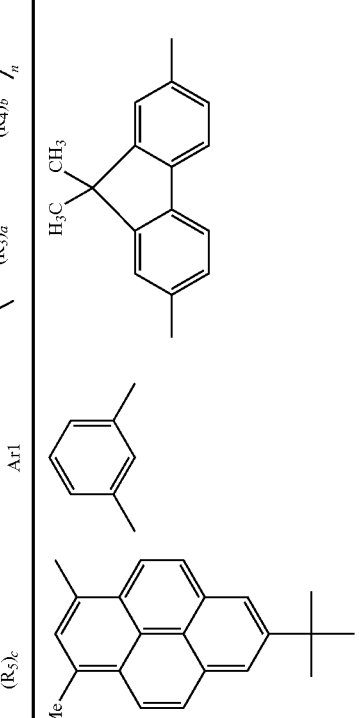 | Ar2 | Ar3 | Ar4 |
|---|---|---|---|---|---|---|
| A-69 | 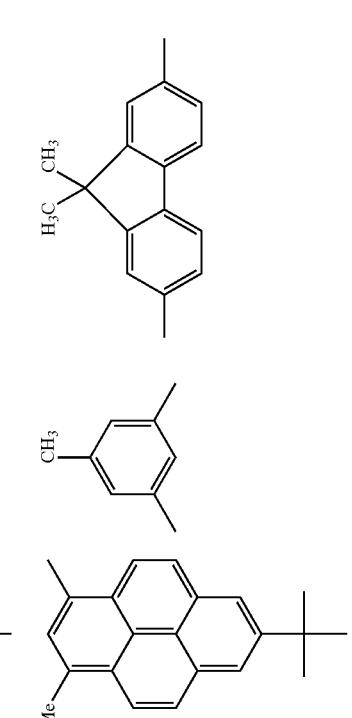 |  |  | Direct bond | 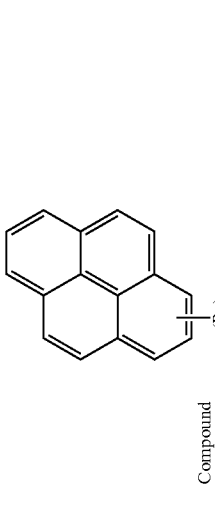 | 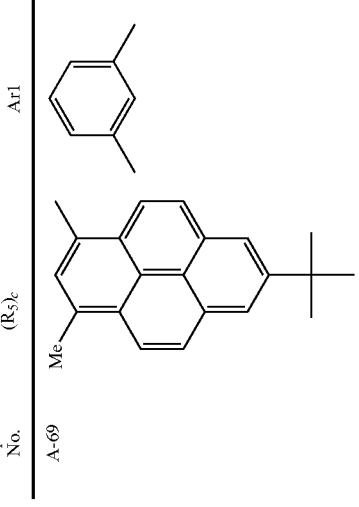 |
| A-70 | 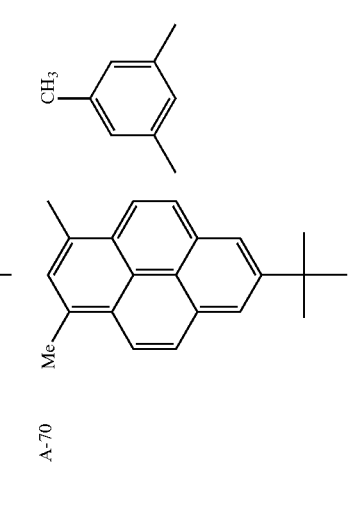 | 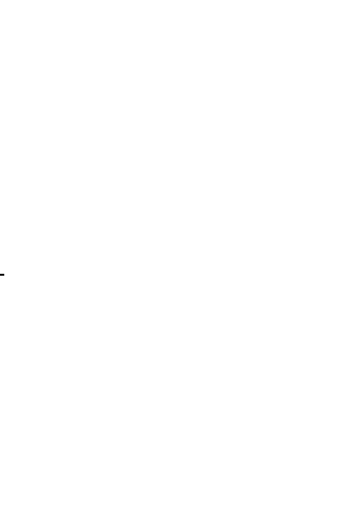 |  | Direct bond | | |

TABLE 9-continued

| Compound No. | (R5)c [pyrene] | Ar1 | R1 R2 / (R3)a / (R4)b [fluorene] | Ar2 | Ar3 | Ar4 |
|---|---|---|---|---|---|---|
| A-71 | Me-pyrene-tBu with Me | 3,5-dimethylphenyl | 9,9-dimethylfluorene (2,7-disubst) | Direct bond | phenyl | 9,9-dimethylfluorene |
| A-72 | Me-pyrene-tBu with Me | 3,5-dimethylphenyl | 9,9-dimethylfluorene (2,7-disubst) | Direct bond | phenyl | 1-methylnaphthyl |

TABLE 9-continued
| Compound No. | | Ar1 | | Ar2 | Ar3 | Ar4 |
|---|---|---|---|---|---|---|
| A-73 | 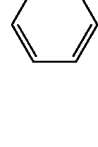 |  | 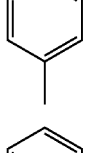 | Direct bond | 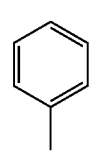 |  |
| A-74 | 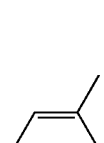 | Direct bond | 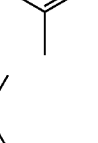 |  |  |  |
| A-75 | 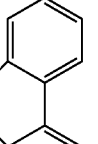 | Direct bond |  | | | |

TABLE 10
| Compound No. | 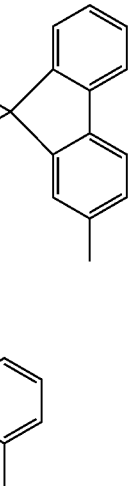 | Ar1 | | Ar2 | Ar3 | Ar4 |
|---|---|---|---|---|---|---|
| A-76 | 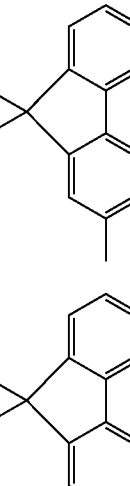 | Direct bond | 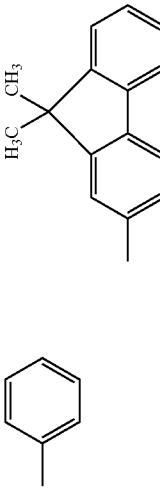 | 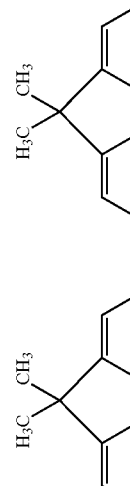 | 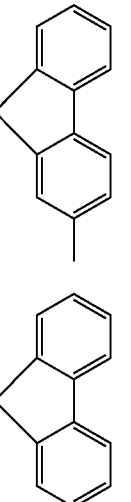 | 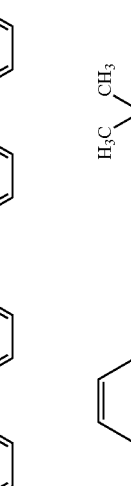 |
| A-77 | 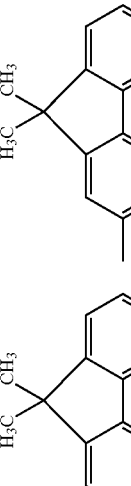 | Direct bond | 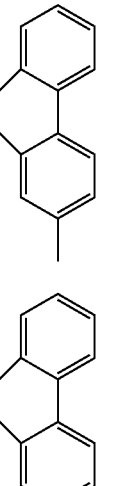 |  |  | 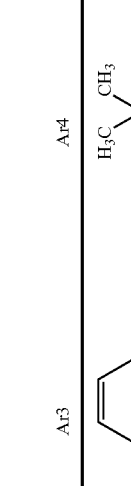 |
| A-78 | 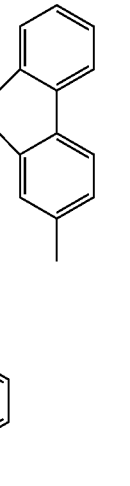 | Direct bond | 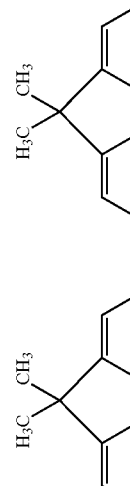 | | | |

TABLE 10-continued

| Compound No. | (R5)c [pyrene] | Ar1 | R1 R2 / (R3)a / (R4)b fluorene | Ar2 | Ar3 | Ar4 |
|---|---|---|---|---|---|---|
| A-79 | methyl-pyrene-tBu | Direct bond | 9,9-dimethyl-2,7-dimethylfluorene | 2,6-dimethylphenyl (m-xylyl) | 9,9-dimethyl-fluorenyl | 9,9-dimethyl-fluorenyl |
| A-80 | methyl-pyrene-tBu | Direct bond | 9,9-dimethyl-2,7-dimethylfluorene | 3,5-dimethylphenyl | phenyl | 9,9-dimethyl-fluorenyl |

TABLE 10-continued

| Compound No. | (R₅)c [pyrene] | Ar1 | R₁R₂ / (R₃)a / (R₄)b [fluorene] | Ar2 | Ar3 | Ar4 |
|---|---|---|---|---|---|---|
| A-81 | methyl-pyrenyl-tert-butyl | Direct bond | 9,9-dimethyl-2,7-dimethylfluorenyl | 3,5-dimethylphenyl | 9,9-dimethylfluorenyl | 9,9-dimethylfluorenyl |
| A-82 | dimethyl-pyrenyl-tert-butyl | Direct bond | 9,9-dimethyl-2,7-dimethylfluorenyl | 3-methylphenyl | phenyl | 9,9-dimethylfluorenyl |

The organic light-emitting device of the present invention will now be described in detail.

The organic light-emitting device of the present invention includes a pair of electrodes consisting of an anode and a cathode and at least one layer containing an organic compound interposed between the pair of electrodes, wherein the at least one layer containing an organic compound, preferably a light emission layer, contains at least one of the above-described fluorene compounds of the present invention.

When the layer containing at least one kind of the fluorene compounds of the present invention is a light emission layer, the layer may be composed of a fluorene compound of the present invention alone, or may further contain an arylamine compound represented by the following formulas [3] to [10].

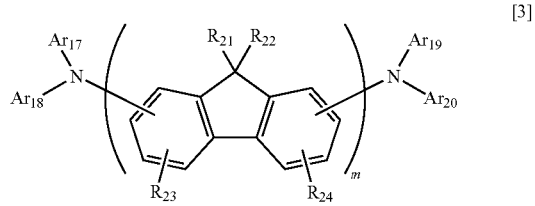

[3]

wherein $R_{21}$ and $R_{22}$ represent a hydrogen atom or a substituted or unsubstituted alkyl group, aralkyl group, aryl group or heterocyclic group, and may be the same or different;

$R_{23}$ and $R_{24}$ represent a hydrogen atom, an alkyl group, an aralkyl group, an aryl group, a heterocyclic group, a cyano group, or a halogen atom, and may be the same or different;

$Ar_{17}$ to $Ar_{20}$ represent a substituted or unsubstituted alkyl group, aralkyl group, aryl group or heterocyclic group, and may be the same or different, and $Ar_{17}$ and $Ar_{18}$, and $Ar_{19}$ and $Ar_{20}$ may be bonded with each other to form a ring; and m is an integer of 1 to 10.

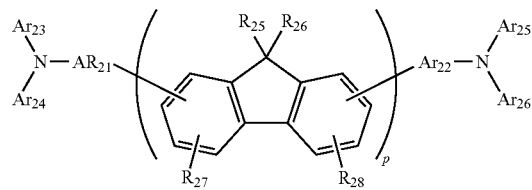

[4]

wherein $R_{25}$ and $R_{26}$ represent a substituted or unsubstituted alkyl group, aralkyl group, aryl group or heterocyclic group, and may be the same or different;

$R_{27}$ and $R_{28}$ represent a hydrogen atom, a substituted or unsubstituted alkyl group, aralkyl group, aryl group, heterocyclic group or cyano group, or a halogen atom, and may be the same or different;

$Ar_{21}$ and $Ar_{22}$ represent a substituted or unsubstituted divalent aryl group or heterocyclic group, and may be the same or different;

$Ar_{23}$ to $Ar_{26}$ represent a substituted or unsubstituted alkyl group, aralkyl group, aryl group or heterocyclic group, and may be the same or different, and $Ar_{23}$ and $Ar_{24}$, and $Ar_{25}$ and $Ar_{26}$ may be bonded with each other to form a ring; and p is an integer of 1 to 10.

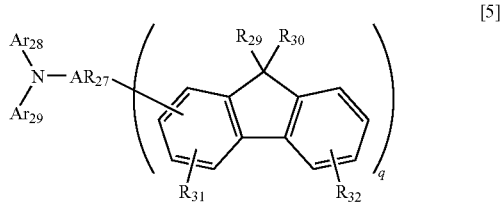

[5]

wherein $R_{29}$ and $R_{30}$ represent a hydrogen atom or a substituted or unsubstituted alkyl group, aralkyl group, aryl group or heterocyclic group, and may be the same or different;

$R_{31}$ and $R_{32}$ represent a hydrogen atom, a substituted or unsubstituted alkyl group, aralkyl group, aryl group, heterocyclic group or cyano group or a halogen atom, and may be the same or different;

$Ar_{27}$ represents a substituted or unsubstituted divalent aryl group or heterocyclic group;

$Ar_{28}$ and $Ar_{29}$ represent a substituted or unsubstituted alkyl group, aralkyl group, aryl group or heterocyclic group, and may be the same or different, and $Ar_{28}$ and $Ar_{29}$ may be bonded with each other to form a ring; and q is an integer of 1 to 10.

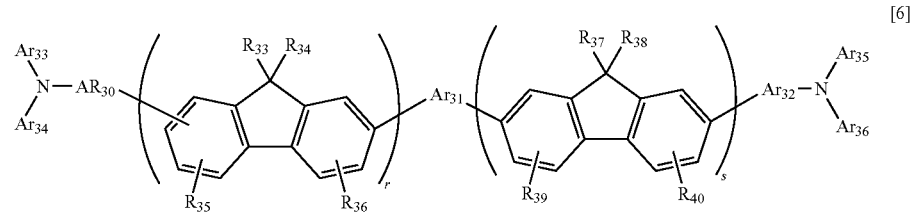

[6]

wherein $R_{33}$, $R_{34}$, $R_{37}$ and $R_{38}$ represent a hydrogen atom or a substituted or unsubstituted alkyl group, aralkyl group, aryl group or heterocyclic group, and may be the same or different;

$R_{35}$, $R_{36}$, $R_{39}$ and $R_{40}$ represent a hydrogen atom, a substituted or unsubstituted alkyl group, aralkyl group, aryl group, heterocyclic group or cyano group, or a halogen atom, and may be the same or different;

$Ar_{30}$ to $Ar_{32}$ represent a substituted or unsubstituted divalent aryl group or heterocyclic group, and may be the same or different, and $Ar_{30}$ and $Ar_{32}$ may be a direct bond, $Ar_{33}$ to $Ar_{36}$ represent a substituted or unsubstituted alkyl group, aralkyl group, aryl group or heterocyclic group, and may be the same or different, and $Ar_{33}$ and $Ar_{34}$, and $Ar_{35}$ and $Ar_{36}$ may be bonded with each other to form a ring; and r and s are an integer of 1 to 10.

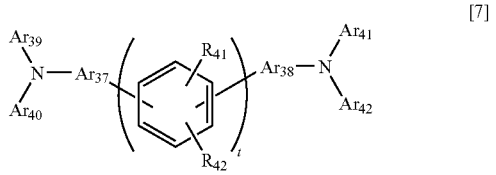

[7]

wherein $R_{41}$ and $R_{42}$ represent a hydrogen atom, a substituted or unsubstituted alkyl group, aralkyl group, aryl group, heterocyclic group or cyano group, or a halogen atom, and may be the same or different;

$Ar_{37}$ and $Ar_{38}$ represent a substituted or unsubstituted divalent aryl group or heterocyclic group, and may be the same or different;

$Ar_{39}$ to $Ar_{42}$ represent a substituted or unsubstituted alkyl group, aralkyl group, aryl group or heterocyclic group, and may be the same or different, and $Ar_{39}$ and $Ar_{40}$, and $Ar_{41}$ and $Ar_{42}$ may be bonded with each other to form a ring; and t is an integer of 1 to 10.

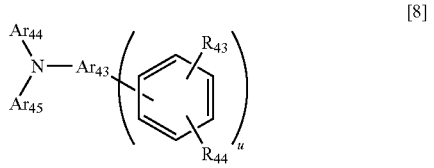

[8]

wherein $R_{43}$ and $R_{44}$ represent a hydrogen atom, a substituted or unsubstituted alkyl group, aralkyl group, aryl group, heterocyclic group or cyano group or a halogen atom, and may be the same or different;

$Ar_{43}$ represents a substituted or unsubstituted divalent aryl group or heterocyclic group, $Ar_{44}$ and $Ar_{45}$ represent a substituted or unsubstituted alkyl group, aralkyl group, aryl group or heterocyclic group, and may be the same or different, and $Ar_{44}$ and $Ar_{45}$ may be bonded with each other to form a ring; and u is an integer of 1 to 10.

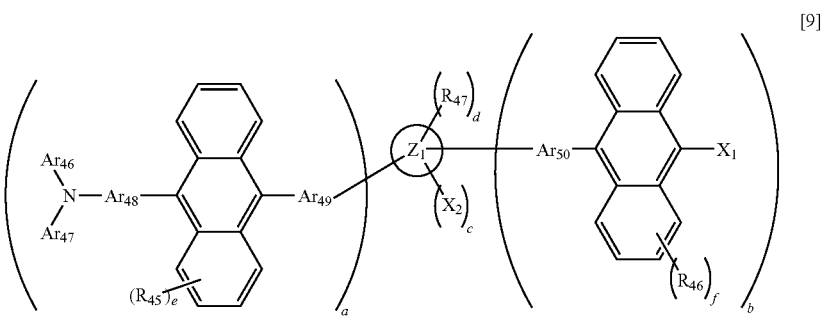

[9]

wherein $Z_1$ represents a molecular unit containing an aromatic ring, a condensed polycyclic ring or a heterocyclic ring;

$Ar_{46}$ and $Ar_{47}$ are selected from the group consisting of a substituted or unsubstituted alkyl group, aralkyl group, aryl group and heterocyclic group, and may be a group bonded through a linking group and may be the same or different, $Ar_{46}$ and $Ar_{47}$ may also be bonded with each other to form a ring, and $Ar_{46}$ and $Ar_{47}$ on different anthryl derivative groups may be the same or different;

$Ar_{48}$ is selected from the group consisting of a direct single bond, a substituted or unsubstituted arylene group and divalent heterocyclic group and a divalent substituent containing a linking group, and may be the same or different;

$Ar_{49}$ and $Ar_{50}$ are selected from the group consisting of a direct single bond and a substituted or unsubstituted alkylene group, alkenylene group, alkynylene group, aralkylene group, arylene group and divalent heterocyclic group, and may be a group bonded through a linking group and may be the same or different;

$X_1$ is selected from the group consisting of a hydrogen atom, a deuterium atom, a halogen atom, a substituted or unsubstituted alkyl group, alkenyl group, alkynyl group, aralkyl group, alkoxy group, sulfide group, aryl group and heterocyclic group, a substituted silyl group and a boranyl group, and may be a group bonded through a linking group and may be the same or different;

$X_2$ is selected from the group consisting of a substituted or unsubstituted aryl group and heterocyclic group, and may be a group bonded through a linking group and may be the same or different;

$R_{45}$ and $R_{46}$ are selected from the group consisting of a hydrogen atom, a deuterium atom, a halogen atom and a substituted or unsubstituted alkyl group, aryl group, alkoxy group and amino group, and may be the same or different;

$R_{47}$ is selected from the group consisting of a hydrogen atom, a deuterium atom, a halogen atom and a substituted or unsubstituted alkyl group and alkoxy group, and may be the same or different; and a is an integer of 0 to 6, b+c+d=6−a, with the proviso that a+b is an integer of 2 or more, and when a=0, at least one $X_1$ on an anthryl group contains a substituent other than a hydrogen atom, a deuterium atom or a halogen atom, and e and f are an integer of 1 to 8.

[10]

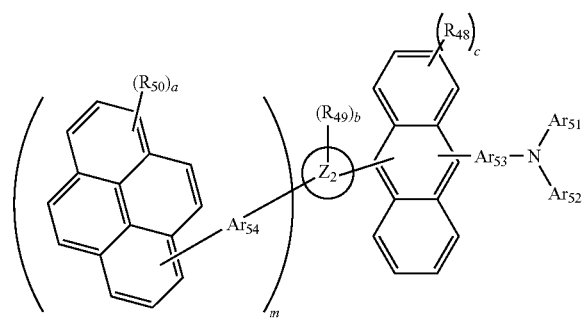

wherein $Ar_{51}$ and $Ar_{52}$ are selected from the group consisting of a substituted or unsubstituted alkyl group, aralkyl group, aryl group and heterocyclic group, and may be a group bonded through a linking group and may be the same or different, and $Ar_{51}$ and $Ar_{52}$ may be bonded with each other to form a ring;

$Z_2$ is selected from the group consisting of a direct single bond and a substituted or unsubstituted alkylene group, alkenylene group, alkynylene group, aralkylene group, arylene group and divalent heterocyclic group, and may be a group bonded through a linking group, $Ar_{53}$ is selected from the group consisting of a direct single bond, and a substituted or unsubstituted arylene group and divalent heterocyclic group, and may be a group bonded through a linking group, $Ar_{54}$ is selected from the group consisting of a direct single bond, and a substituted or unsubstituted alkylene group, alkenylene group, alkynylene group, aralkylene group, arylene group and divalent heterocyclic group, and may be a group bonded through a linking group;

$R_{48}$ to $R_{50}$ are selected from the group consisting of a hydrogen atom, a deuterium atom, a halogen atom and a substituted or unsubstituted alkyl group, aryl group, alkoxy group and amino group, and may be the same or different; and a is an integer of 1 to 9, b is an integer of 1 to 4, c is an integer of 1 to 8 and m is an integer of 1 to 3.

In the case of using the arylamine compound represented by the above-described formulas [2] to [9] as a dopant material, the concentration of the dopant in the host material is 0.01 wt % to 80 wt %, preferably 1 wt % to 40 wt %. The dopant material may be contained in the entire layer of a host material uniformly or with a concentration gradient, or contained in some region and the host material layer may have a region containing no dopant material.

Specific examples of substituents in the above-described formulas [3] to [10] are the same as those described in the case of the formulas [1] and [2].

Examples of substituted or unsubstituted alkyl groups in the above-described formulas [9] and [10] include, but are obviously not limited to, a methyl group, methyl-d1 group, methyl-d3 group, ethyl group, ethyl-d5 group, n-propyl group, n-butyl group, n-pentyl group, n-hexyl group, n-heptyl group, n-octyl group, n-decyl group, iso-propyl group, iso-propyl-d7 group, iso-butyl group, sec-butyl group, tert-butyl group, tert-butyl-d9 group, iso-pentyl group, neopentyl group, tert-octyl group, fluoromethyl group, difluoromethyl group, trifluoromethyl group, 2-fluoroethyl group, 2,2,2-trifluoroethyl group, perfluoroethyl group, 3-fluoropropyl group, perfluoropropyl group, 4-fluorobutyl group, perfluorobutyl group, 5-fluoropentyl group, 6-fluorohexyl group, chloromethyl group, trichloromethyl group, 2-chloroethyl group, 2,2,2-trichloroethyl group, 4-chlorobutyl group, 5-chloropentyl group, 6-chlorohexyl group, bromomethyl group, 2-bromoethyl group, iodomethyl group, 2-iodoethyl group, hydroxymethyl group, hydroxyethyl group, cyclopropyl group, cyclobutyl group, cyclopentyl group, cyclohexyl group, cyclopentylmethyl group, cyclohexylmethyl group, cyclohexylethyl group, 4-fluorocyclohexyl group, norbornyl group, and adamantyl group.

Examples of substituted or unsubstituted aralkyl groups include, but are obviously not limited to, a benzyl group, a 2-phenylethyl group, a 2-phenylisopropyl group, a 1-naphtylmethyl group, a 2-naphthylmethyl group, a 2-(1-naphthyl) ethyl group, a 2-(2-naphthyl)ethyl group, a 9-anthrylmethyl group, a 2-(9-anthryl)ethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group and a 4-bromobenzyl group.

Examples of substituted or unsubstituted alkenyl groups include, but are obviously not limited to, a vinyl group, an allyl group (2-propenyl group), a 1-propenyl group, an isopropenyl group, a 1-butenyl group, a 2-butenyl group, a 3-butenyl group and a styryl group.

Examples of substituted or unsubstituted alkynyl groups include, but are obviously not limited to, an acetylenyl group, a phenylacetylenyl group and a 1-propynyl group.

Examples of substituted or unsubstituted aryl groups include, but are obviously not limited to, a phenyl group, phenyl-d5 group, 4-methylphenyl group, 4-methoxyphenyl group, 4-ethylphenyl group, 4-fluorophenyl group, 4-trifluorophenyl group, 3,5-dimethylphenyl group, 2,6-diethylphenyl group, mesityl group, 4-tert-butylphenyl group, ditolylaminophenyl group, biphenyl group, terphenyl group, naphthyl group, naphthyl-d7 group, acenaphthylenyl group, anthryl group, anthryl-d9 group, phenanthryl group, phenanthryl-d9 group, pyrenyl group, pyrenyl-d9 group, acephenanthrylenyl group, aceanthrylenyl group, chrysenyl group, dibenzochrysenyl group, benzoanthryl group, benzoanthryl-d11 group, dibenzoanthryl group, naphthacenyl group, picenyl group, pentacenyl group, fluorenyl group, triphenylenyl group, perylenyl group, and perylenyl-d-11 group.

Examples of substituted or unsubstituted heterocyclic groups include, but are obviously not limited to, a pyrrolyl group, pyridyl group, pyridyl-d5 group, bipyridyl group, methylpyridyl group, pyrimidinyl group, pyrazinyl group, pyridazinyl group, terpyrrolyl group, thienyl group, thienyl-d4 group, terthienyl group, propylthienyl group, benzothienyl group, dibenzothienyl group, dibenzothienyl-d7 group, furyl group, furyl-d4 group, benzofuryl group, isobenzofuryl group, dibenzofuryl group, dibenzofuryl-d7 group, quinolyl group, quinolyl-d6 group, isoquinolyl group, quinoxalinyl group, naphthylidinyl group, quinazolinyl group, phenanthridinyl group, indolizinyl group, phenazinyl group, carbazolyl group, oxazolyl group, oxadiazolyl group, thiazolyl group, thiadiazolyl group, acrydinyl group, and phenazinyl group.

Examples of substituted or unsubstituted aralkylene groups include, but are obviously not limited to, a benzylene group, a 2-phenylethylene group, a 2-phenylisopropylene group, a 1-naphthylmethylene group, a 2-naphthylmethylene group, a 9-anthrylmethylene group, a 2-fluorobenzylene group, a 3-fluorobenzylene group, a 4-fluorobenzylene group, a 4-chlorobenzyl group and a 4-bromobenzyl group.

Examples of substituted or unsubstituted alkenylene groups include, but are obviously not limited to, a vinylene group, an iso-propenylene group, a styrylene group and a 1,2-diphenylvinylene group.

Examples of substituted or unsubstituted alkynylene groups include, but are obviously not limited to, an acetylenylene group and phenylacetylenylene group.

Examples of substituted or unsubstituted arylene groups include, but are obviously not limited to, a phenylene group, a biphenylene group, a tetrafluorophenylene group, a dimethylphenylene group, a naphthylene group, a phenanthrylene group, a pyrenylene group, a tetracenylene group, a pentacenylene group and a perylenylene group.

Examples of substituted or unsubstituted divalent heterocyclic group include, but are obviously not limited to, a furylene group, a pyrrolylene group, a pyridylene group, a terpyridylene group, a thienylene group, a terthienylene group, an oxazolylene group, a thiazolylene group and a carbazolylene group.

Examples of substituted or unsubstituted amino group (—NR'R") include, but are obviously not limited to, those in which R' and R" represent a hydrogen atom; a deuterium atom; the above-described substituted or unsubstituted alkyl group, aralkyl group, aryl group or heterocyclic group; an alkyl group, alkenyl group, alkynyl group, aralkyl group or amino group linked by a substituted or unsubstituted arylene group or divalent heterocyclic group, a substituted silyl group, an ether group, a thioether group or a carbonyl group, such as an amino group, N-methylamino group, N-ethylamino group, N,N-dimethylamino group, N,N-diethylamino group, N-methyl-N-ethylamino group, N-benzylamino group, N-methyl-N-benzylamino group, N,N-dibenzylamino group, anilino group, N,N-diphenylamino group, N-phenyl-N-tolylamino group, N,N-ditolylamino group, N-methyl-N-phenylamino group, N,N-dianisolylamino group, N-mesityl-N-phenylamino group, N,N-dimesitylamino group, N-phenyl-N-(4-tert-butylphenyl)amino group, and N-phenyl-N-(4-trifluoromethylphenyl)amino group.

Examples of substituted or unsubstituted alkoxy groups include, but are obviously not limited to, alkyloxy groups and aralkyloxy groups containing the above-described substituted or unsubstituted alkyl group or aralkyl group; and aryloxy groups containing the above-described substituted or unsubstituted aryl group or heterocyclic group, such as a methoxy group, an ethoxy group, a propoxy group, a 2-ethyloctyloxy group, a phenoxy group, 4-tert-butylphenoxy group, a benzyloxy group and a thienyloxy group.

Examples of substituted or unsubstituted sulfide groups include, but are obviously not limited to, alkyl sulfide groups and aralkyl sulfide groups containing the above-described substituted or unsubstituted alkyl group or aralkyl group; and aryl sulfide groups containing the above-described substituted or unsubstituted aryl group or heterocyclic group, such as a methyl sulfide group, an ethyl sulfide group, a phenyl sulfide group and a 4-methylphenyl sulfide group.

Examples of linking groups for linking the above-described substitutents include, but are obviously not limited to, the above-described substituted or unsubstituted arylene group, divalent heterocyclic group, alkylene group, alkenylene group, alkynylene group and aralkylene group, a substituted silyl group, an ether group, a thioether group and a carbonyl group.

Examples of substituents that the above-described substituents and linking groups may have include a deuterium atom; alkyl groups and aralkyl groups such as a methyl group, an ethyl group, a n-propyl group, a n-butyl group, a n-penthyl group, a n-hexyl group, a n-heptyl group, a n-octyl group, a n-decyl group, an iso-propyl group, an iso-butyl group, a sec-butyl group, a tert-butyl group, an iso-pentyl group, a neo-pentyl group, a tert-octyl group, a benzyl group and a 2-phenylethyl group; alkoxy groups such as a methoxy group, an ethoxy group, a propoxy group, a 2-ethyl-octyloxy group, a phenoxy group, a 4-tert-butylphenoxy group and a benzyloxy group; aryl groups such as a phenyl group, a 4-methylphenyl group, a 4-ethylphenyl group, a 3-chlorophenyl group, a 3,5-dimethylphenyl group, a triphenylamino group, a biphenyl group, a terphenyl group, a naphthyl group, an anthryl group, a phenanthryl group and a pyrenyl group; heterocyclic groups such as a pyridyl group, a bipyridyl group, a methylpyridyl group, a thienyl group, a terthienyl group, a propylthienyl group, a furyl group, a quinolyl group, a carbazolyl group and N-ethyl carbazolyl group; a halogen; a hydroxyl group; a cyano group; and a nitro group, but are obviously not limited thereto.

Typical examples of arylamine compounds represented by the above-described formula [3] are listed below, but the present invention is not limited thereto.

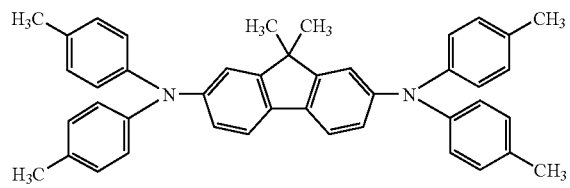

B-1

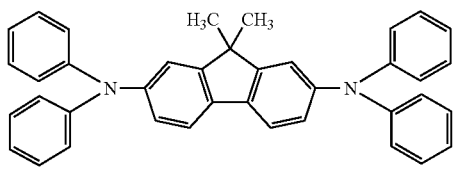

B-2

-continued
B-3
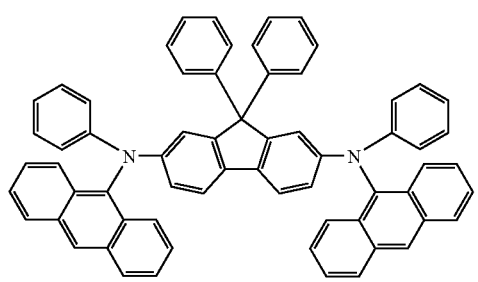
B-4
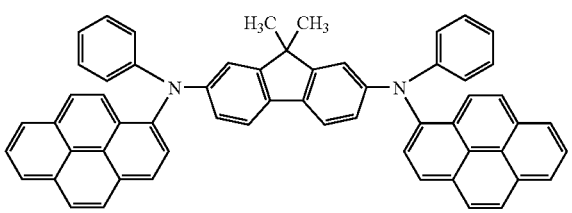
B-5
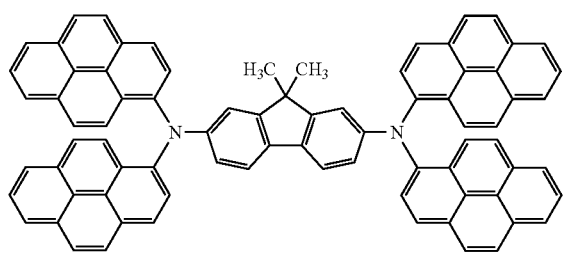
B-6
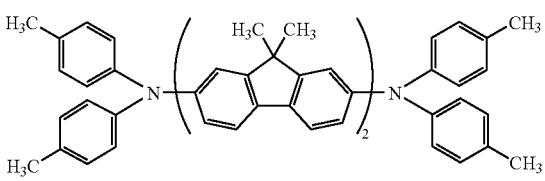
B-7
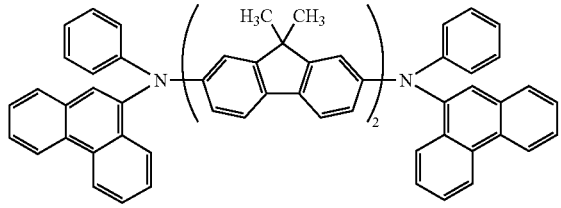
B-8
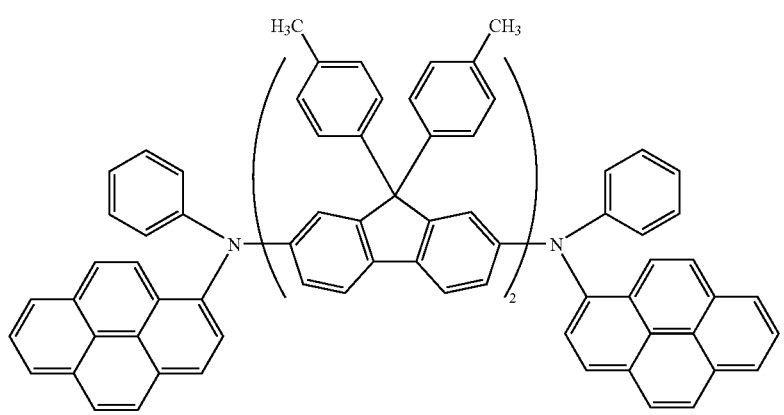
B-9
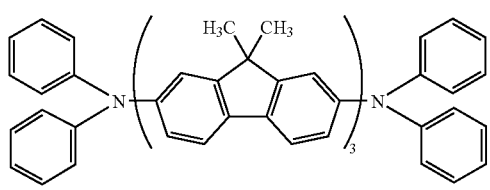
B-10
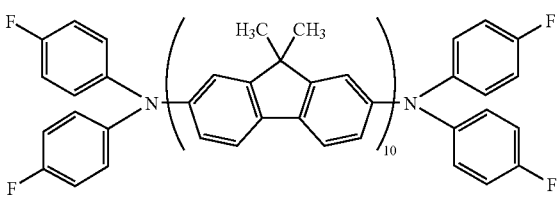

-continued
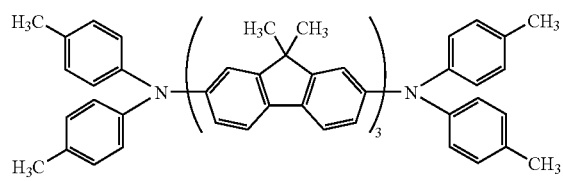
B-11
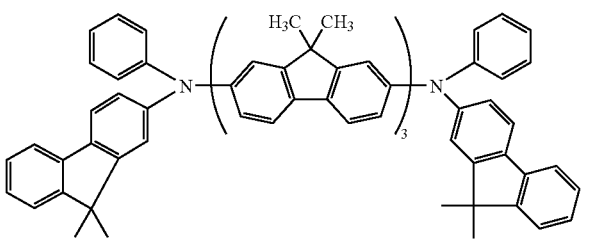
B-12
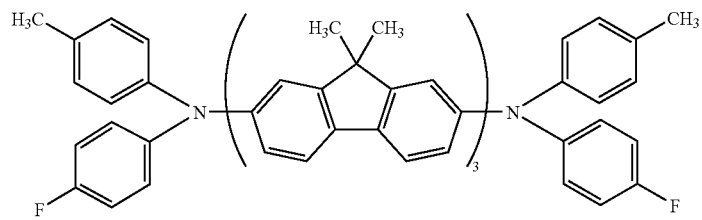
B-13
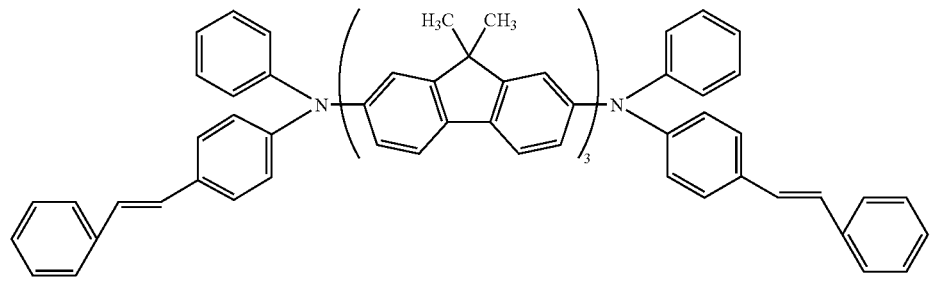
B-14
Typical examples of arylamine compounds represented by the above-described formula [7] are listed below, but the present invention is not limited thereto.
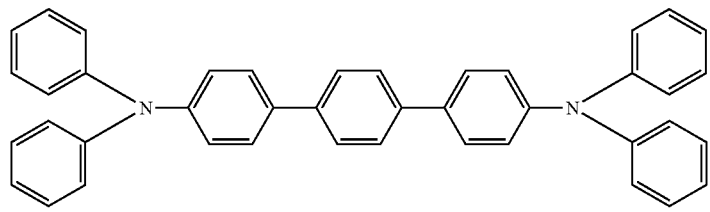
F-1
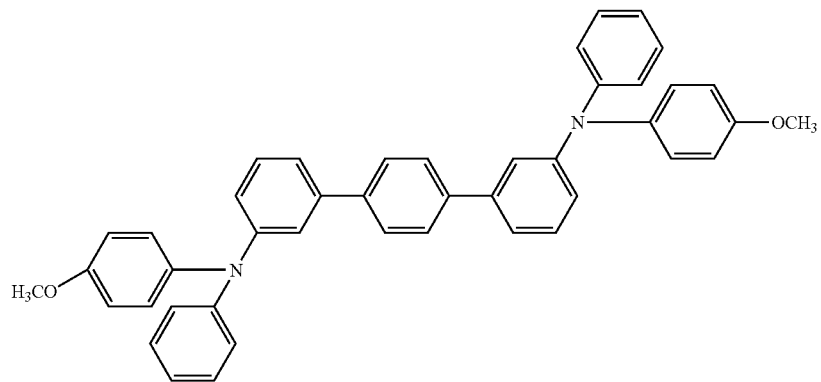
F-2

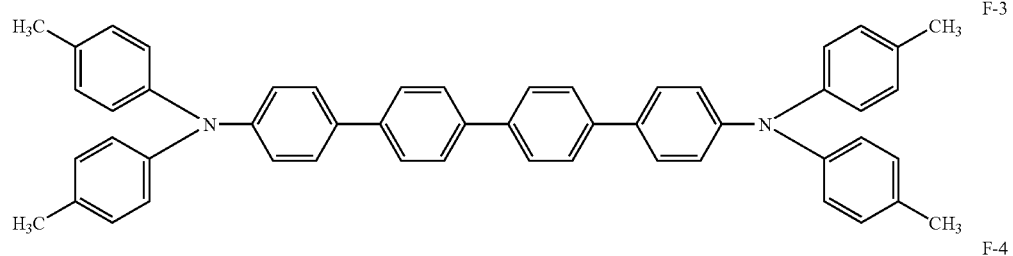
F-3
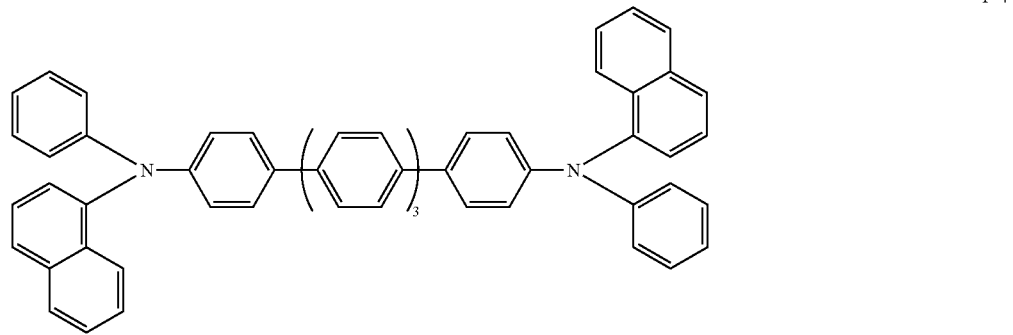
F-4
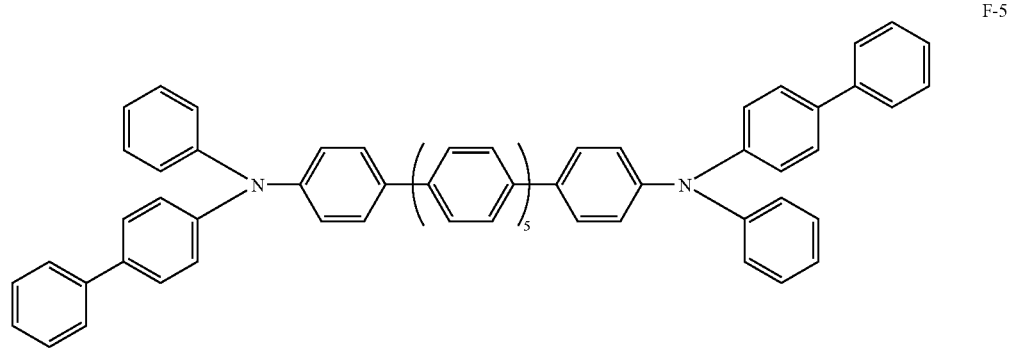
F-5
Typical examples of arylamine compounds represented by the above-described formula [8] are listed below, but the present invention is not limited thereto.
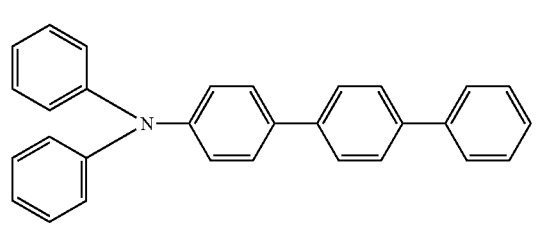
G-1
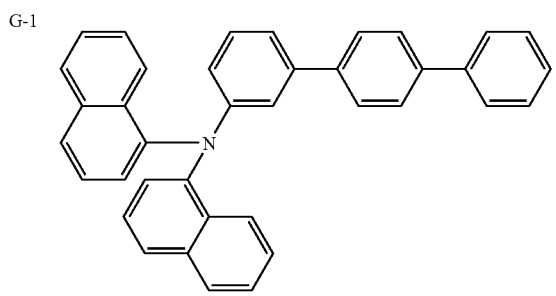
G-2
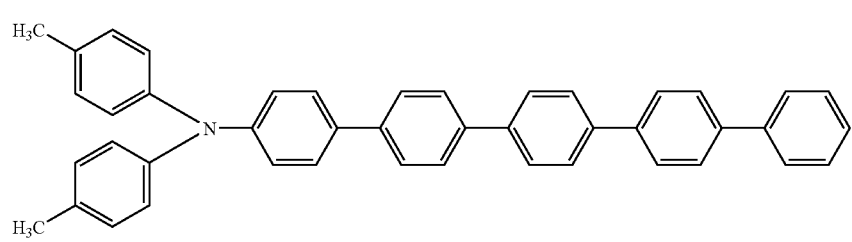
G-3

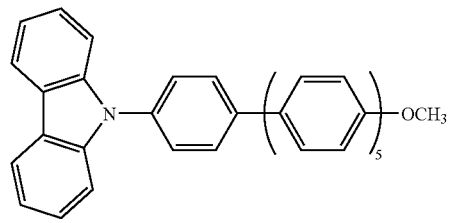
G-4
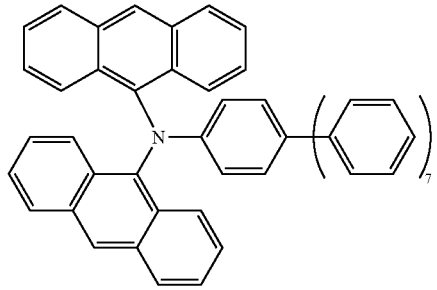
G-5
Typical examples of arylamine compounds represented by the above-described formula [9] are listed below, but the present invention is not limited thereto.
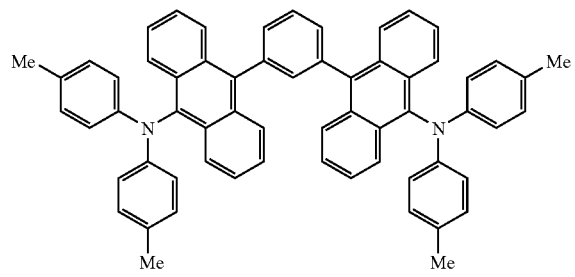
H-1
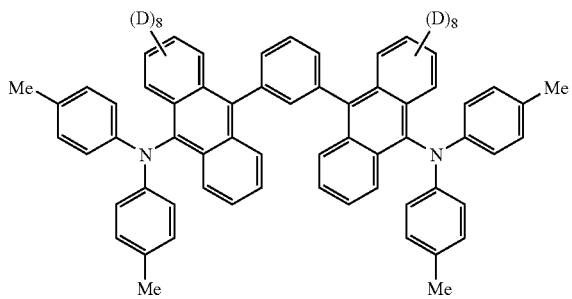
H-2
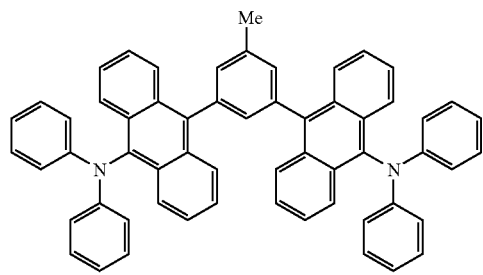
H-3
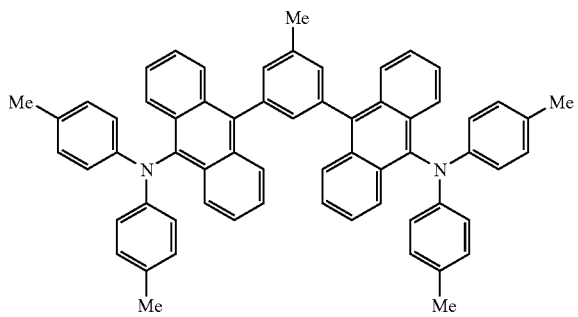
H-4
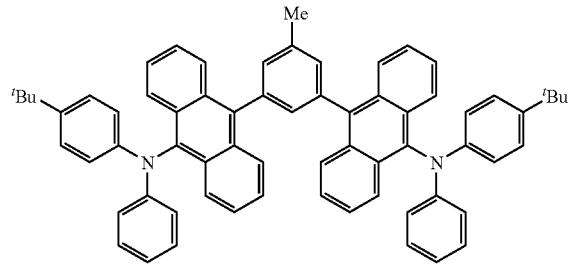
H-5
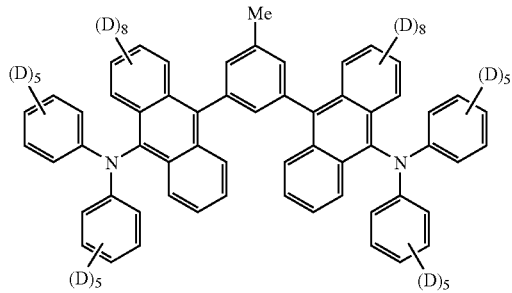
H-6

-continued
H-7
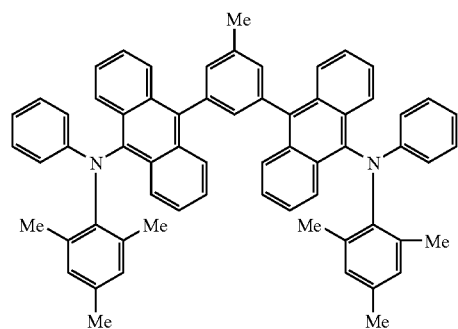
H-8
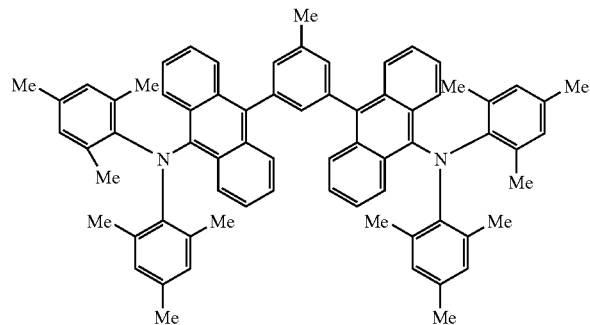
H-9
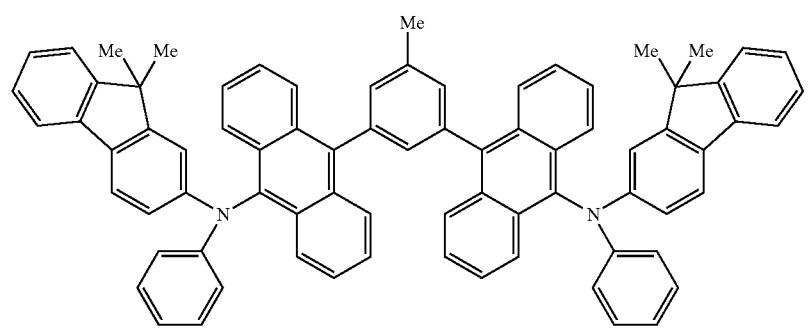
H-10
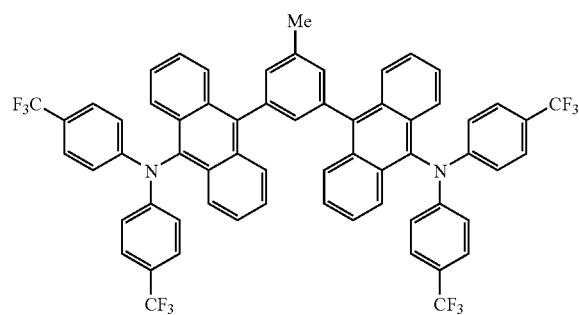
H-11
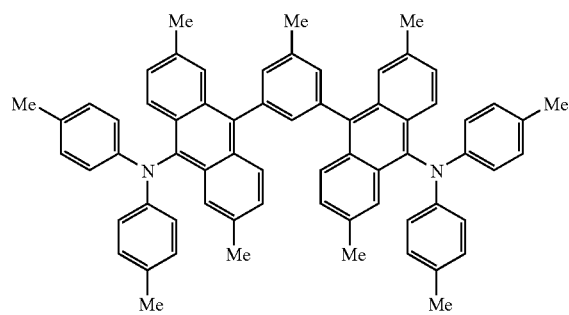
H-12
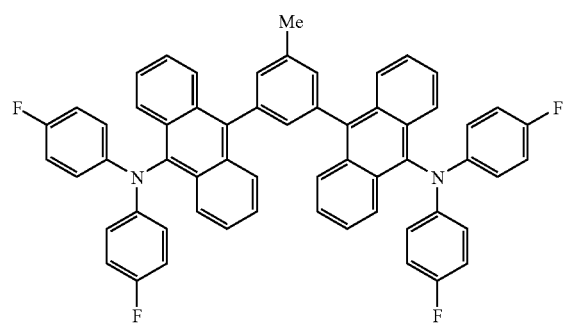
H-13
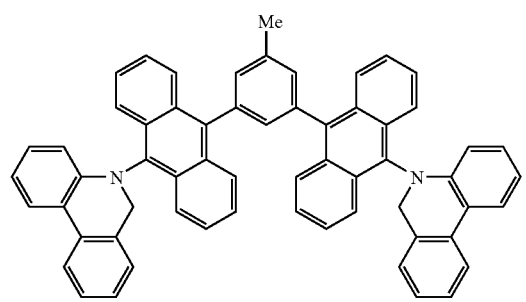

-continued
H-14
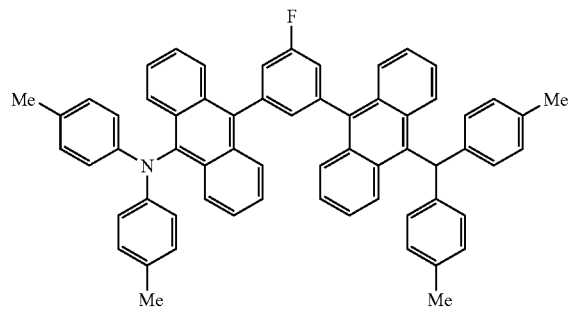
H-15
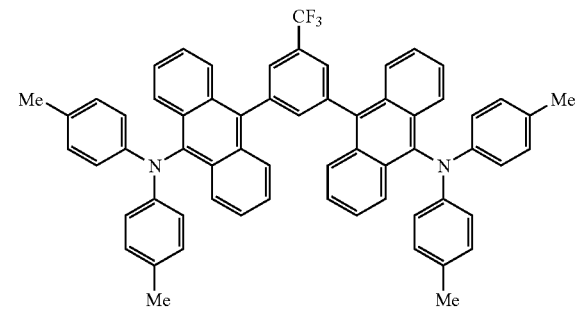
H-16
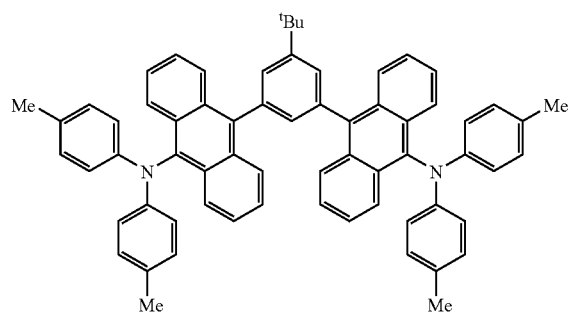
H-17
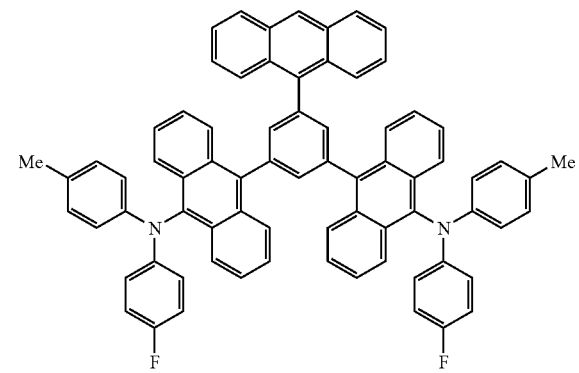
H-18
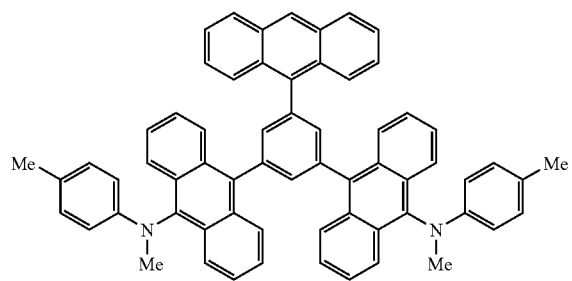
H-19
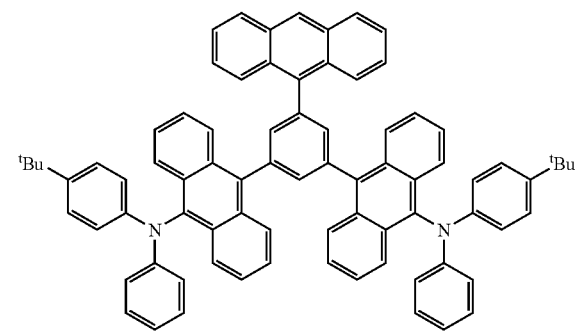
H-20
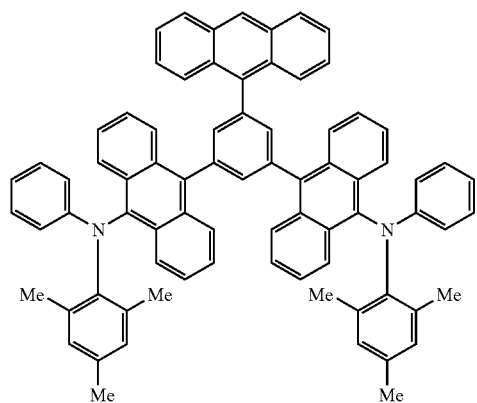
H-21
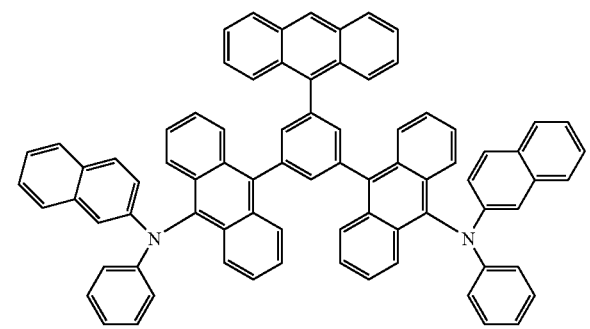

-continued
H-22
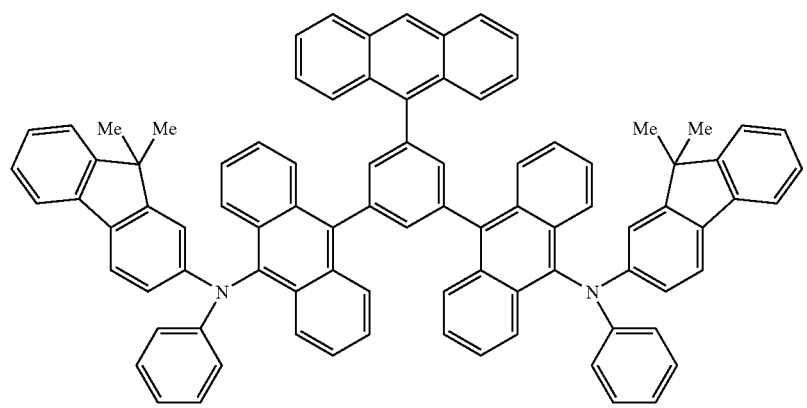
H-23
H-24
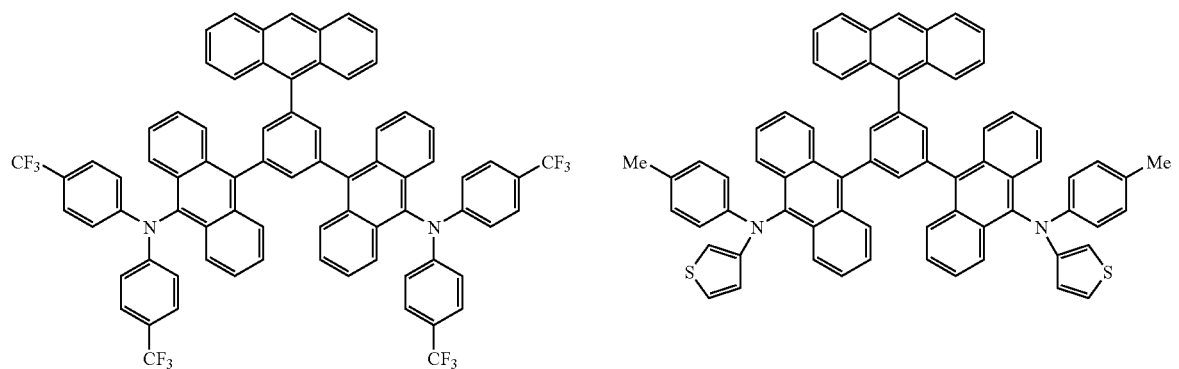
H-25
H-26
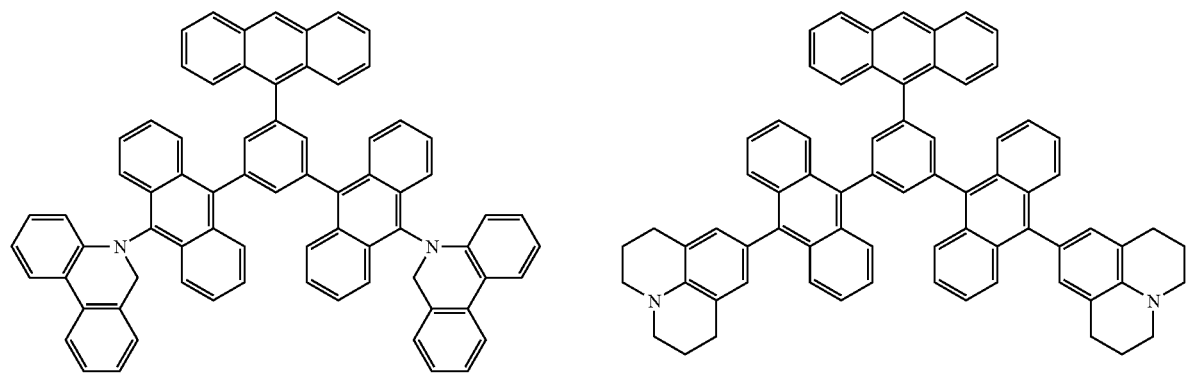
H-27
H-28
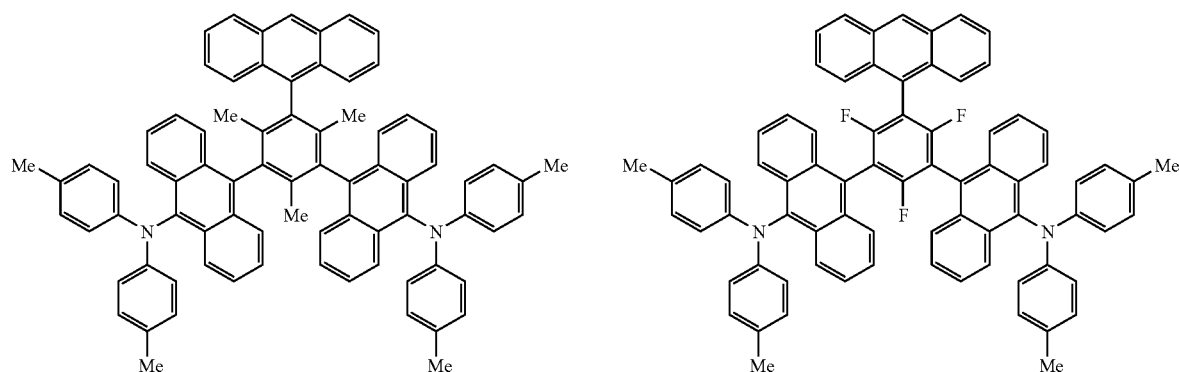

-continued
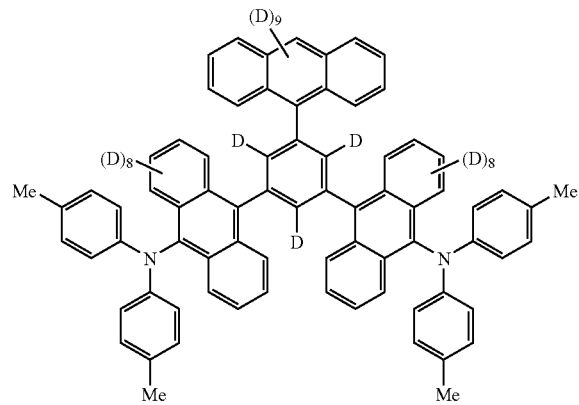
H-29
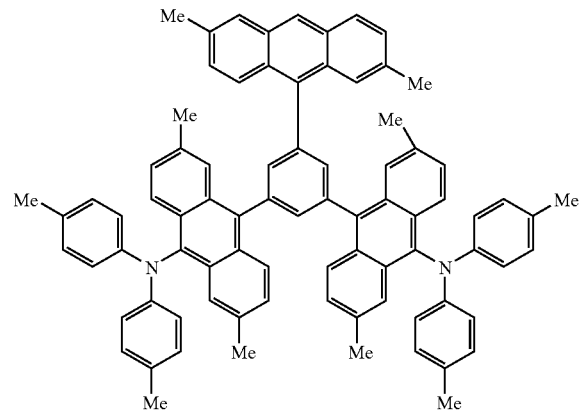
H-30
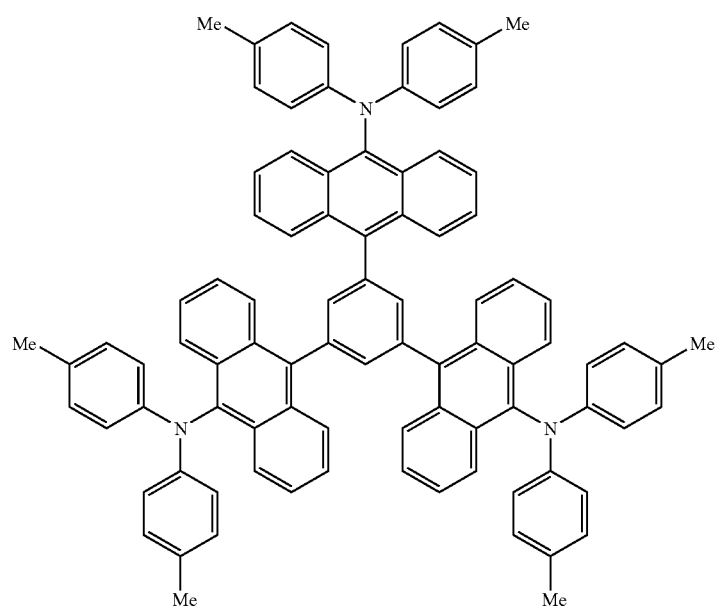
H-31

H-32
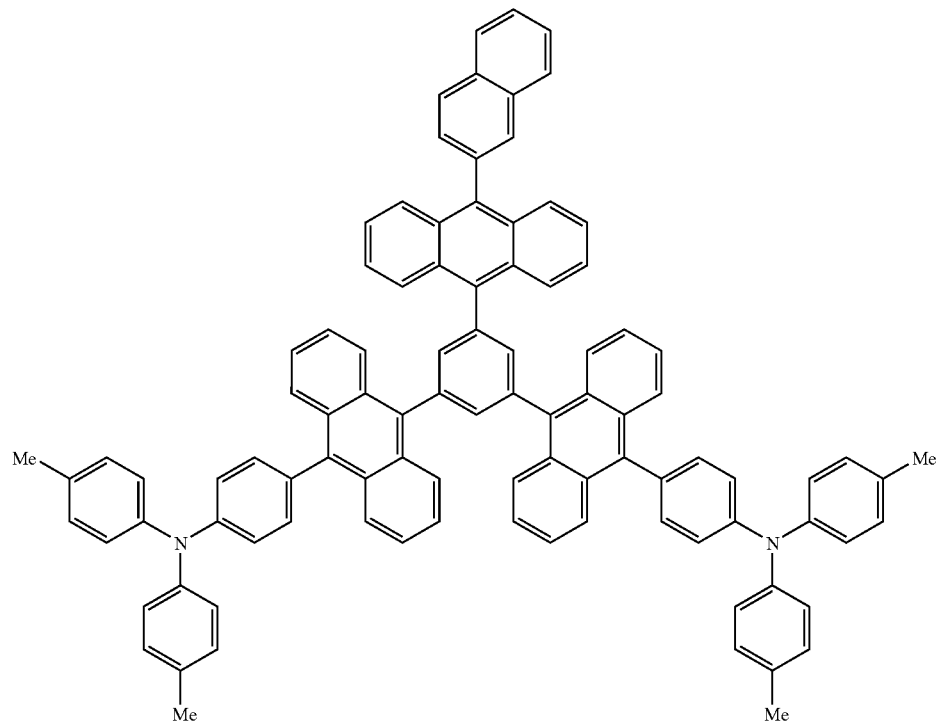
H-33
H-34
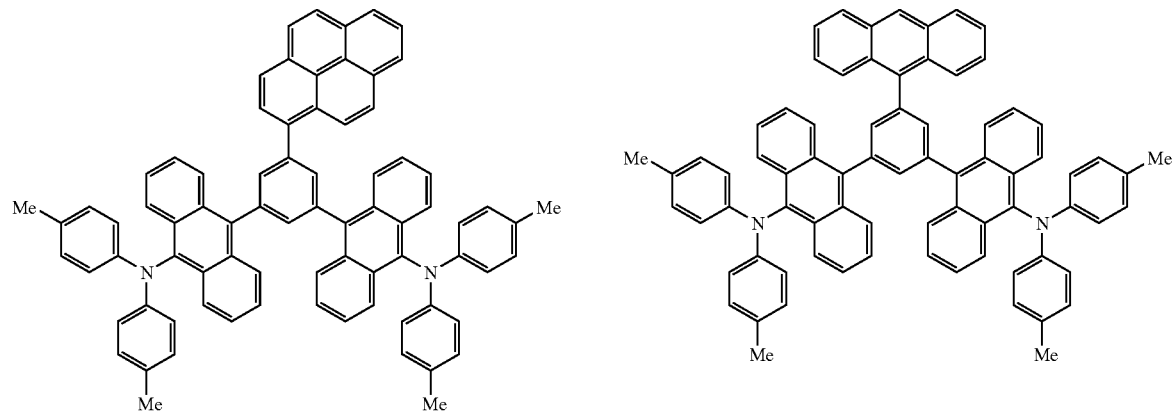
H-35
H-36
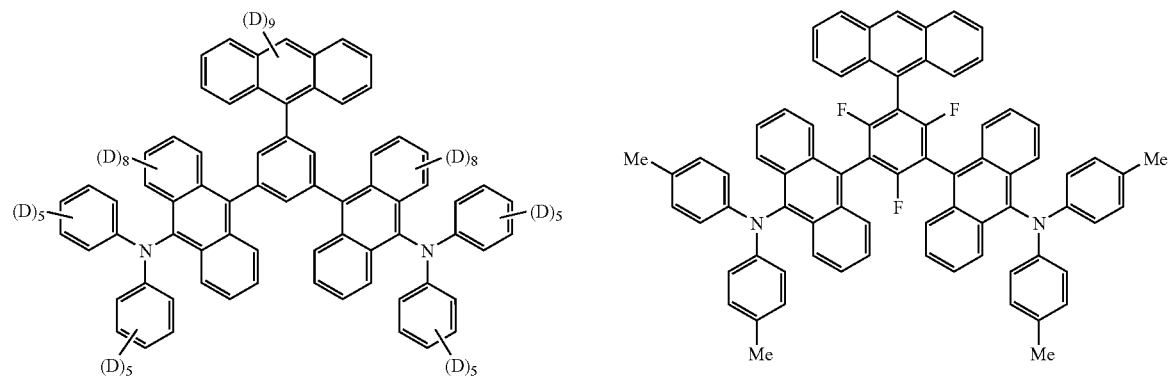

H-37
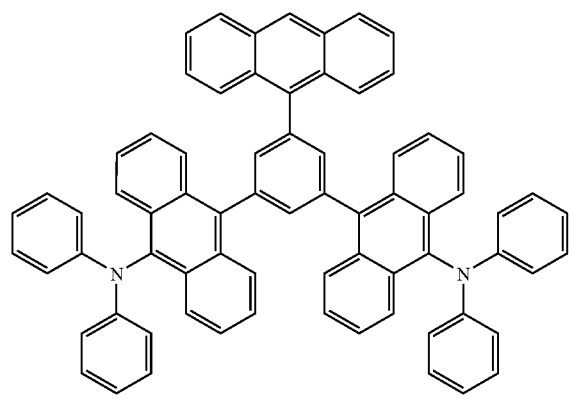
H-38
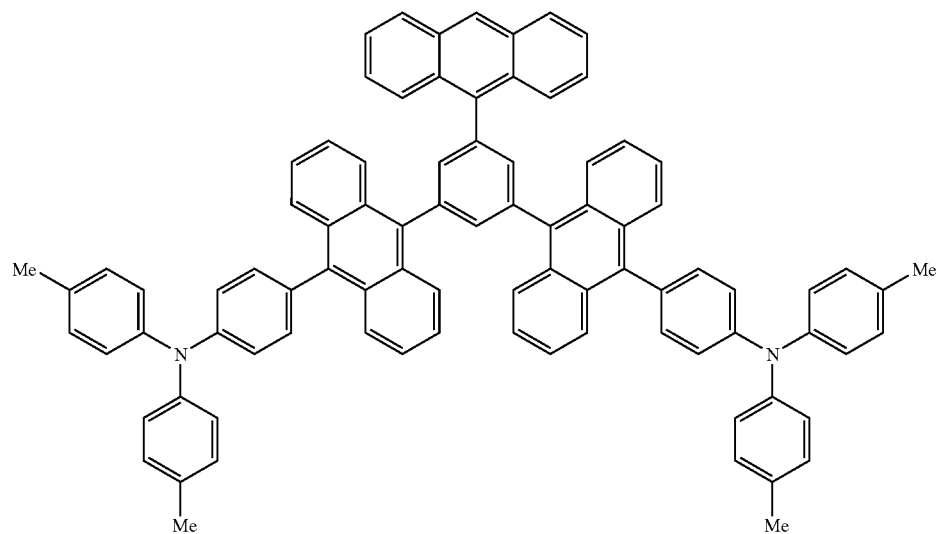
H-39
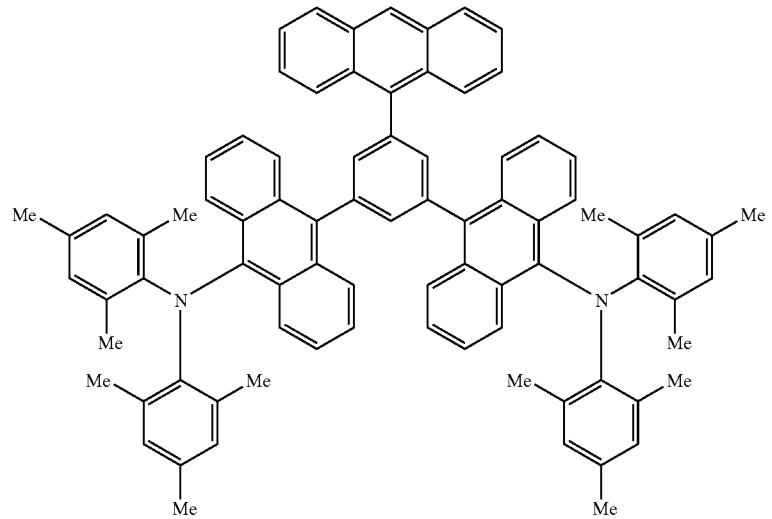

-continued
H-40
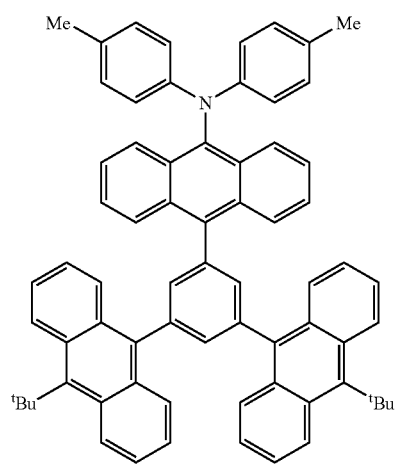
H-41
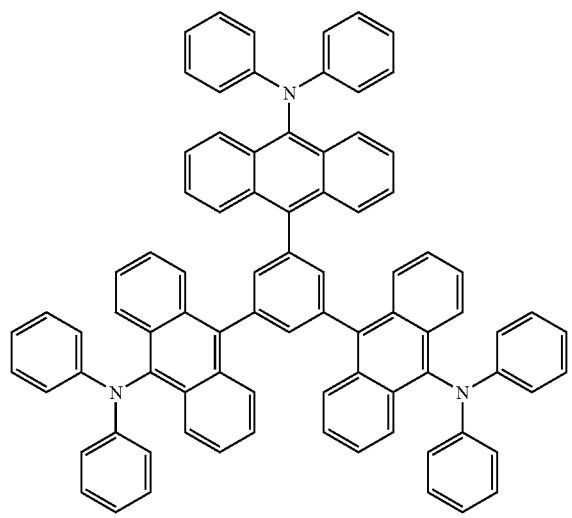
H-42
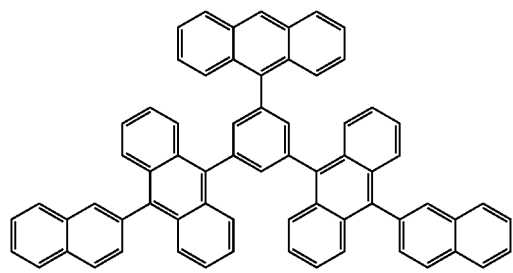
H-43
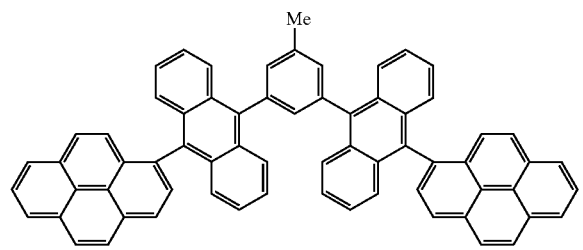
H-44
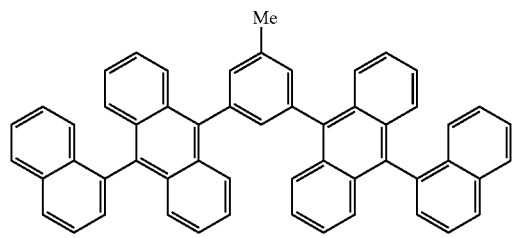
H-45
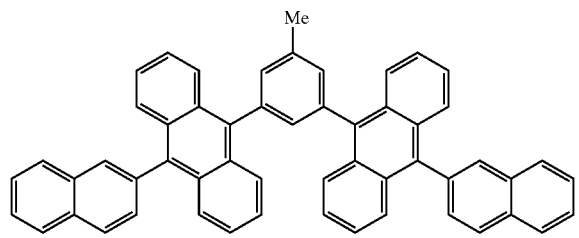
H-46
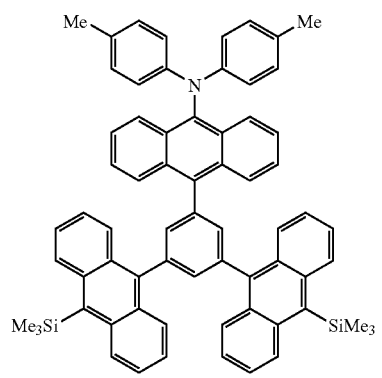
H-47
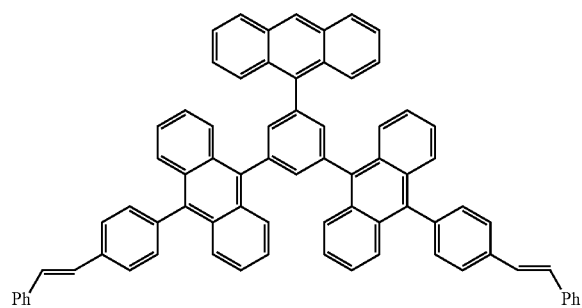

-continued
H-48
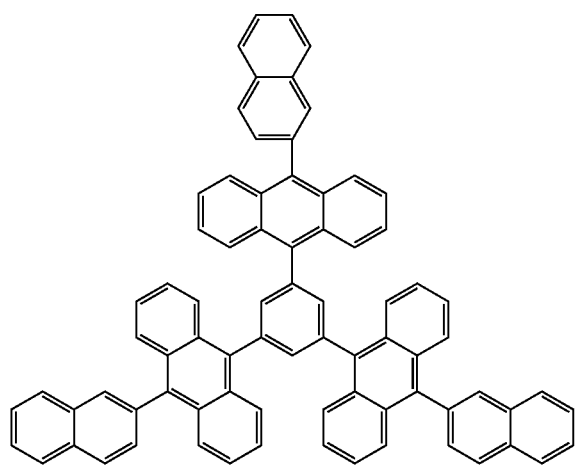
H-49
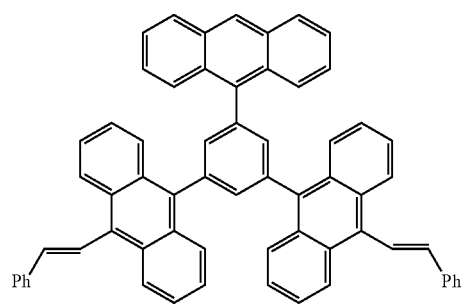
H-52
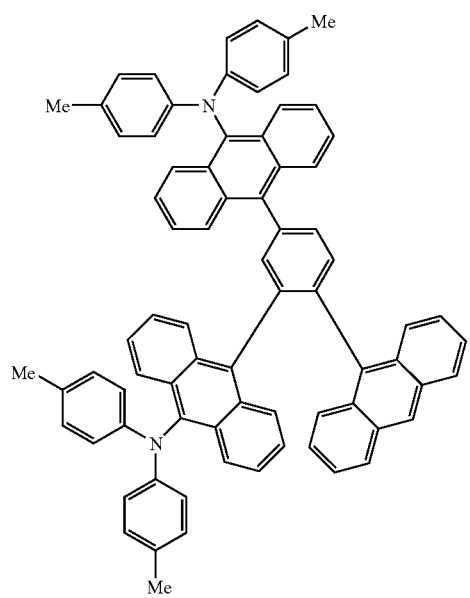
H-53
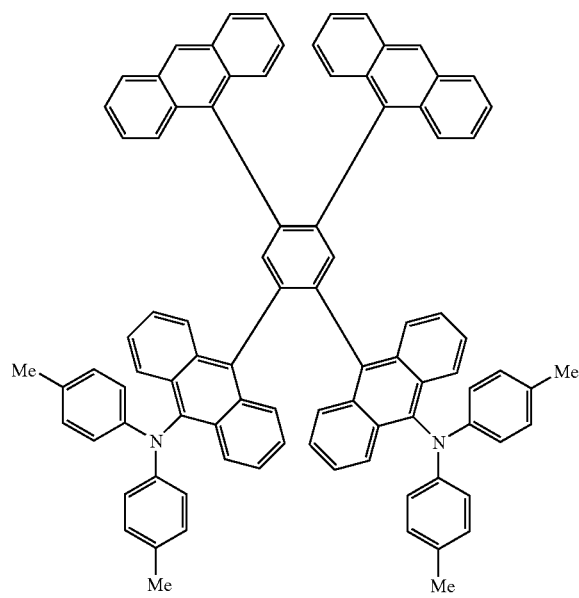
H-54
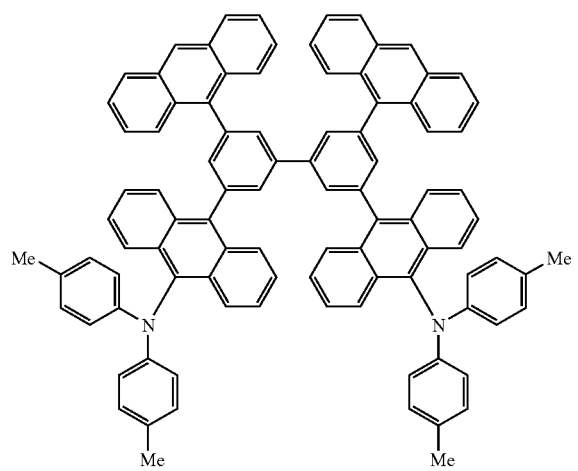
H-55
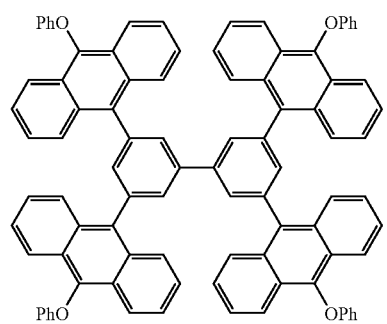

H-56
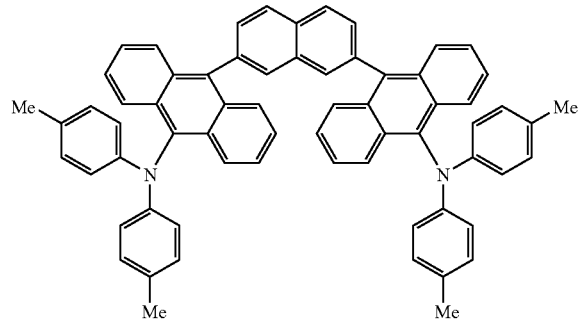
H-57
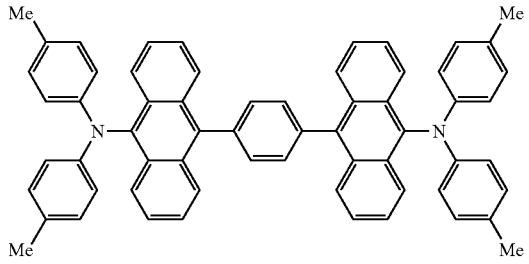
H-58
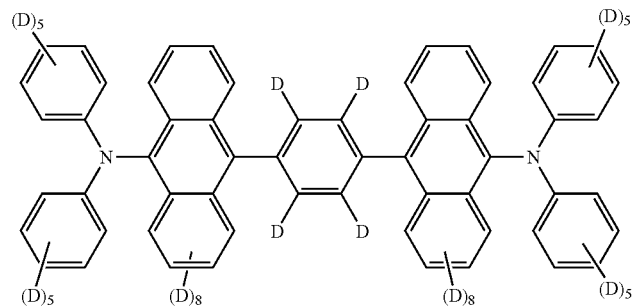
H-59
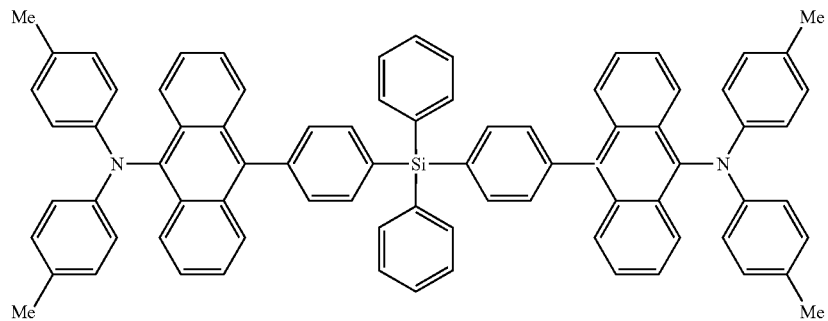
H-60
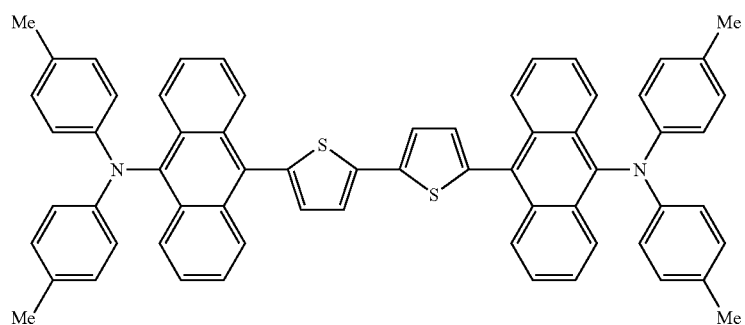

Typical examples of arylamine compounds represented by the above-described formula [10] are listed below, but the present invention is not limited thereto.
I-1
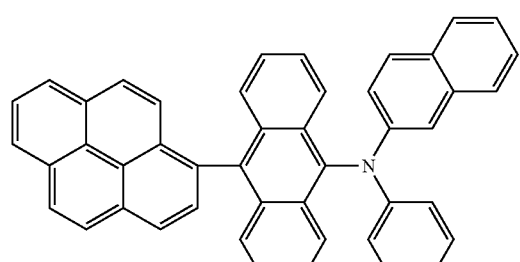
I-2
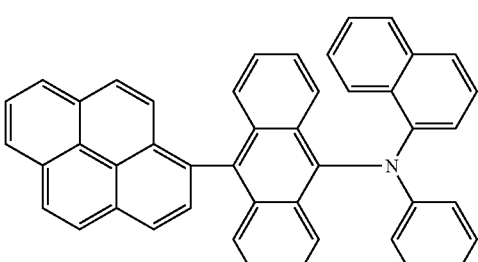
I-3
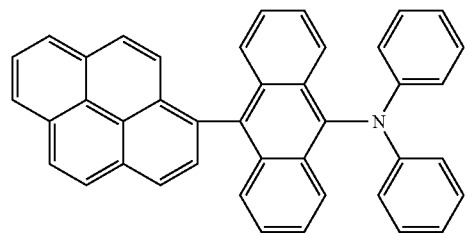
I-4
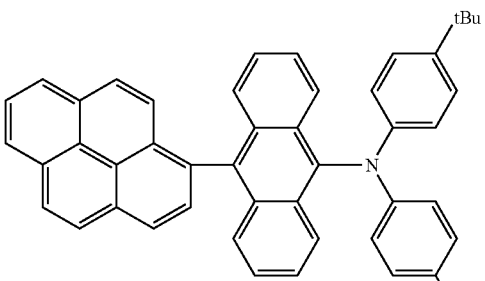
I-5
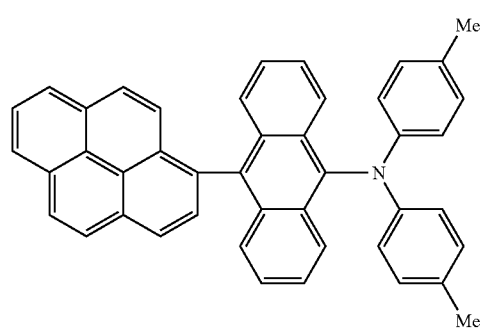
I-6
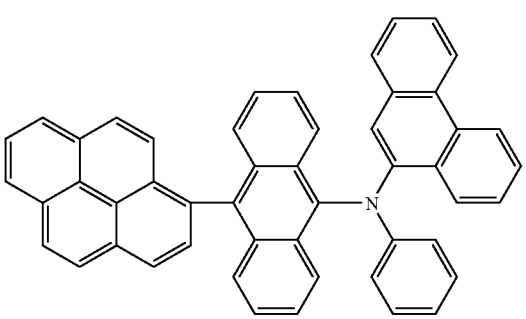
I-7
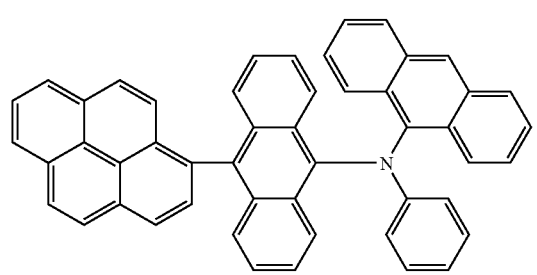
I-8
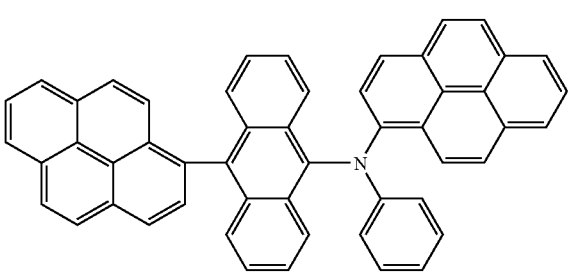
I-9
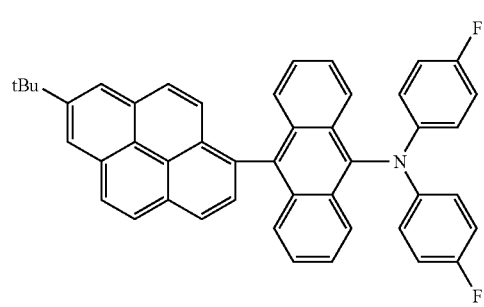
I-10
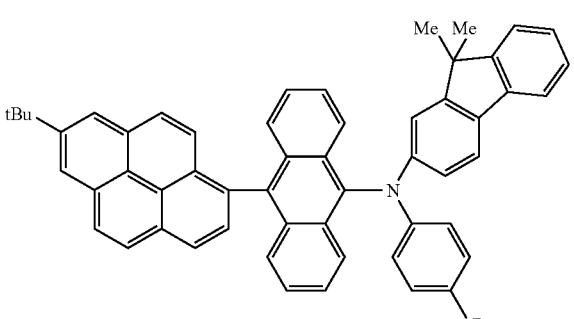

-continued
I-11
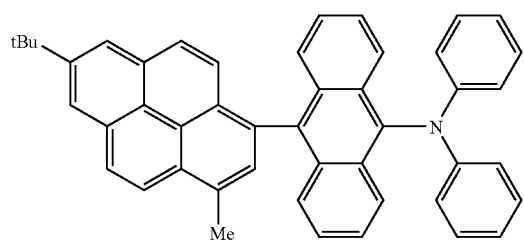
I-12
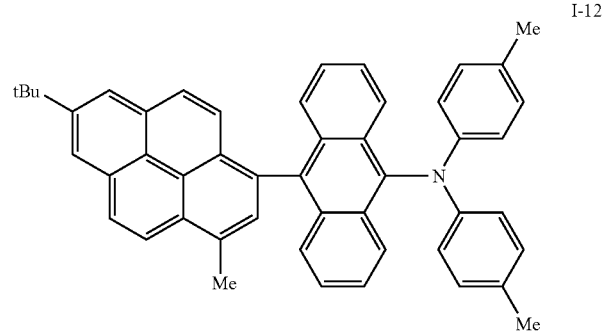
I-13
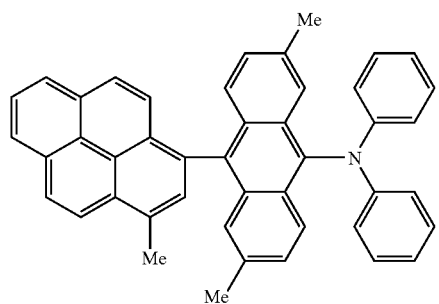
I-14
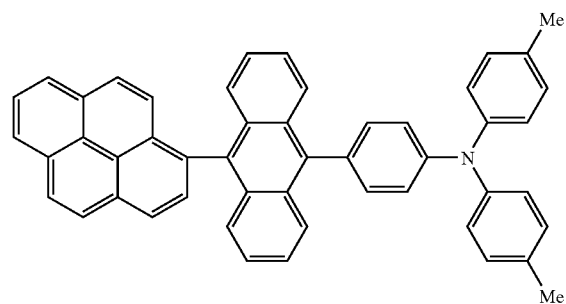
I-15
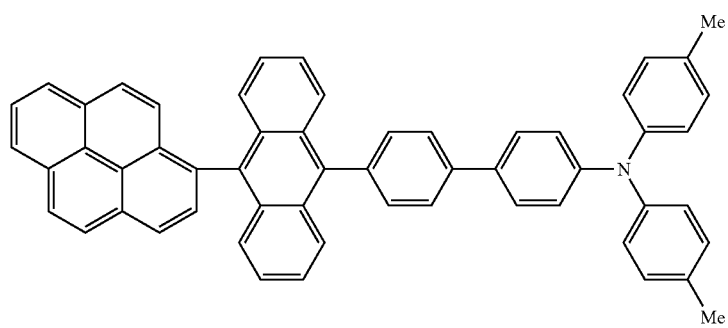
I-16
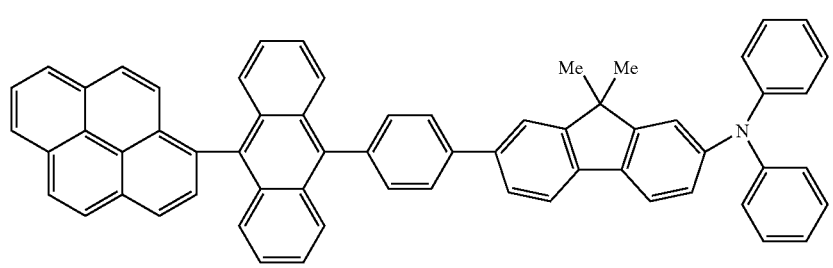
I-17
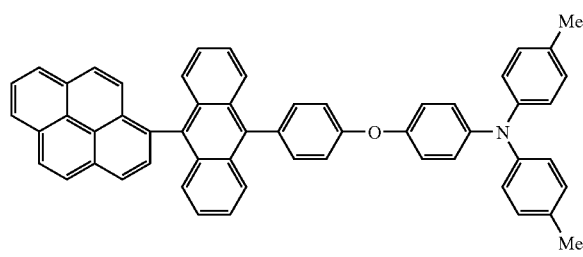
I-18
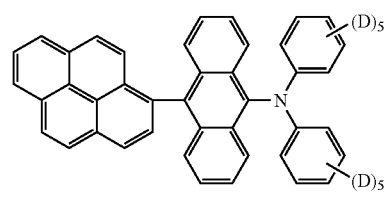

-continued
I-19
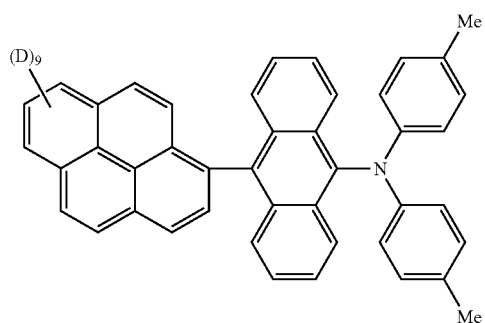
I-20
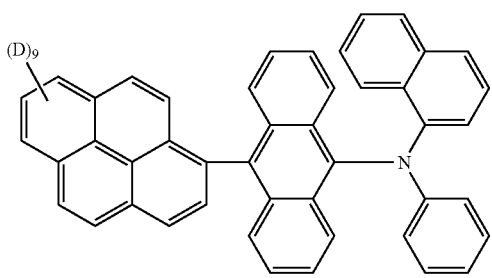
I-21
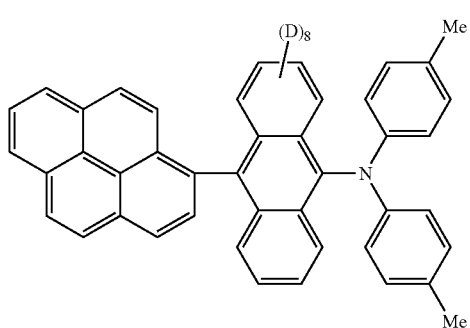
I-22
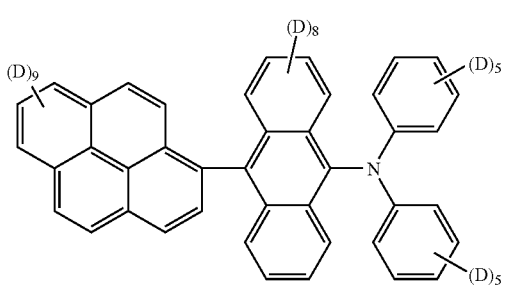
I-23
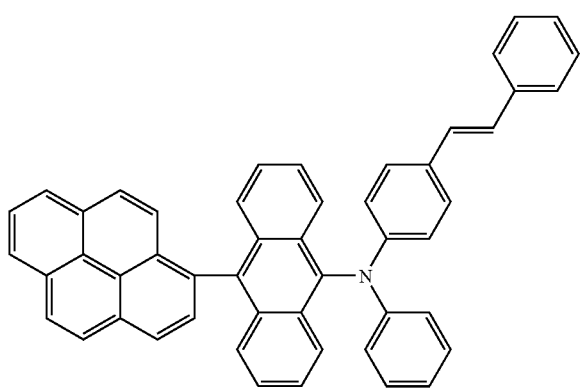
I-24
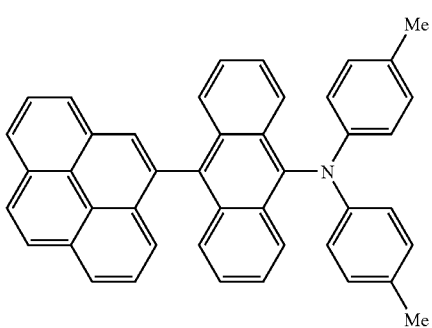
I-25
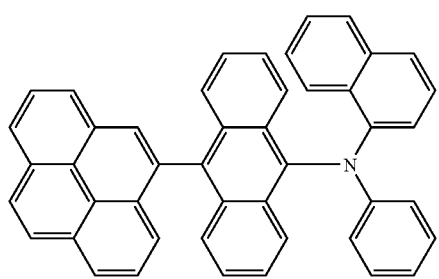
I-26
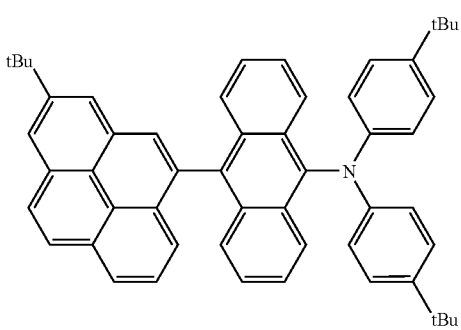

-continued
I-27
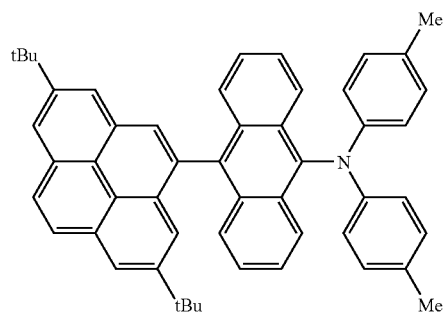
I-28
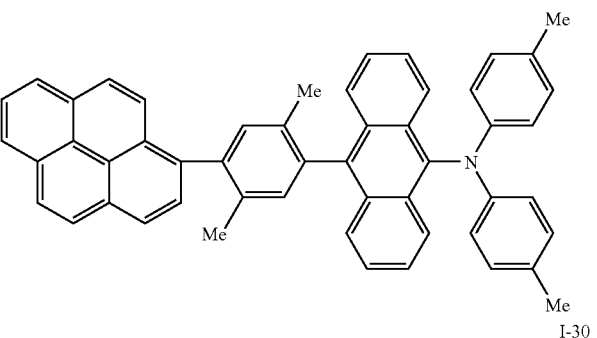
I-29
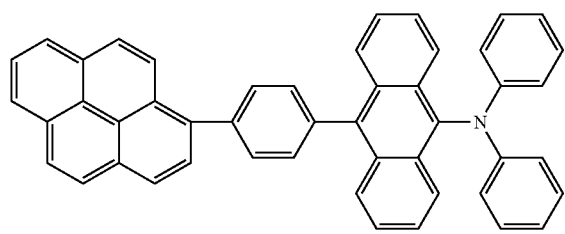
I-30
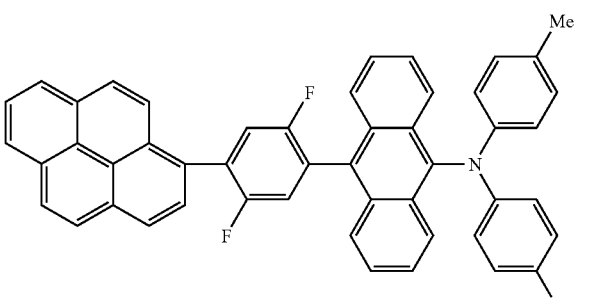
I-31
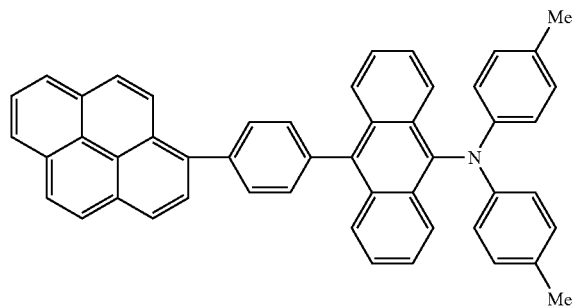
I-32
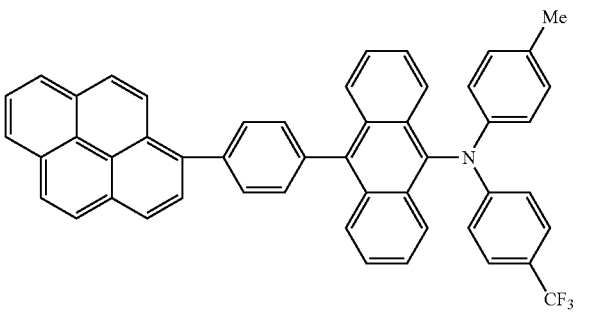
I-33
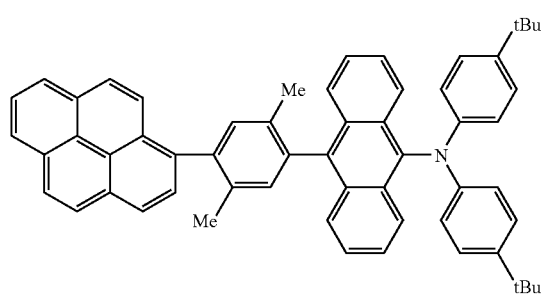
I-34
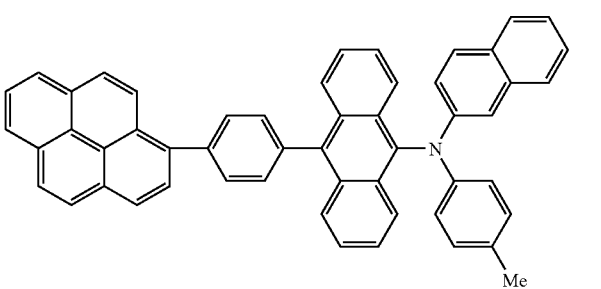
I-35
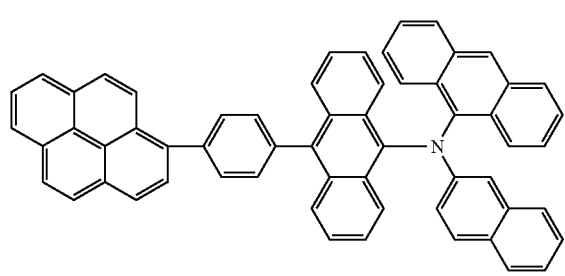
I-36
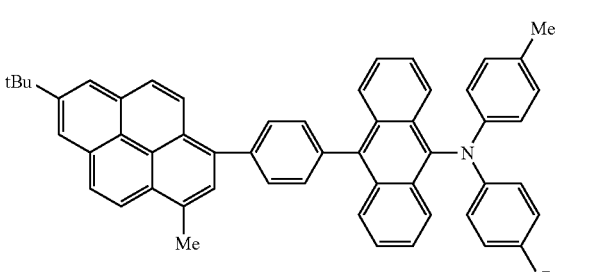

-continued
I-37
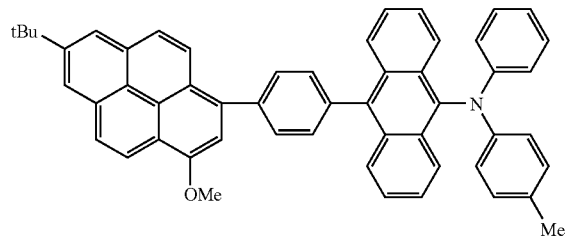
I-38
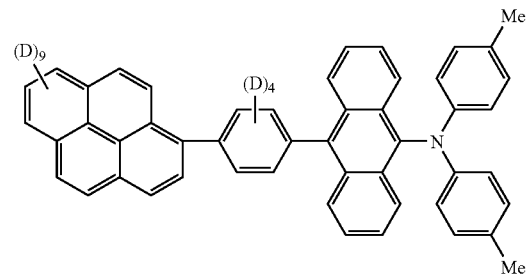
I-39
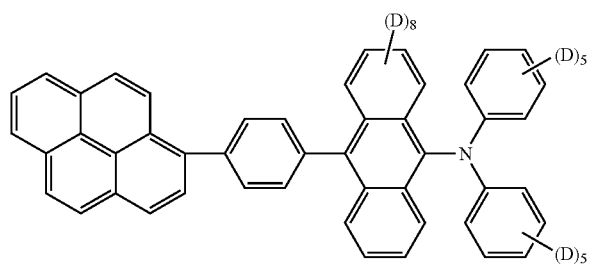
I-40
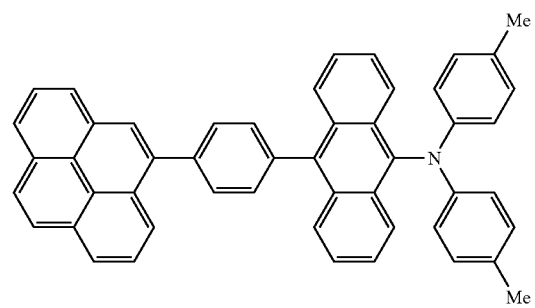
I-41
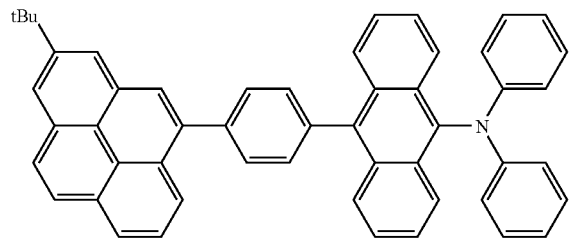
I-42
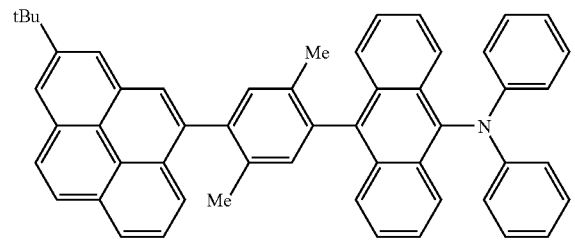
I-43
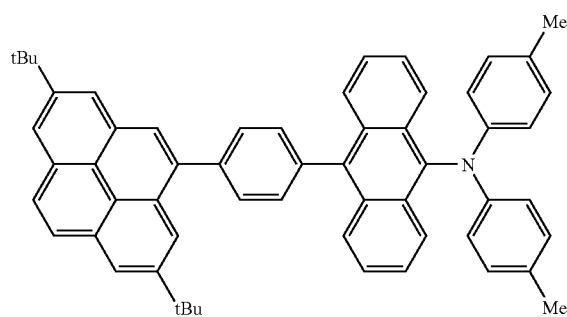
I-44
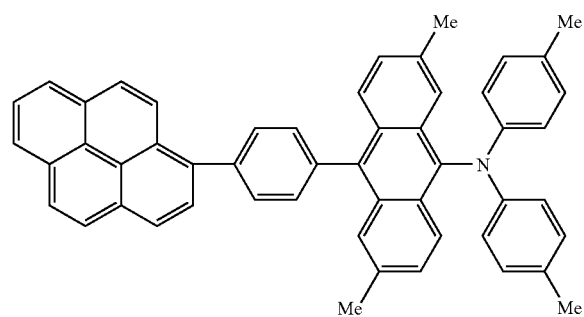
I-45
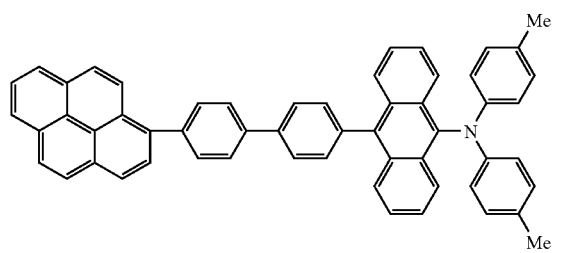
I-46
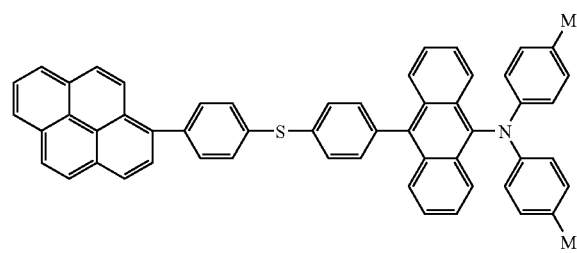

-continued
I-47
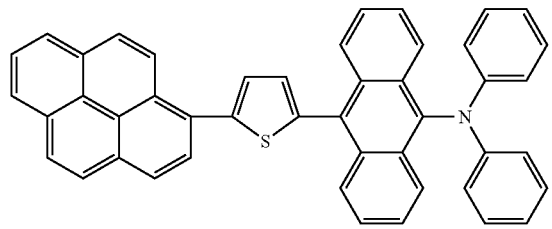
I-48
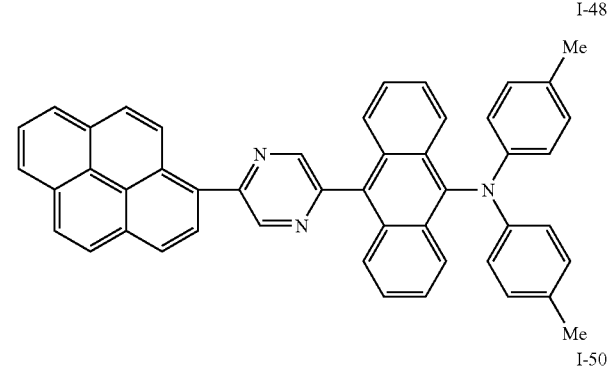
I-49
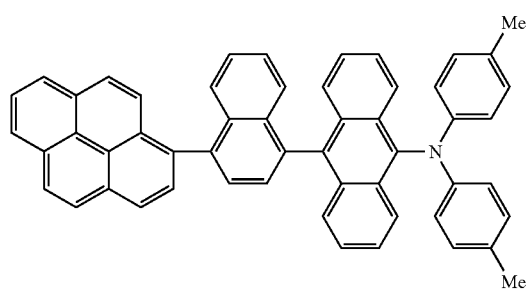
I-50
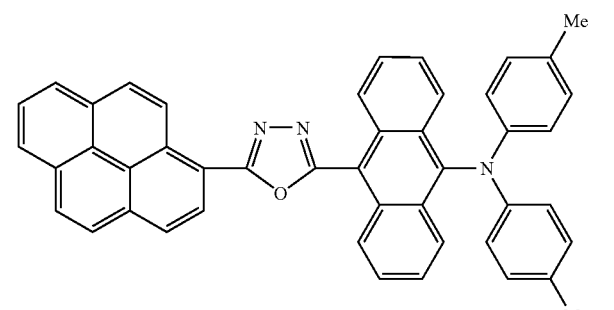
I-51
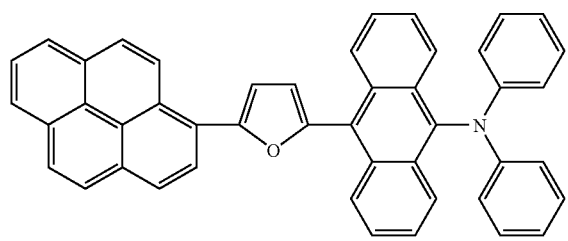
I-52
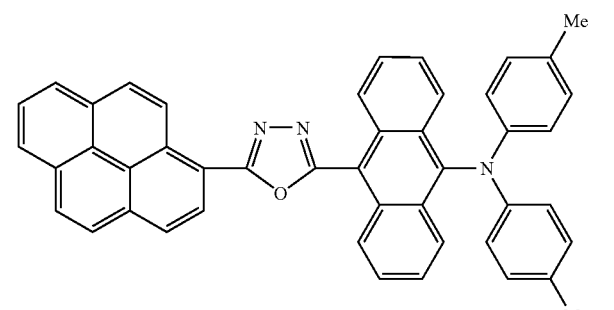
I-53
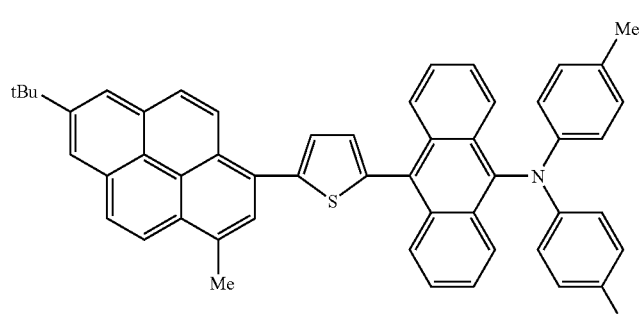
I-54
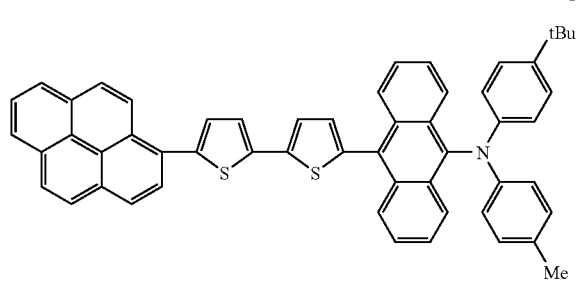
I-55
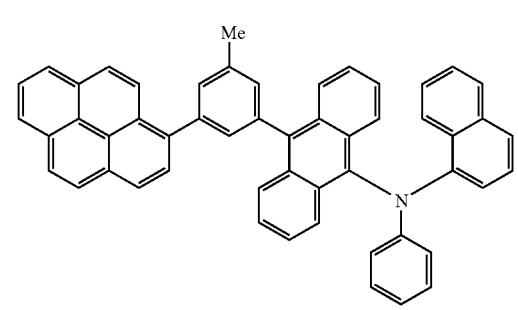

-continued
I-56
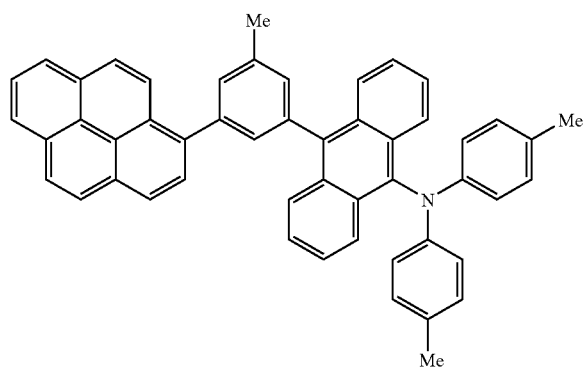
I-57
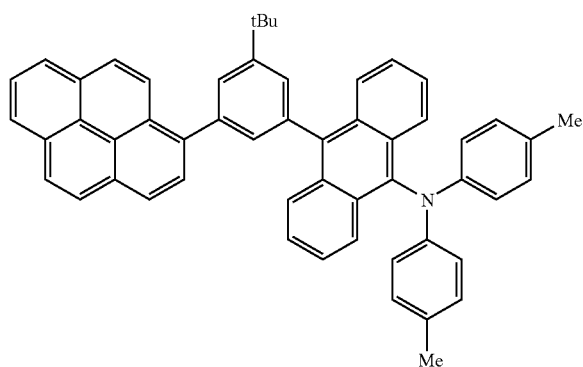
I-58
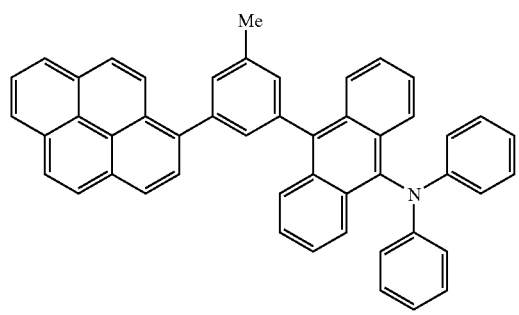
I-59
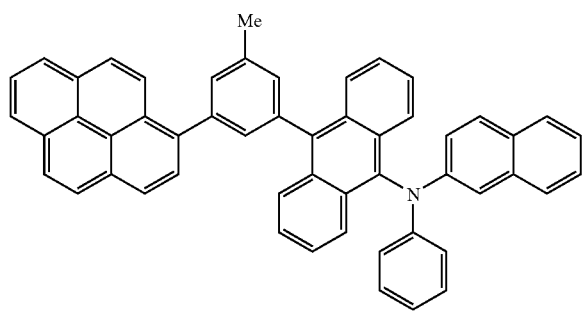
I-60
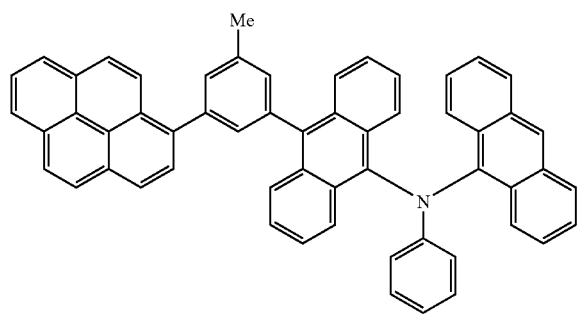
I-61
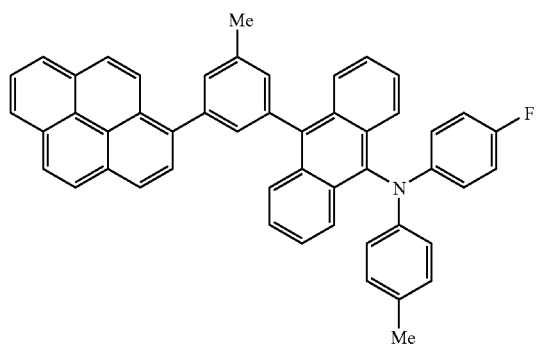
I-62
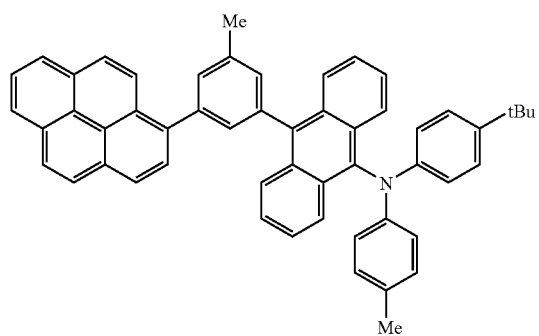
I-63
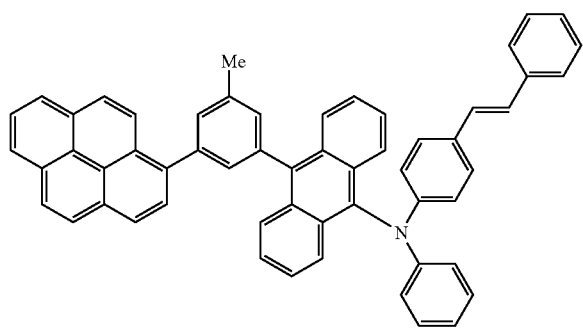

-continued
I-64
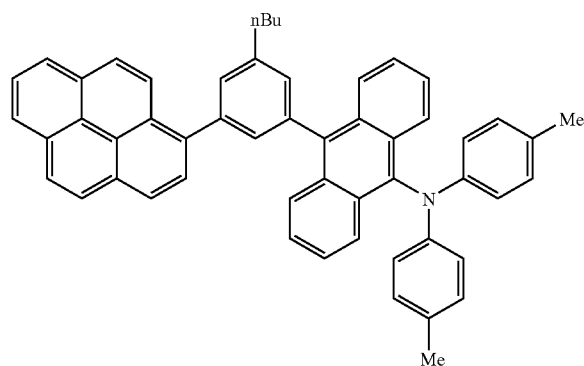
I-65
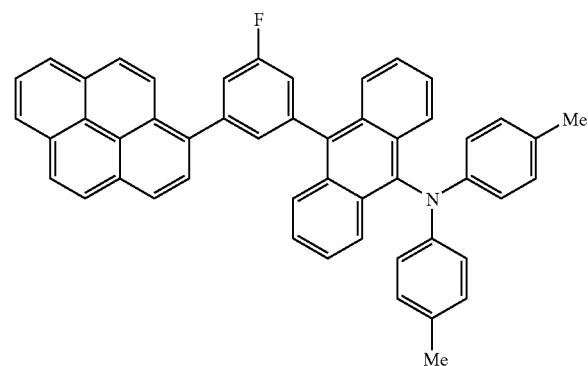
I-66
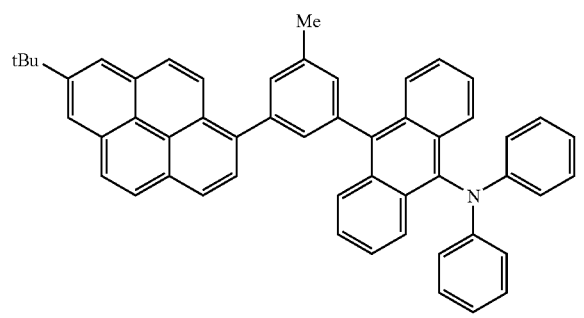
I-67
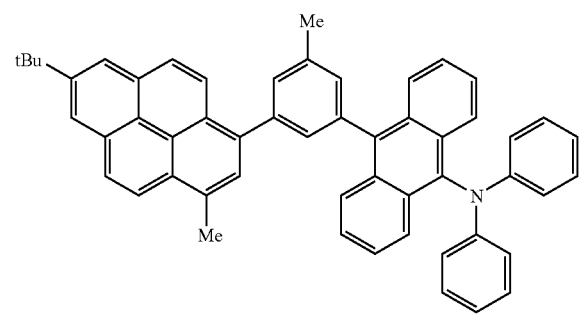
I-68
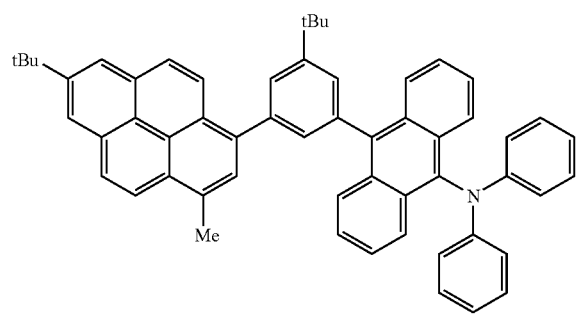
I-69
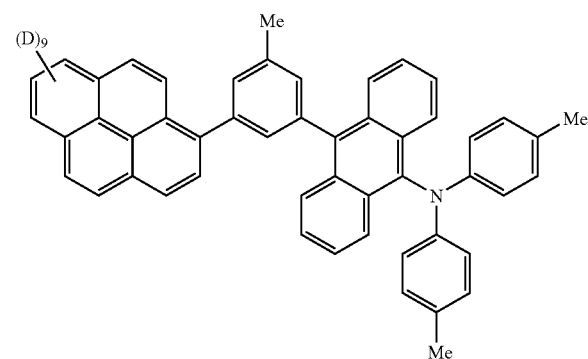
I-70
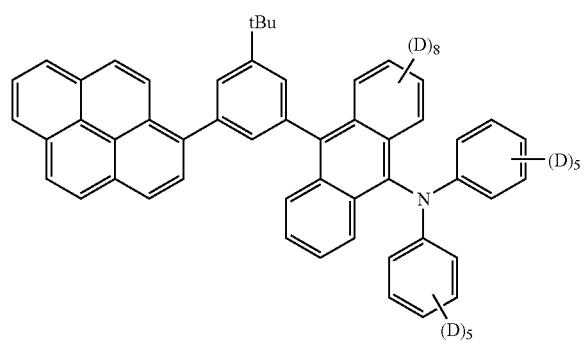
I-71
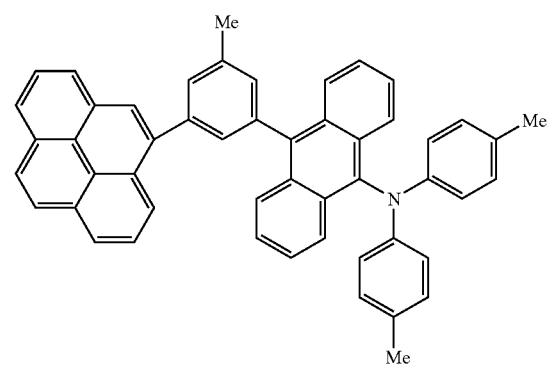

-continued
I-72
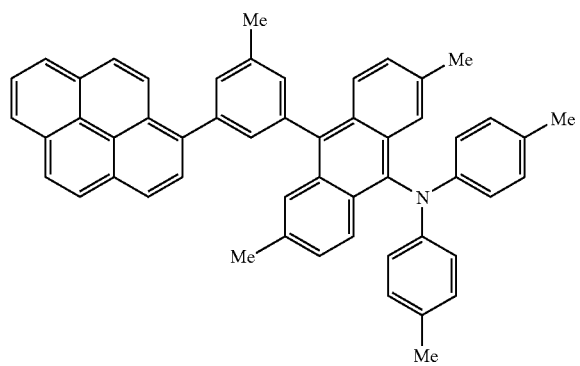
I-73
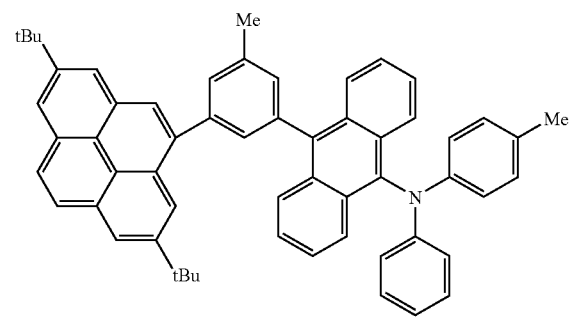
I-74
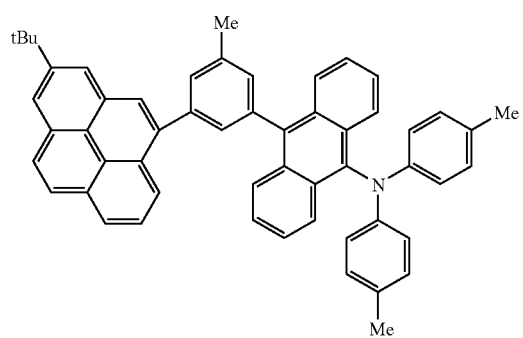
I-75
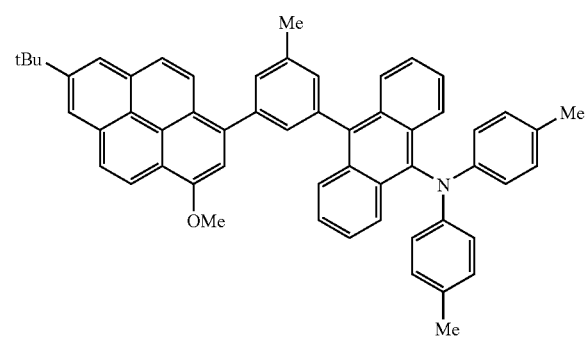
I-76
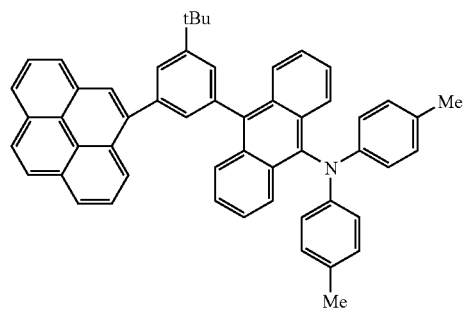
I-77
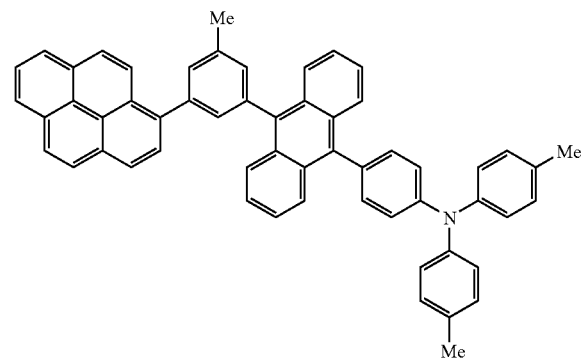
I-78
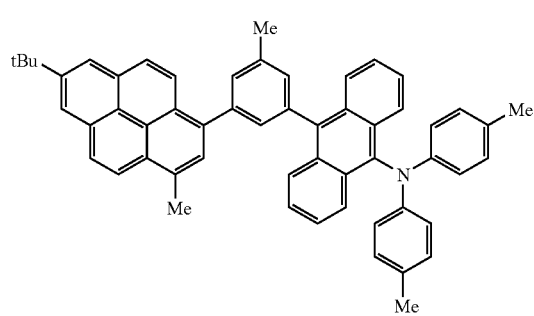
I-79
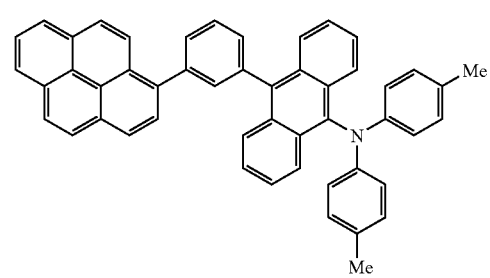

-continued
I-80
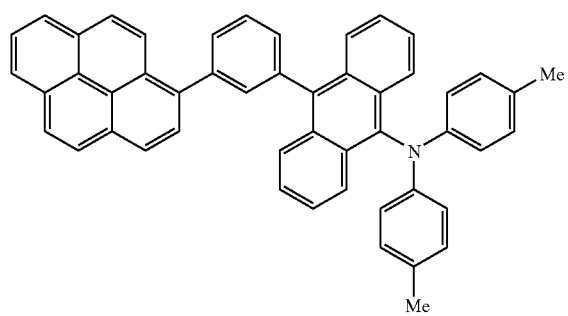
I-81
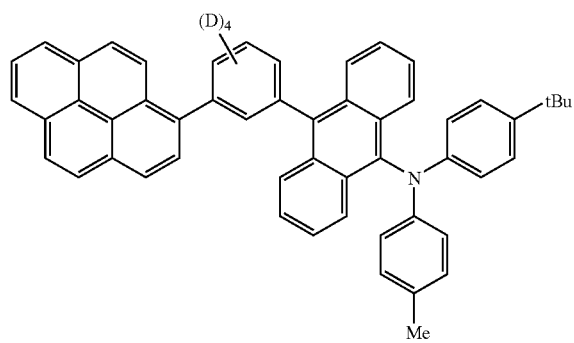
I-82
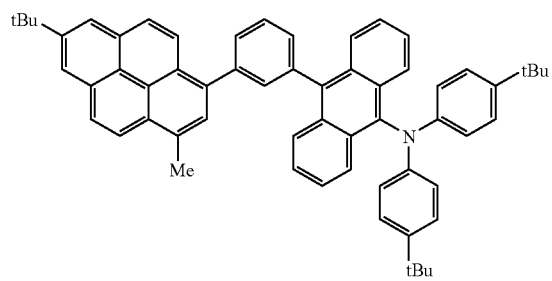
I-83
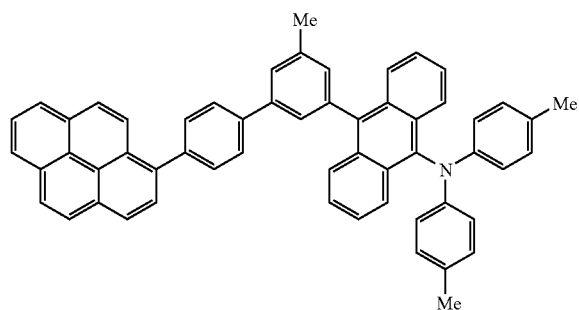
I-84
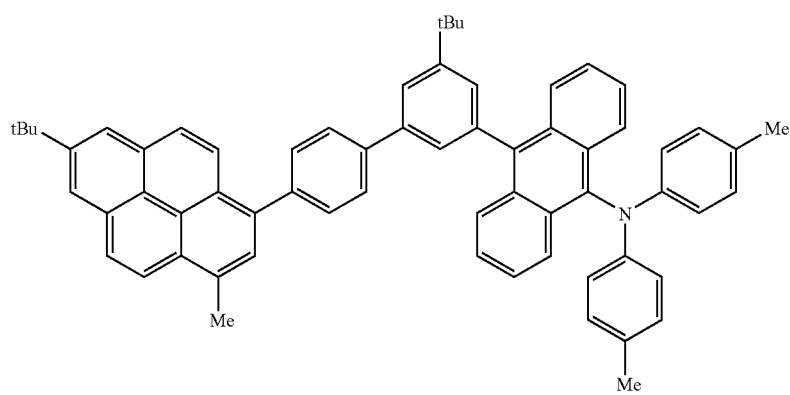
I-85
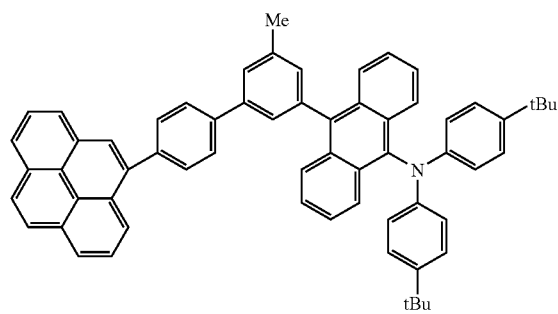
I-86
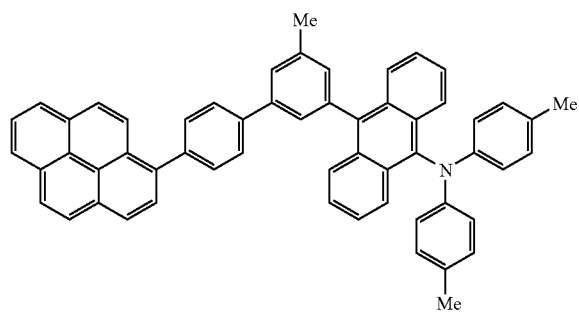

-continued
I-87
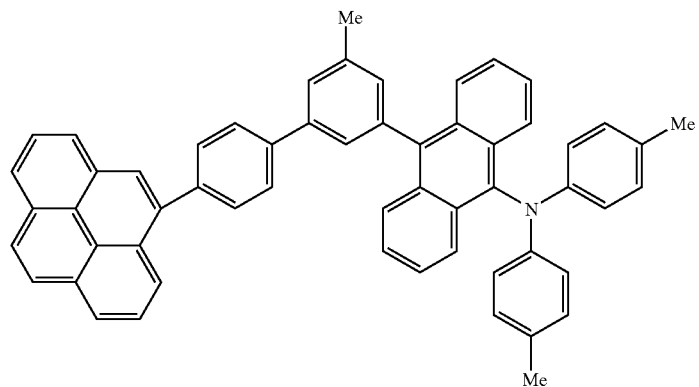
I-88
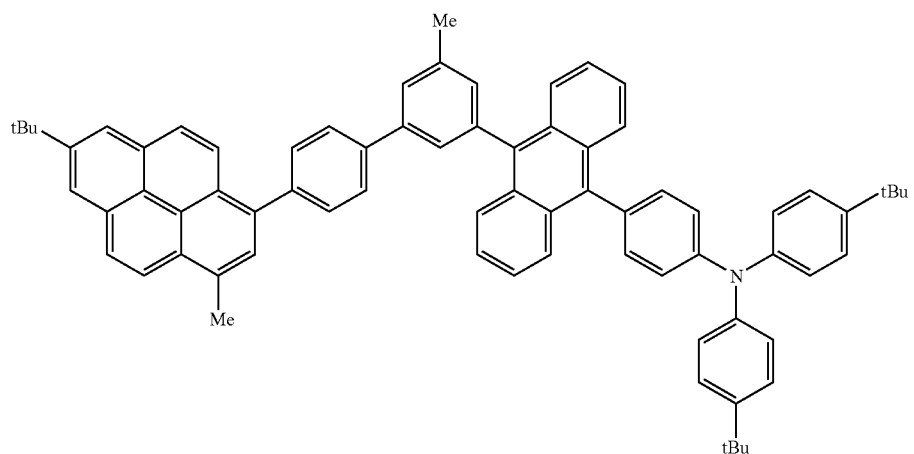
I-89
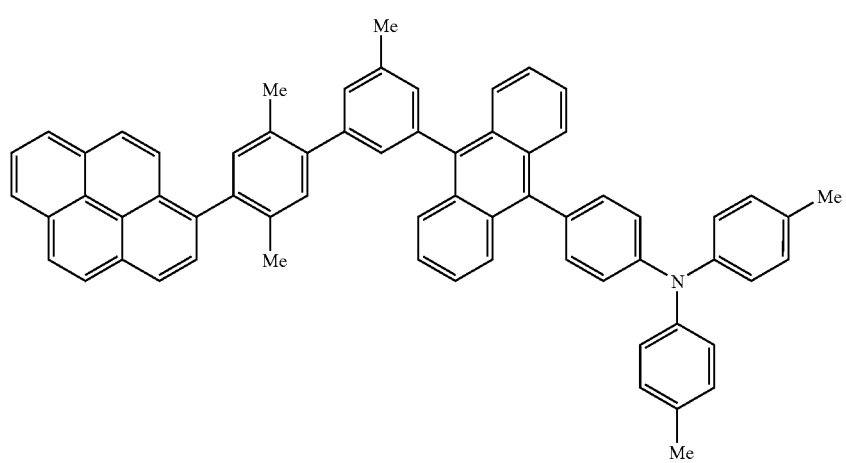

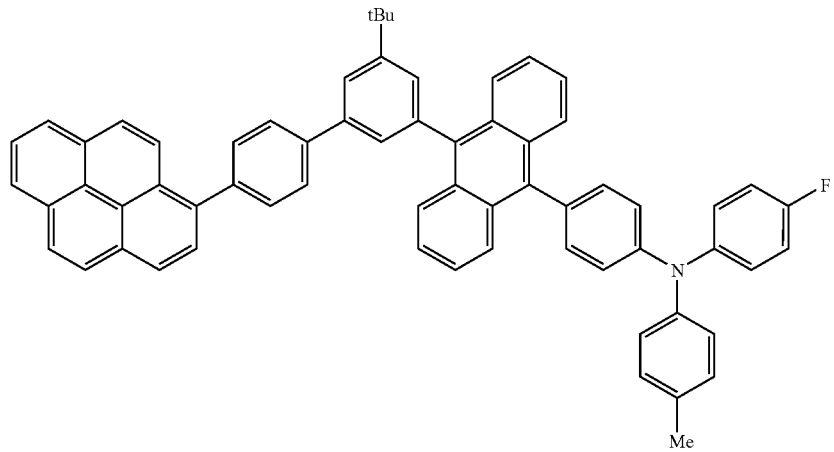

I-90

FIGS. 1 to 5 illustrate preferred embodiments of organic light-emitting devices of the present invention. Reference numerals are as follows: 1 denotes a substrate, 2 an anode, 3 a light emission layer, 4 a cathode, 5 a hole transport layer, 6 an electron transport layer, 7 a hole injection layer, and 8 a hole/exciton blocking layer.

FIG. 1 is a cross-sectional view illustrating an example of an organic light-emitting device of the present invention. Referring to FIG. 1, the device has a structure in which an anode 2, a light emission layer 3 and a cathode 4 are formed on a substrate 1 in that order. The light-emitting device herein used is useful for a case where the device has hole-transporting ability, electron-transporting ability and luminescence ability by itself, or a case where compounds having each ability are combined for forming the device.

Figure 2:
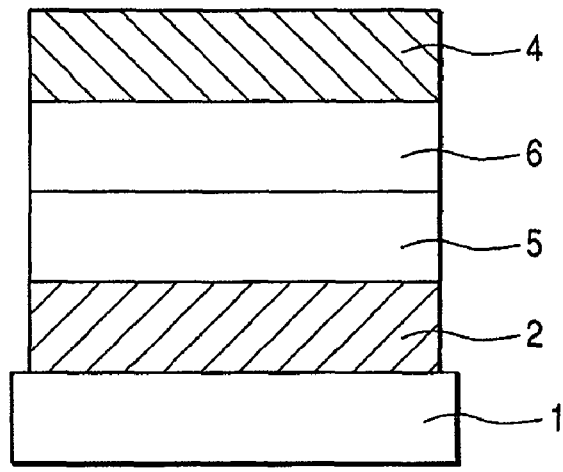
FIG. 2 is a cross-sectional view illustrating another example of an organic light-emitting device of the present invention.

FIG. 2 is a cross-sectional view illustrating another example of an organic light-emitting device of the present invention. Referring to FIG. 2, the device has a structure in which an anode 2, a hole transport layer 5, an electron transport layer 6 and a cathode 4 are formed on a substrate 1 in that order. This device is useful for a case where a light-emitting material having either or both of hole-transporting ability and electron-transporting ability is used for each layer in combination with only a hole-transporting material or electron-transporting material without luminescence ability. In this case, either a hole transport layer 5 or an electron transport layer 6 constitutes a light emission layer.

Figure 3:
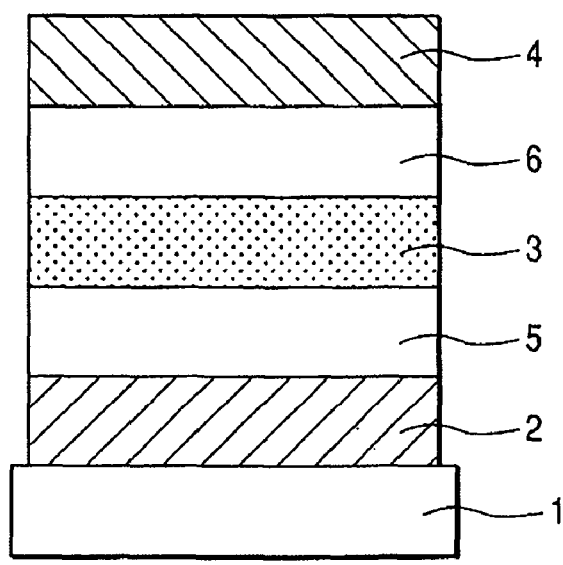
FIG. 3 is a cross-sectional view illustrating another example of an organic light-emitting device of the present invention.

FIG. 3 is a cross-sectional view illustrating another example of an organic light-emitting device of the present invention. Referring to FIG. 3, the device has a structure in which an anode 2, a hole transport layer 5, a light emission layer 3, an electron transport layer 6 and a cathode 4 are formed on a substrate 1 in that order. This device has separate functions of carrier transportation and light emission, and a compound having hole-transporting ability, a compound having electron-transporting ability and a compound having luminescence ability are used in appropriate combination, and thus selection degree of materials is greatly increased. In addition, because various compounds having different emission wavelengths can be used, diversification of luminescence color becomes possible. Furthermore, luminous efficiency can be improved by effectively trapping carriers or excitons in the central light emission layer 3.

Figure 4:
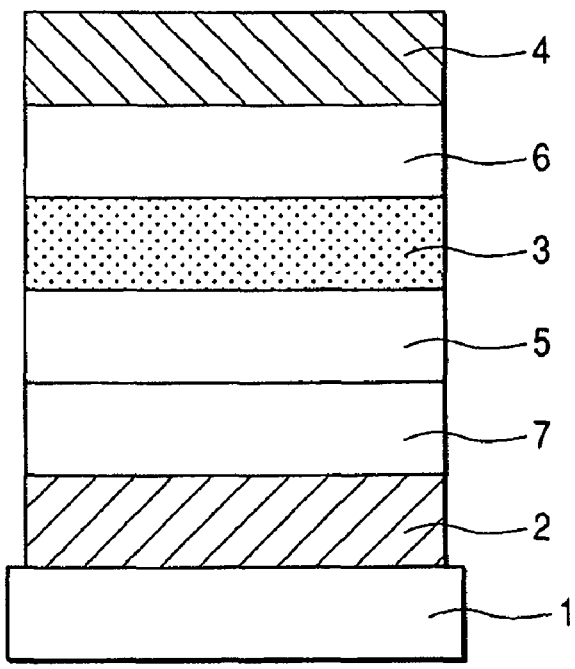
FIG. 4 is a cross-sectional view illustrating another example of an organic light-emitting device of the present invention.

FIG. 4 is a cross-sectional view illustrating another example of an organic light-emitting device of the present invention. Referring to FIG. 4, the device has a structure in which a hole injection layer 7 is disposed at the anode 2 side in FIG. 3, and this is effective for improvement in adhesiveness between the anode 2 and the hole transport layer 5 or improvement in hole-injecting property, and contributes to low voltage.

Figure 5:
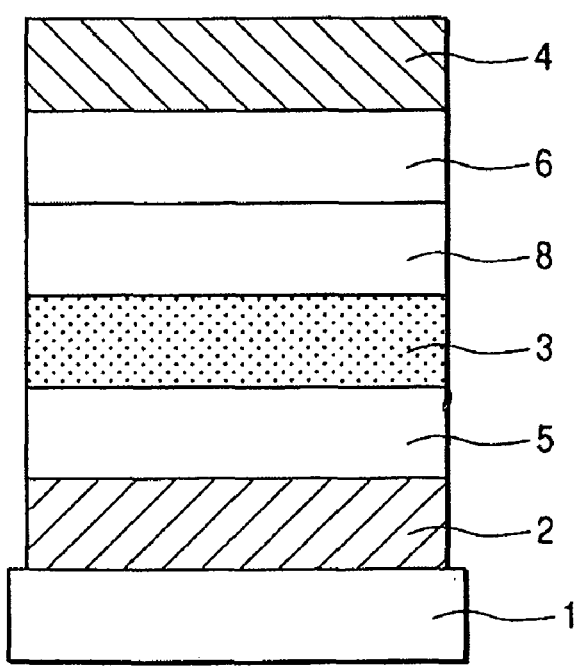
FIG. 5 is a cross-sectional view illustrating another example of an organic light-emitting device of the present invention.

FIG. 5 is a cross-sectional view illustrating another example of an organic light-emitting device of the present invention. Referring to FIG. 5, the device has a structure in which a layer for blocking passing of holes or excitons to the cathode 4 side (hole/exciton blocking layer 8) is interposed between the light emission layer 3 and the electron transport layer 6 in FIG. 3. This structure is effective for improvement in luminous efficiency because a compound having extremely high ionization potential is used for the hole/exciton blocking layer 8.

FIG. 1 to FIG. 5 illustrate only basic device structures and the structure of organic light-emitting devices using the fluorene compound of the present invention is not limited thereto. For example, various structures are available in which an insulating layer is formed at the interface between an electrode and an organic layer, in which an adhesion layer or an interference layer is formed, or in which a hole transport layer composed of two layers of different ionization potentials is formed.

The fluorene compound of the present invention can be used in any forms of FIG. 1 to FIG. 5.

In particular, an organic layer using the fluorene compound of the present invention is useful as a light emission layer, an electron transport layer or a hole transport layer, and a layer formed by vacuum deposition or solution coating is less likely to cause crystallization and excellent in stability with the elapse of time.

In the present invention, the above-described fluorene compound of the present invention is used particularly as a constituent of a light emission layer. However, a conventionally known low molecular weight or polymeric hole-transporting compound, luminescent compound or electron-transporting compound may also be used together according to need.

Examples of such compounds are described below.

A hole-injecting/transporting material preferably has good mobility for facilitating injection of holes from an anode and transporting the injected holes to a light emission layer. Examples of low molecular weight materials (LMW materials) and high molecular weight materials (HMW materials) having hole-injecting/transporting ability include triarylamine derivatives, phenylenediamine derivatives, triazole derivatives, oxadiazole derivatives, imidazoles derivatives, pyrazoline derivatives, pyrazolone derivatives, oxazole derivatives, fluorenone derivatives, hydrazone derivatives, stilbene derivatives, phthalocyanine derivatives, porphyrin derivatives, poly(vinyl carbazole), poly(silylene), poly(thiophene) and other conductive polymers, but are obviously not limited thereto. Some specific examples thereof are described below.

LMW hole-injecting/transporting materials

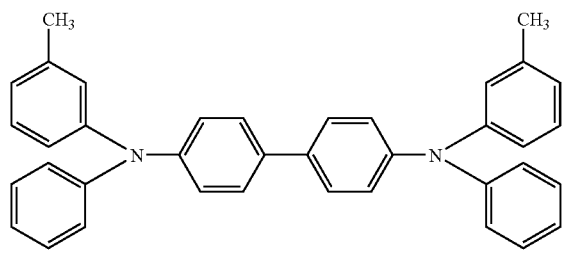

TPD

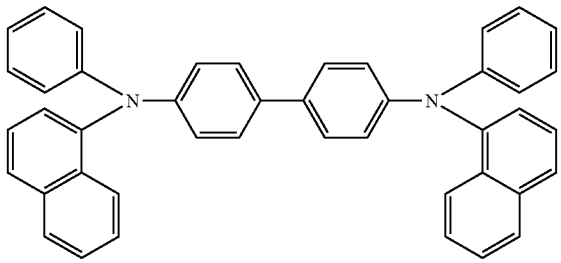

α-NPD

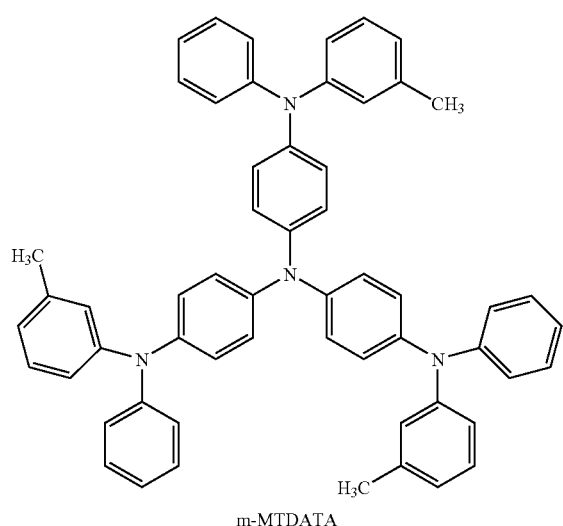

m-MTDATA

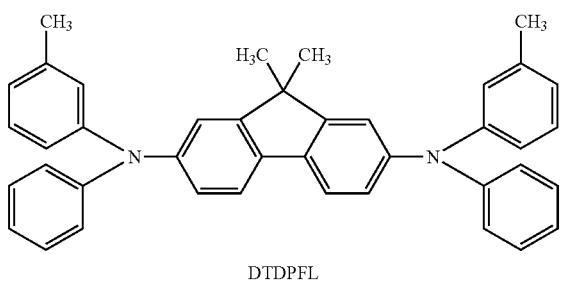

DTDPFL

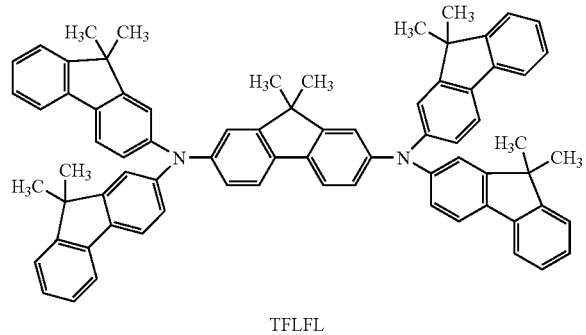

TFLFL

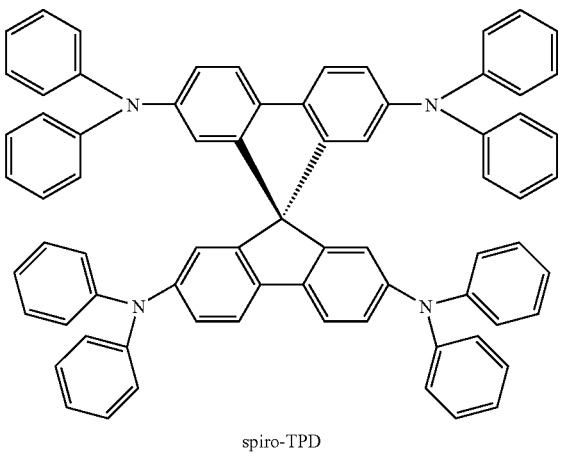

spiro-TPD

-continued
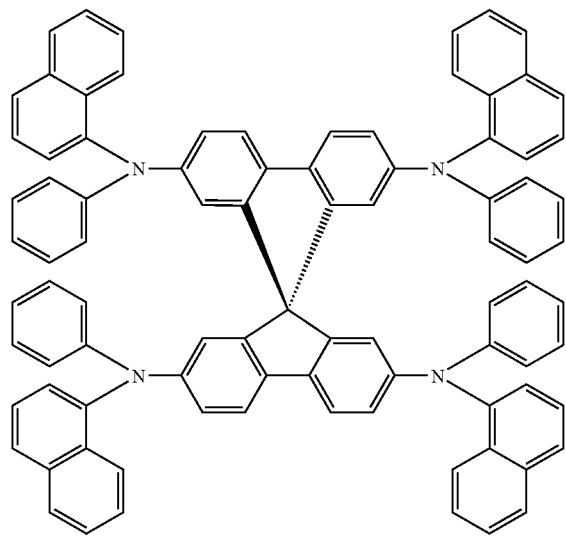
spiro-NPD
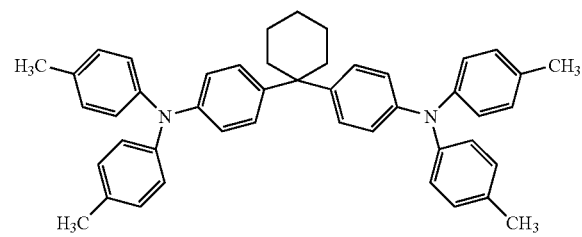
TPAC
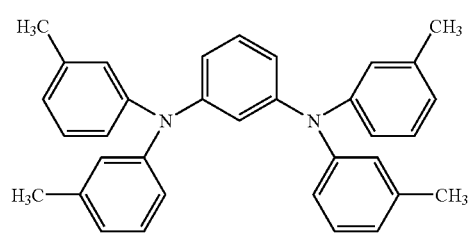
PDA
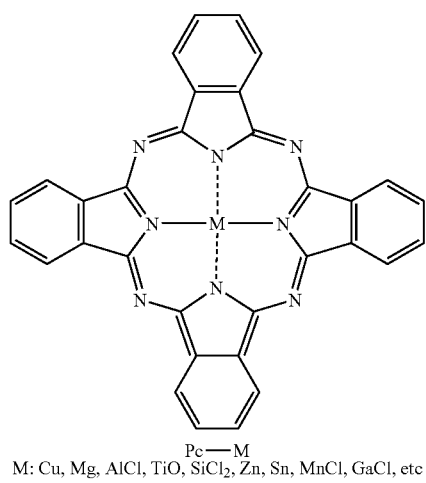
Pc—M
M: Cu, Mg, AlCl, TiO, SiCl$_2$, Zn, Sn, MnCl, GaCl, etc
HMW hole-transporting materials
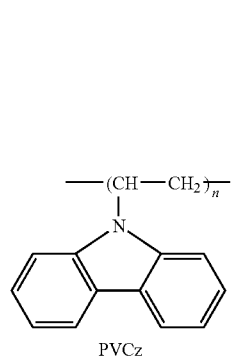
PVCz
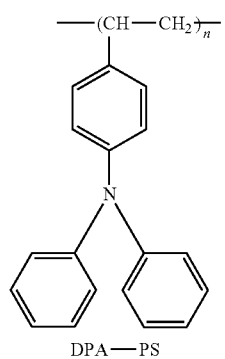
DPA—PS -continued

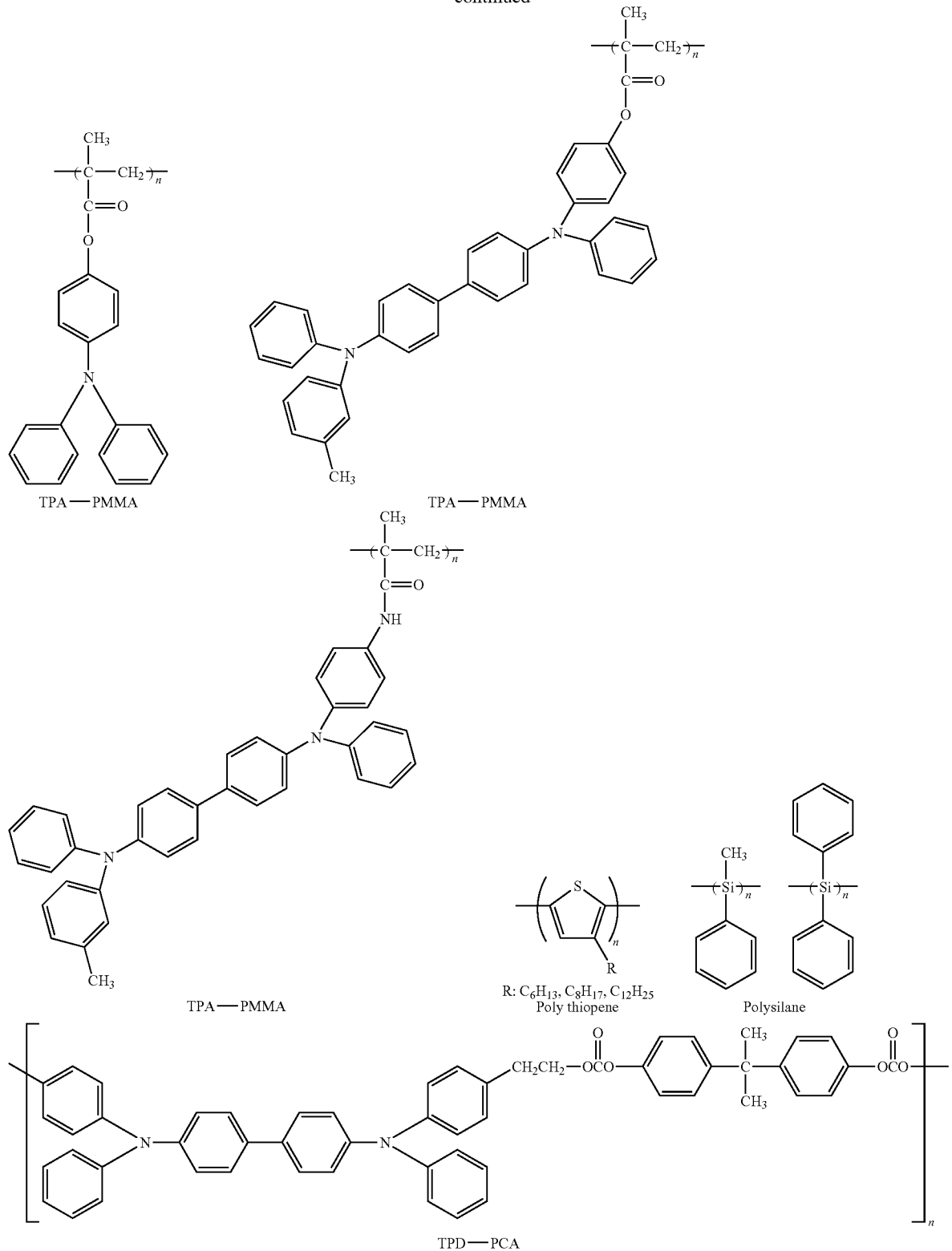

Examples of materials that mainly has a light emission function and can be used in addition to the fluorene compound of the present invention include polycyclic condensed aromatic compounds (e.g., naphthalene derivatives, phenanthrene derivatives, fluorene derivatives, pyrene derivatives, tetracene derivatives, coronene derivatives, chrysene derivatives, perylene derivatives, 9,10-diphenylanthracene derivatives and rubrene), quinacridone derivatives, acridone derivatives, coumarin derivatives, pyran derivatives, Nile red, pyrazine derivatives, benzimidazole derivatives, benzothiazole derivatives, benzoxazole derivatives, stilbene derivatives, organometallic complexes (e.g., organic aluminum complexes such as tris(8-quinolinolate)aluminum, organic beryllium complex), and high molecular weight derivatives such as poly(phenylenevinylene) derivatives, poly(fluorene) derivatives, poly(phenylene) derivatives, poly(thienylene vinylene) derivatives, poly(acetylene) derivatives, but are obviously not limited thereto. Some specific examples thereof are described below.

LMW light-emitting materials

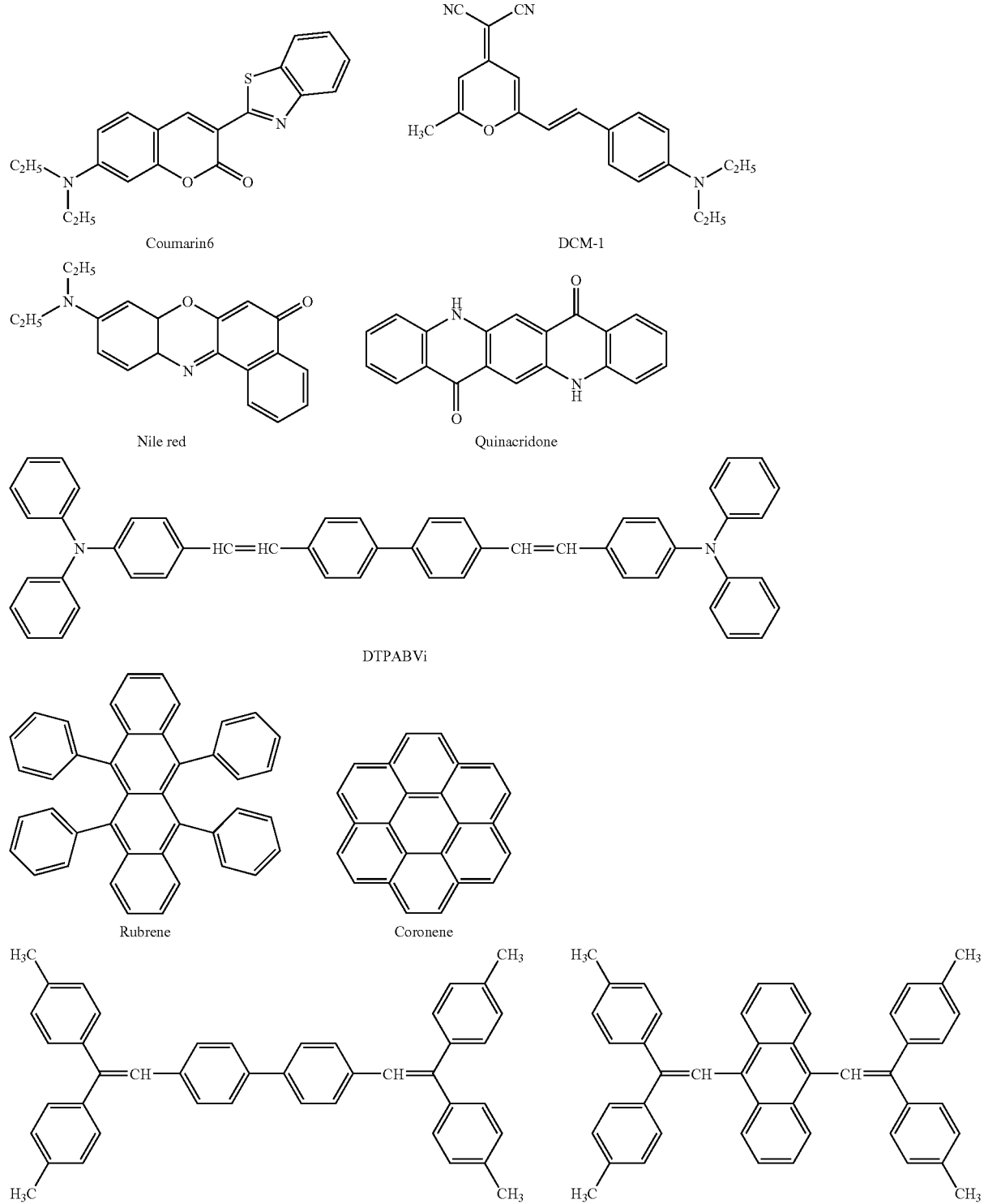

-continued

HMW light-emmitting materials materials

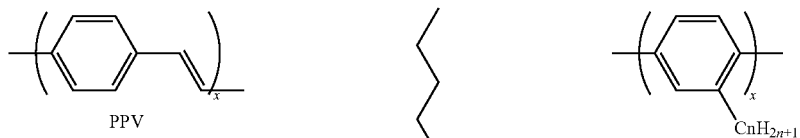

PPV

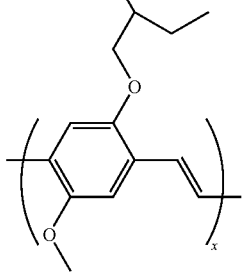

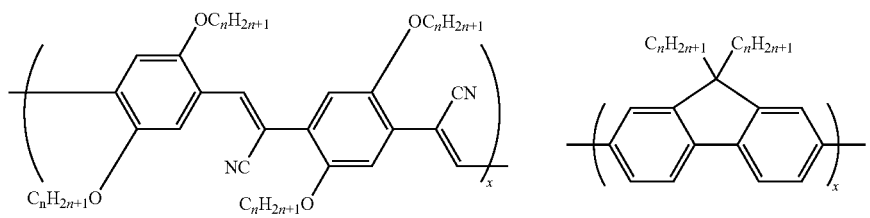

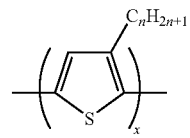

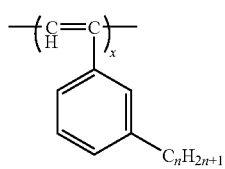

Metal complex light-emitting materials

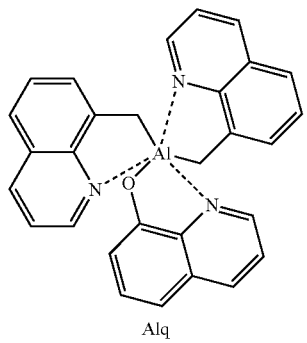

Alq

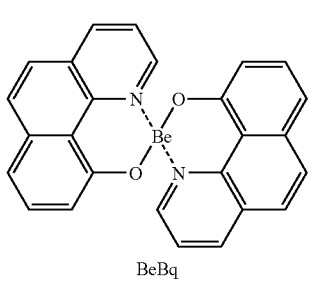

BeBq

An electron-injecting/transporting material may be optionally selected from materials which facilitate injection of electrons from a cathode and have ability to transport the injected electrons to a light emission layer. These materials are selected in consideration of the balance with carrier mobility of a hole-transporting material. Examples of materials having electron-injecting/transporting ability include oxadiazole derivatives, oxazole derivatives, thiazole derivatives, thiadiazole derivatives, pyrazine derivatives, triazole derivatives, triazine derivatives, perylene derivatives, quinoline derivatives, quinoxaline derivatives, fluorenone derivatives, anthrone derivatives, phenanthroline derivatives and organometallic complexes, but are obviously not limited thereto. Some specific examples thereof are described below.

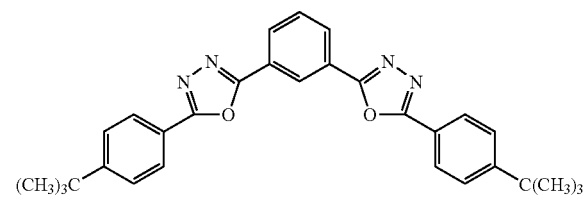

-continued

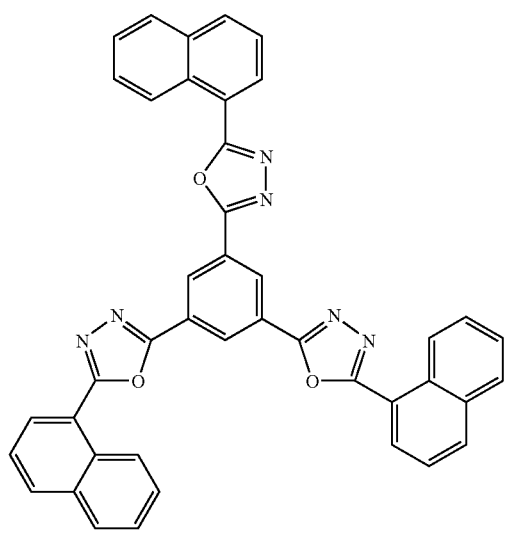

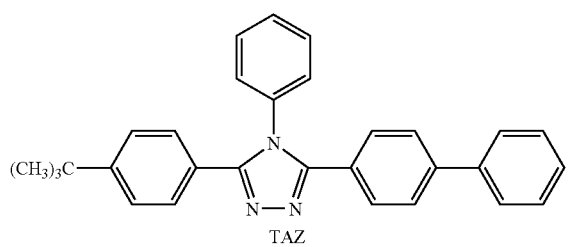
TAZ

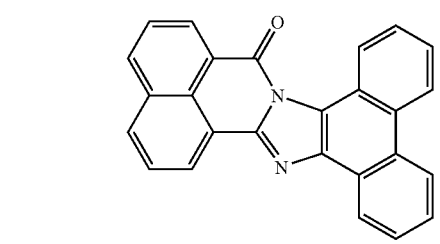

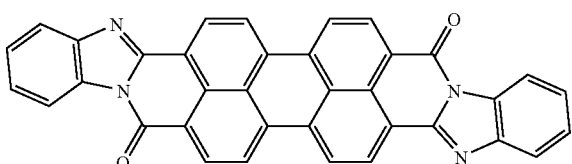

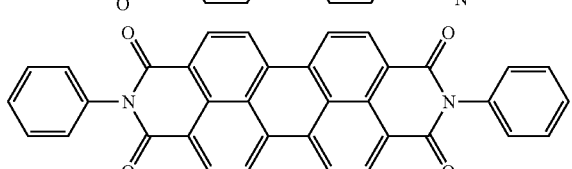

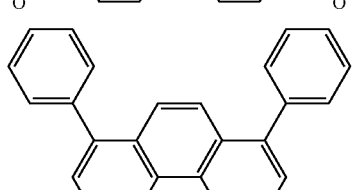
Bphen

-continued

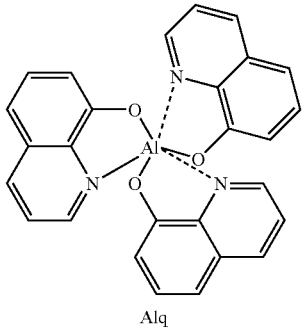
Alq

In the organic light-emitting device of the present invention, a layer containing the fluorene compound of the present invention and a layer comprising another organic compound are generally formed as thin films by vacuum deposition, ionized evaporation, sputtering, plasma or a known coating method (e.g., spin coating, dipping, casting, an LB method, an ink jet method) after these compounds are dissolved in an appropriate solvent. In particular, when forming into a film by the coating method, a film may also be formed in combination with an appropriate binder resin.

The binder resin described above may be selected from various binder resins, and examples thereof include polyvinylcarbazole resin, polycarbonate resin, polyester resin, polyallylate resin, polystyrene resin, ABS resin, polybutadiene resin, polyurethane resin, acrylic resin, methacrylic resin, butyral resin, polyvinyl acetal resin, polyamide resin, polyimide resin, polyethylene resin, polyether sulfone resin, diarylphthalate resin, phenol resin, epoxy resin, silicone resin, polysulfone resin and urea resin, but are not limited thereto. These may be used alone or two ore more of them may be mixed as a copolymer. In addition, known additives such as a plasticizer, an antioxidant and an ultraviolet absorber may also be used together according to need.

As an anode material, those with a highest possible work function are preferred, and for example, metals such as gold, platinum, silver, copper, nickel, palladium, cobalt, selenium, vanadium and tungsten, and alloys thereof, and metal oxides such as tin oxide, zinc oxide, indium oxide, indium tin oxide (ITO) and indium zinc oxide may be used. In addition, conductive polymers such as polyaniline, polypyrrole, polythiophene and polyphenylene sulfide may be used. These electrode materials may be used alone or a plurality of them may be used together. The anode may have a monolayer structure or a multilayer structure.

On the other hand, as a cathode material, those with a low work function are preferred, and for example, metals such as lithium, sodium, potassium, calcium, magnesium, aluminum, indium, ruthenium, titanium, manganese, yttrium, silver, lead, tin and chromium, and alloys of a plurality of those such as lithium-indium, sodium-pottasium, magnesium-silver, aluminum-lithium, aluminum-magnesium and magnesium-indium may be used. Metal oxides such as indium tin oxide (ITO) may also be used. These electrode materials may be used alone or a plurality of them may be used together. The cathode may have a monolayer structure or a multilayer structure.

It is desired that at least one of the anode and the cathode is transparent or semi-transparent.

The substrate used in the present invention is not particularly limited, and opaque substrates such as metal substrates and ceramic substrates, and transparent substrates such as glass, quartz and plastic sheet are used. Further, luminescent colors can be controlled by using a color filter film, a fluorescent color conversion film or a dielectric reflection film as a substrate. Moreover, a thin film transistor (TFT) may be formed on a substrate and jointed with other parts to fabricate a device.

Regarding the direction of light introduction into the device, any of bottom emission structures (structures for introducing light from the substrate side) and top emission structures (structures for introducing light from the opposite side of the substrate) is available.

A protective layer or an encapsulation layer may also be formed on the fabricated device in order to prevent contact with oxygen or moisture. Examples of protective layers include diamond thin films, films of inorganic materials such as metal oxide and metal nitride, fluorine resins, polymer films of polyparaxylene, polyethylene, silicone resin or polystyrene resin, and photo-curing resins. In addition, glass, gas impermeable film or metal may be applied thereto and the device may be packaged using an appropriate encapsulation resin.

EXAMPLES

In the following, the present invention is described in more detail by means of Examples, but the present invention is not limited thereto.

Example 1

Synthesis of Exemplified Compound A-7 a)

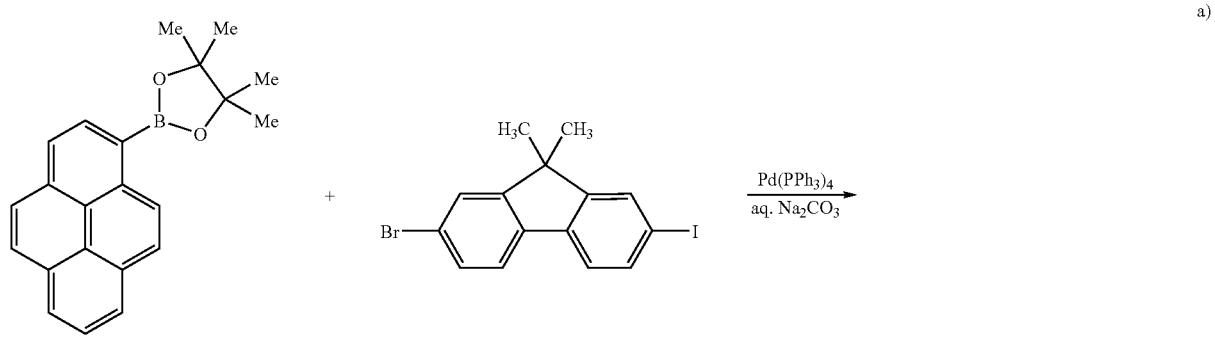

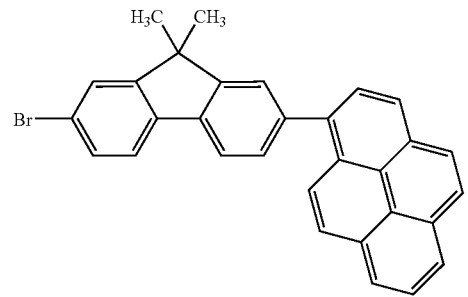

b)

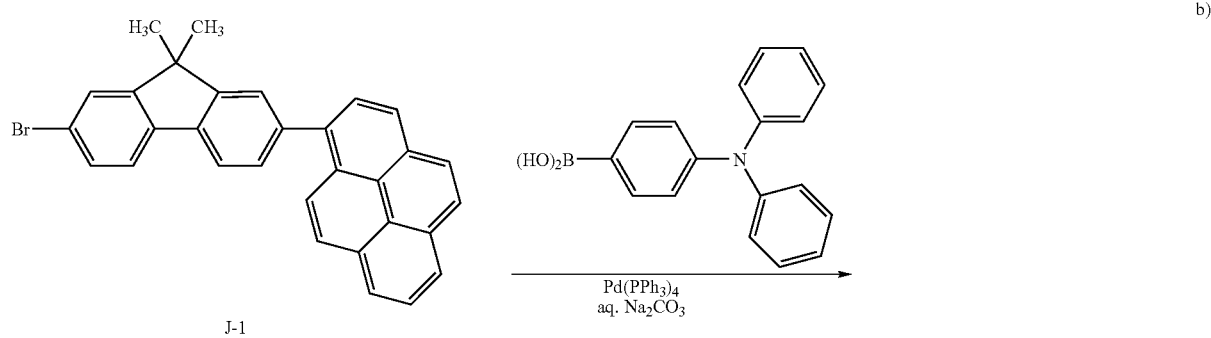

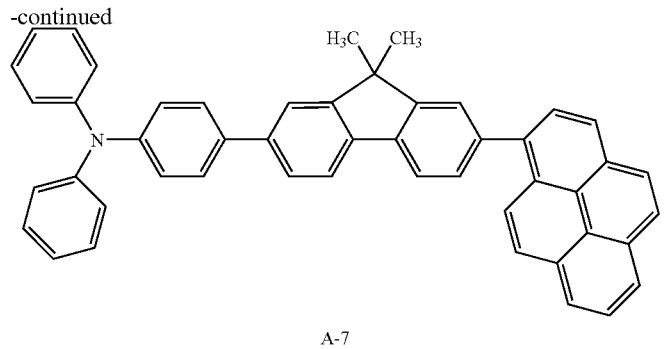

A-7 a) Synthesis of Raw Material J-1

A 500 ml three-neck flask was charged with 9.6 g (24.1 mmol) of 2-iodo, 7-bromo-9,9-dimethylfluorene, 8.0 g (24.4 mmol) of pyrene-1-pinacolborane, 200 ml of toluene and 20 ml of ethanol. With stirring under nitrogen atmosphere at room temperature, an aqueous solution of sodium carbonate 20 g/water 120 ml was added thereto dropwise, and then 0.25 g (0.20 mmol) of tetrakis(triphenylphosphine)palladium (0) was added thereto. The mixture was heated to 77° C. and stirred for 5 hours. After the reaction, the organic layer was extracted with toluene and dried over anhydrous sodium sulfate, and the resultant was purified using a silica gel column (heptane+toluene mixed developing solvent) to obtain 7.5 g of compound J-1 (white crystal) (yield 66.2%).

b) Synthesis of Exemplified Compound A-7

A 200 ml three-neck flask was charged with 0.80 g (1.70 mmol) of compound J-1, 0.93 g (3.40 mmol) of 4-diphenylaminobenzeneboronic acid, 120 ml of toluene and 20 ml of ethanol. With stirring under nitrogen atmosphere at room temperature, an aqueous solution of sodium carbonate 10 g/water 100 ml was added thereto dropwise, and then 0.20 g (0.170 mmol) of tetrakis(triphenylphosphine)palladium (0) was added thereto. The mixture was heated to 77° C. and stirred for 5 hours. After the reaction, the organic layer was extracted with toluene and dried over anhydrous sodium sulfate, and the resultant was purified using a silica gel column (heptane+toluene mixed developing solvent) to obtain 0.764 g of exemplified compound A-7 (white crystal) (yield 70.5%).

Example 2

Synthesis of Exemplified Compound A-2

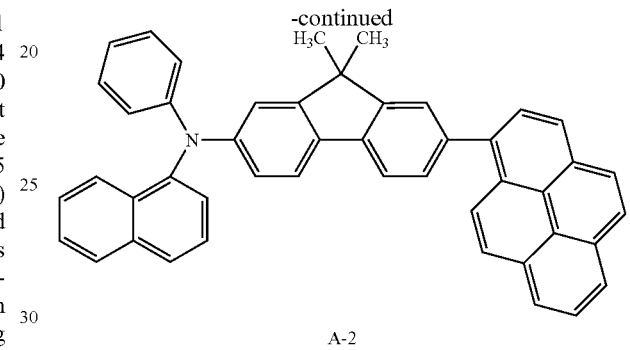

A-2

A 200 ml three-neck flask was charged with 0.80 g (1.70 mmol) of compound J-1, 0.75 g (3.40 mmol) of α-naphthylphenylamine, 0.65 g (6.80 mmol) of sodium tert-butoxide and 100 ml of xylene. With stirring under nitrogen atmosphere at room temperature, thereto was added 34.4 mg (0.17 mmol) of tri-tert-butylphosphine and then 48.9 mg (0.085 mmol) of palladium dibenzylideneacetone. The mixture was heated to 125° C. and stirred for 3 hours. After the reaction, the organic layer was extracted with toluene and dried over anhydrous sodium sulfate, and the resultant was purified using a silica gel column (heptane+toluene mixed developing solvent) to obtain 0.642 g of exemplified compound A-2 (white crystal) (yield 61.6%).

Example 3

Synthesis of Exemplified Compound A-32

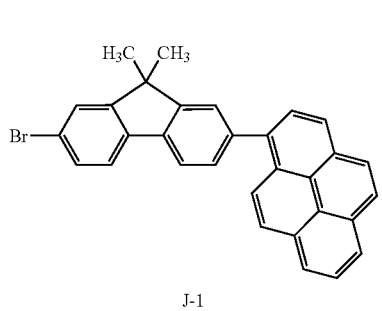

J-1

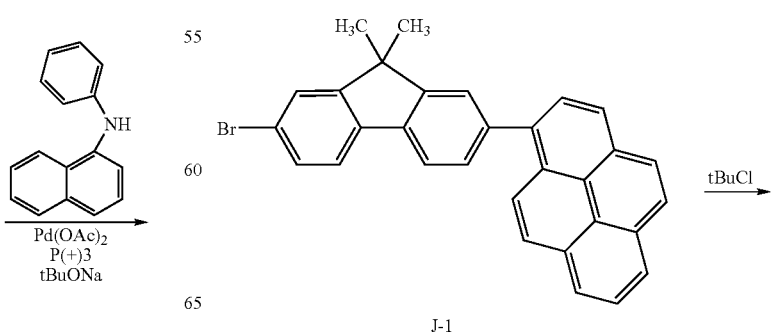

J-1

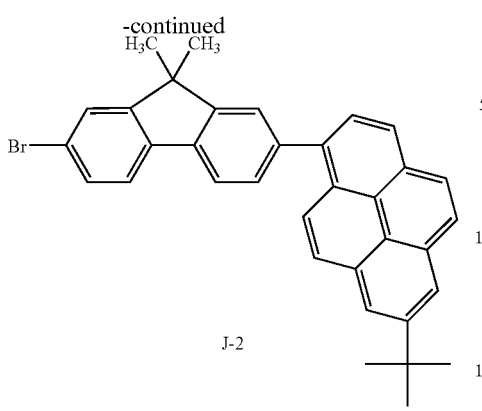

J-2 a) Synthesis of compound J-2

A 300 ml three-neck flask was charged with 2.50 g (5.31 mmol) of compound J-1, 0.926 g (10.0 mmol) of tert-butyl chloride and 100 ml of dichloromethane. With stirring at 0° C., 0.733 g (5.50 mmol) of aluminum chloride was added thereto in small portions. After stirring at 0° C. for 30 minutes, the mixture was heated to room temperature and stirred for 3 hours. After the reaction, the organic layer was poured into 200 ml of water, extracted with chloroform and dried over anhydrous sodium sulfate, and the resultant was purified using a silica gel column (heptane+toluene mixed developing solvent) to obtain 2.33 g of compound J-2 (white crystal) (yield 82.3%).

b) Synthesis of Exemplified Compound A-32

Exemplified compound A-32 was synthesized in the same manner as in Example 2 using compound J-2 instead of compound J-1.

Examples 4, 5

Synthesis of Exemplified Compounds A-10, A-12

Exemplified compounds A-10 and A-12 were synthesized in the same manner as in Example 1 using 4-di-α-naphthylamino benzeneboronic acid and 4-α-naphthylphenylamino benzeneboronic acid instead of 4-diphenylamino benzeneboronic acid, respectively.

Examples 6, 7

Synthesis of Exemplified Compounds A-4 and A-6

Exemplified compounds A-4 and A-6 were synthesized in the same manner as in Example 2 using dimesitylamine and carbazole instead of α-naphthylphenylamine, respectively.

Example 8

An organic light-emitting device having a structure shown in FIG. 3 was fabricated by the method described below.

A glass substrate as a substrate 1 on which a film of indium tin oxide (ITO) was formed by sputtering in a film thickness of 120 nm as an anode 2 was used as a transparent conductive supporting substrate. This was subjected to ultrasonic cleaning in acetone and isopropyl alcohol (IPA) in that order, washed by boiling in IPA and dried. This was further subjected to UV/ozone cleaning and the obtained substrate was used as a transparent conductive supporting substrate.

A chloroform solution was prepared using a compound represented by the following structural formula as a hole-transporting material so that the concentration of the compound was 0.1 wt %.

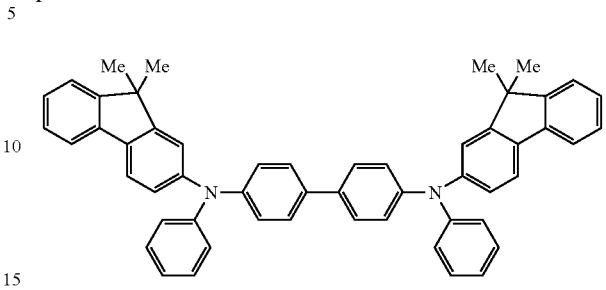

The solution was dropped on the above-described ITO electrode and spin-coated first at a rotational speed of 500 RPM for 10 seconds and then at a rotational speed of 1000 RPM for 1 minute to form a film. Subsequently, drying was performed in a vacuum oven at 80° C. for 10 minutes to completely remove the solvent in the thin film. The formed hole transport layer 5 had a thickness of 11 nm.

Then, exemplified compound No. A-1 was deposited on the hole transport layer 5 to form a 20 nm-thick light emission layer 3. In the deposition, the layer was formed under conditions of a degree of vacuum of $1.0 \times 10^{-4}$ Pa and a deposition rate of 0.2 to 0.3 nm/sec.

Further, basophenanthroline (BPhen) was formed as an electron transport layer 6 in a film thickness of 40 nm by vacuum deposition. In the deposition, the degree of vacuum was $1.0 \times 10^{-4}$ Pa and the deposition rate was 0.2 to 0.3 nm/sec.

Then, using a deposition material of aluminum-lithium alloy (lithium concentration: 1 atomic %), a 0.5 nm thick metal film was formed on the above-described organic layer by vacuum deposition, and a 150 nm thick aluminum film was further formed by vacuum deposition to fabricate an organic light emitting device having an electron injection electrode (cathode 4) of an aluminum-lithium alloy film. In the deposition, the layer was formed under conditions of a degree of vacuum of $1.0 \times 10^{-4}$ Pa and a deposition rate of 1.0 to 1.2 nm/sec.

The obtained organic EL device was covered with a protective glass plate and encapsulated by an acrylic resin adhesive in dry air to avoid degradation of the device due to absorption of moisture.

When a voltage of 4.0 V was applied to the device obtained as above with the ITO electrode (anode 2) as a positive electrode and the Al electrode (cathode 4) as a negative electrode, emission of blue light having a center wavelength of 460 nm, an emission luminance of 876 cd/m² and a luminous efficiency of 3.4 lm/W was observed.

Further, when voltage was applied to the device for 100 hours under nitrogen atmosphere with maintaining a current density of 30 mA/cm², the initial luminance of 950 cd/m² turned to 700 cd/m² after 100 hours, indicating that the decrease in luminance was small.

Comparative Example 1

A device was fabricated in the same manner as in Example 8 except that comparative compound K-1 described below was used instead of exemplified compound No. A-1, and similarly evaluated.

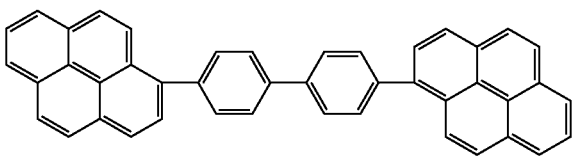

K-1

Emission of blue light of 460 nm with an emission luminance of 350 cd/m$^2$ and a luminous efficiency of 1.6 lm/W was observed at an applied voltage of 4.0 V. Further, when voltage was applied to the device for 100 hours under nitrogen atmosphere with maintaining a current density of 30 mA/cm$^2$, the initial luminance of 450 cd/m$^2$ turned to 160 cd/m$^2$ after 100 hours, indicating that the decrease in luminance was great.

Examples 9 to 10

A device was fabricated in the same manner as in Example 8 except that compounds shown in Table 11 were used instead of exemplified compound No. A-1, and similarly evaluated. The results are shown in Table 11.

TABLE 11

| Ex. | Exemplified compound No. | Applied voltage (V) | Luminance (cd/m$^2$) | Luminous efficiency (lm/W) | Center wavelength (nm) |
|---|---|---|---|---|---|
| 9 | A-2 | 4 | 853 | 3.4 | 458 |
| 10 | A-7 | 4 | 684 | 2.7 | 450 |

Example 11

An organic light-emitting device was fabricated in the same manner as in Example 8 except that 2,9-bis[2-(9,9-dimethylfluorenyl)]phenanthroline was used for the electron transport layer 6.

When a voltage of 4 V was applied to the device obtained as above with the ITO electrode (anode 2) as a positive electrode and the Al—Li electrode (cathode 4) as a negative electrode, emission of blue light having a center wavelength of 460 nm, an emission luminance of 994 cd/m$^2$ and a luminous efficiency of 3.6 lm/W was observed.

Further, when voltage was applied to the device for 100 hours under nitrogen atmosphere with maintaining a current density of 30 mA/cm$^2$, the initial luminance of 950 cd/m$^2$ turned to 700 cd/m$^2$ after 100 hours, indicating that the decrease in luminance was small.

Examples 12 to 19

A device was fabricated in the same manner as in Example 11 except that compounds shown in Table 12 were used instead of exemplified compound No. A-1, and similarly evaluated. The results are shown in Table 12.

TABLE 12

| Ex. | Exemplified compound No. | Applied voltage (V) | Luminance (cd/m$^2$) | Luminous efficiency (lm/W) | Center wavelength (nm) |
|---|---|---|---|---|---|
| 12 | A-2 | 4 | 879 | 3.5 | 458 |
| 13 | A-7 | 4 | 725 | 2.9 | 450 |
| 14 | A-12 | 4 | 580 | 2.5 | 450 |
| 15 | A-13 | 4 | 580 | 2.5 | 450 |
| 16 | A-26 | 4 | 663 | 2.6 | 455 |
| 17 | A-32 | 4 | 489 | 2.1 | 450 |
| 18 | A-40 | 4 | 643 | 2.5 | 455 |
| 19 | A-41 | 4 | 450 | 2.0 | 445 |

Example 20

An organic light-emitting device was fabricated in the same manner as in Example 8 except that a 20 nm-thick light emission layer 3 of 20 nm was formed by co-deposition of exemplified compound No. B-11 as the first compound and exemplified compound No. A-7 as the second compound (weight ratio 10:90) instead of using exemplified compound No. A-1.

When a voltage of 4 V was applied to the device obtained as above with the ITO electrode (anode 2) as a positive electrode and the Al—Li electrode (cathode 4) as a negative electrode, emission of blue light having a center wavelength of 448 nm, an emission luminance of 822 cd/m$^2$ and a luminous efficiency of 2.8 lm/W was observed.

Further, when voltage was applied to the device for 100 hours under nitrogen atmosphere with maintaining a current density of 30 mA/cm$^2$, the initial luminance of 930 cd/m$^2$ turned to 720 cd/m$^2$ after 100 hours, indicating that the decrease in luminance was small.

Examples 21 to 31

A device was fabricated in the same manner as in Example 20 except that compounds shown in Table 13 were used as the first compound and the second compound, and similarly evaluated. The results are shown in Table 13.

TABLE 13

| Ex. | First compound No. | Second compound No. | Applied voltage (V) | Luminance (cd/m$^2$) | Luminous efficiency (lm/W) | Center wavelength (nm) |
|---|---|---|---|---|---|---|
| 21 | B-11 | A-26 | 4 | 829 | 2.8 | 446 |
| 22 | C-7 | A-13 | 4 | 858 | 2.8 | 445 |
| 23 | D-1 | A-31 | 4 | 551 | 2.1 | 443 |
| 24 | E-1 | A-31 | 4 | 588 | 2.3 | 444 |
| 25 | F-3 | A-31 | 4 | 535 | 2.1 | 443 |
| 26 | G-3 | A-13 | 4 | 534 | 2.1 | 443 |
| 27 | B-11 | A-41 | 4 | 2276 | 7.8 | 525 |
| 28 | H-3 | A-2 | 4 | 2276 | 7.8 | 525 |
| 29 | H-19 | A-7 | 4 | 2653 | 10.4 | 530 |
| 30 | I-5 | A-7 | 4 | 3570 | 11.7 | 525 |
| 31 | H-4 | A-40 | 4 | 2510 | 11.4 | 520 |

Comparative Example 2

A device was fabricated in the same manner as in Example 20 except that a 20 nm-thick light emission layer 3 was formed by co-deposition of the following comparative compound No. K-2 as the first compound and comparative compound No. K-1 as the second compound (weight ratio 10:90), and similarly evaluated.

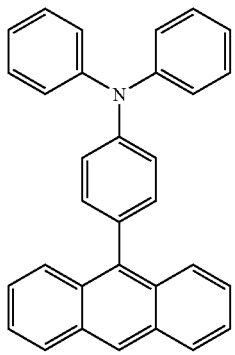

K-2

Emission of green light of 460 nm with an emission luminance of 360 cd/m² and a luminous efficiency of 1.7 lm/W was observed at an applied voltage of 4 V. Further, when voltage was applied to the device for 100 hours under nitrogen atmosphere with maintaining a current density of 30 mA/cm², the initial luminance of 410 cd/m² turned to 150 cd/m² after 100 hours, indicating that the decrease in luminance was great.

Example 32

An organic light-emitting device was fabricated in the same manner as in Example 20 except that 2,9-bis[2-(9,9-dimethylfluorenyl)]phenanthroline was used for the electron transport layer 6.

When a voltage of 4 V was applied to the device obtained as above with the ITO electrode (anode 2) as a positive electrode and the Al—Li electrode (cathode 4) as a negative electrode, emission of blue light having a center wavelength of 448 nm, an emission luminance of 858 cd/m² and a luminous efficiency of 2.9 lm/W was observed.

Further, when voltage was applied to the device for 100 hours under nitrogen atmosphere with maintaining a current density of 30 mA/cm², the initial luminance of 950 cd/m² turned to 750 cd/m² after 100 hours, indicating that the decrease in luminance was small.

Examples 33 to 51

A device was fabricated in the same manner as in Example 32 except that compounds shown in Table 14 were used as the first compound and the second compound, and similarly evaluated. The results are shown in Table 14.

TABLE 14

| Ex. No. | First compound No. | Second compound No. | Applied voltage (V) | Luminance (cd/m²) | Luminous efficiency (lm/W) | Center wavelength (nm) |
|---|---|---|---|---|---|---|
| 33 | B-11 | A-12 | 4 | 910 | 3.0 | 446 |
| 34 | B-11 | A-13 | 4 | 912 | 3.0 | 446 |
| 35 | B-11 | A-41 | 4 | 980 | 3.5 | 446 |
| 36 | B-14 | A-12 | 4 | 1053 | 3.3 | 450 |
| 37 | C-7 | A-29 | 4 | 746 | 2.7 | 445 |
| 38 | E-5 | A-27 | 4 | 592 | 2.3 | 445 |
| 39 | H-4 | A-2 | 4 | 3639 | 11.9 | 530 |
| 40 | H-5 | A-2 | 4 | 3766 | 11.8 | 528 |
| 41 | H-4 | A-12 | 4 | 3574 | 12.2 | 530 |
| 42 | H-16 | A-7 | 4 | 3384 | 11.6 | 523 |
| 43 | H-34 | A-12 | 4 | 2597 | 10.2 | 535 |

TABLE 14-continued

| Ex. No. | First compound No. | Second compound No. | Applied voltage (V) | Luminance (cd/m²) | Luminous efficiency (lm/W) | Center wavelength (nm) |
|---|---|---|---|---|---|---|
| 44 | I-5 | A-2 | 4 | 3639 | 11.9 | 530 |
| 45 | I-5 | A-12 | 4 | 3252 | 11.6 | 530 |
| 46 | I-56 | A-12 | 4 | 1356 | 4.84 | 470 |
| 47 | I-78 | A-27 | 4 | 1144 | 4.1 | 460 |
| 48 | I-80 | A-2 | 4 | 1479 | 4.8 | 470 |
| 49 | A-27 | A-6 | 4 | 869 | 3.1 | 451 |
| 50 | A-35 | A-7 | 4 | 1027 | 3.5 | 454 |
| 51 | A-32 | A-12 | 4 | 765 | 3.0 | 450 |

Further, when voltage was applied to the device of Example 44 for 100 hours under nitrogen atmosphere with maintaining a current density of 60 mA/cm², the initial luminance of 4100 cd/m² turned to 2800 cd/m² after 100 hours, indicating that the decrease in luminance was small.

This application claims priority from Japanese Patent Application No. 2004-342465 filed on Nov. 26, 2004, which is hereby incorporated by reference herein.

What is claimed is:

1. An organic light-emitting device comprising: an anode and a cathode and an organic compound layer disposed between the anode and the cathode, wherein the organic compound layer comprises a host material selected from the group consisting of (A-2) and (A-12) in Compound Group (a) and a guest material selected from the group consisting of (H-4), (H-5), (H-34) and (I-5) in Compound Group (b), wherein Compound Group (a) is (A-2)

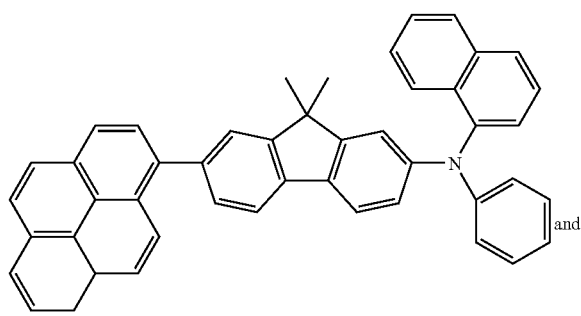

and (A-12)

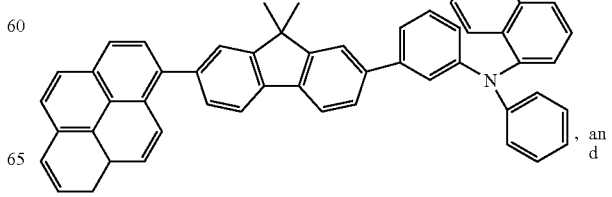

, and

Compound Group (b) is
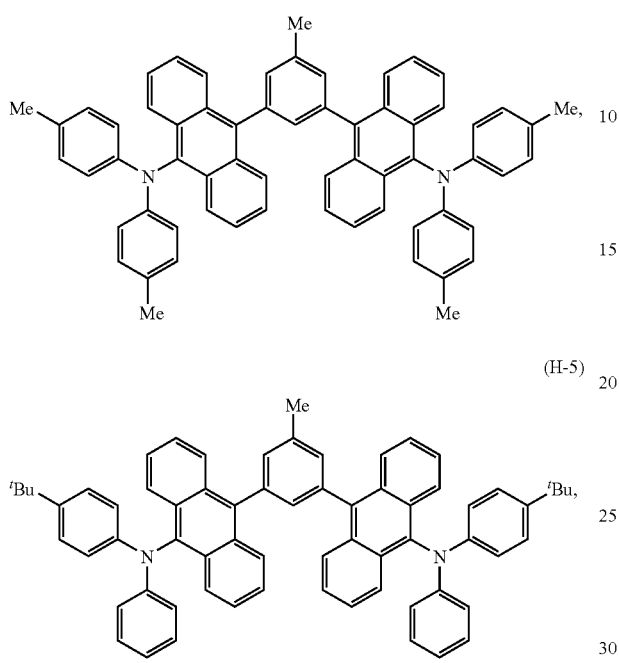
(H-4)
(H-5)
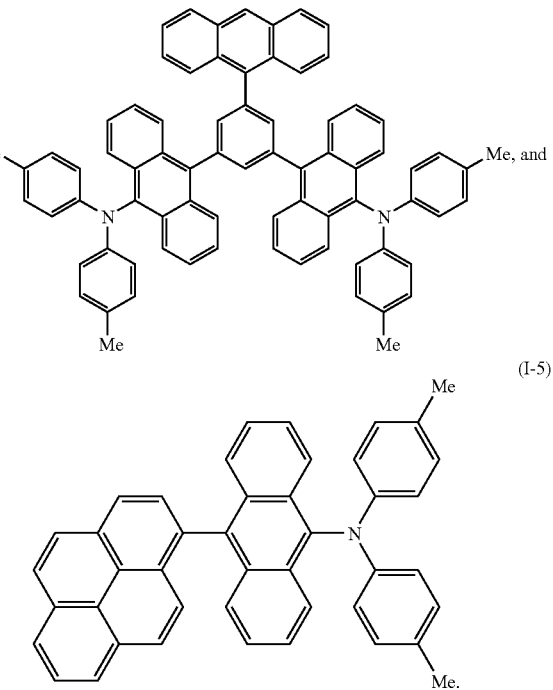
(H-34)
(I-5)
* * * * *